US012655172B2

(12) United States Patent
Dempah et al.

(10) Patent No.: US 12,655,172 B2
(45) Date of Patent: Jun. 16, 2026

(54) SOLID FORMS OF A NUCLEOSIDE ANALOGUE AND USES THEREOF

(71) Applicant: Gilead Sciences, Inc., Foster City, CA (US)

(72) Inventors: Kassibla E. Dempah, San Francisco, CA (US); Chiajen Lai, Livermore, CA (US)

(73) Assignee: Gilead Sciences, Inc., Foster City, CA (US)

( * ) Notice: Subject to any disclaimer, the term of this patent is extended or adjusted under 35 U.S.C. 154(b) by 398 days.

(21) Appl. No.: 18/215,881

(22) Filed: Jun. 29, 2023

(65) Prior Publication Data

US 2024/0043466 A1 Feb. 8, 2024

Related U.S. Application Data

(60) Provisional application No. 63/357,346, filed on Jun. 30, 2022.

(51) Int. Cl.
*C07H 17/02* (2006.01)
*C07H 1/06* (2006.01)

(52) U.S. Cl.
CPC ............... *C07H 17/02* (2013.01); *C07H 1/06* (2013.01); *C07B 2200/13* (2013.01)

(58) Field of Classification Search
CPC ...................................................... C07H 17/02
USPC ............................................ 514/23; 536/29.2
See application file for complete search history.

(56) References Cited

U.S. PATENT DOCUMENTS 4,816,570 A 3/1989 Farquhar
4,894,376 A 1/1990 Morad et al.
4,968,788 A 11/1990 Farquhar
5,663,159 A 9/1997 Starrett, Jr. et al.
5,792,756 A 8/1998 Starrett, Jr. et al.
6,312,662 B1 11/2001 Erion et al.
6,475,985 B1 11/2002 Wagner et al.
6,476,030 B1 11/2002 Carling et al.
6,639,059 B1 10/2003 Kochkine et al.
6,656,915 B1 12/2003 Bantia et al.
6,909,011 B2 6/2005 Skrane et al.
7,078,403 B1 7/2006 Wu et al.
7,105,493 B2 9/2006 Sommadossi et al.
7,125,855 B2 10/2006 Bhat et al.
7,166,604 B2 1/2007 Watson et al.
7,176,203 B2 2/2007 Chambers et al.
7,268,119 B2 9/2007 Cook et al.
7,285,658 B2 10/2007 Cook et al.
7,368,437 B1 5/2008 Bojack et al.
7,390,791 B2 6/2008 Becker et al.
7,429,571 B2 9/2008 Chand et al.
7,514,410 B2 4/2009 Babu et al.
7,560,434 B2 7/2009 Baba et al.
7,598,230 B2 10/2009 Cook et al.
7,608,597 B2 10/2009 Sommadossi et al.
7,713,941 B2 5/2010 Cook et al.
7,803,788 B2 9/2010 Becker et al.
7,807,653 B2 10/2010 Cook et al.
7,842,672 B2 11/2010 Boojamra et al.
7,951,787 B2 5/2011 McGuigan
7,973,013 B2 7/2011 Cho et al.
7,994,139 B2 8/2011 Babu et al.
8,008,264 B2 8/2011 Butler et al.
8,012,941 B2 9/2011 Cho et al.
8,012,942 B2 9/2011 Butler et al.
8,071,568 B2 12/2011 Narjes et al.
8,119,607 B2 2/2012 Francom et al.
8,242,085 B2 8/2012 Babu et al.
8,318,682 B2 11/2012 Butler et al.
8,415,308 B2 4/2013 Cho et al.
8,455,451 B2 6/2013 Cho et al.
8,853,171 B2 10/2014 Butler et al.
8,871,737 B2 10/2014 Smith et al.
8,889,159 B2 11/2014 Clearly et al.
8,980,865 B2 3/2015 Wang
9,090,642 B2 7/2015 Cho et al.
9,243,022 B2 1/2016 Beigelman et al.
9,249,174 B2 2/2016 Beigelman et al.
9,278,990 B2 3/2016 Smith et al.
9,388,208 B2 7/2016 Clarke et al.
9,393,256 B2 7/2016 Ray et al.
9,452,154 B2 9/2016 Delancy et al.
9,481,703 B2 11/2016 Kalayanov et al.

(Continued)

FOREIGN PATENT DOCUMENTS

CN 108084192 5/2018
CN 109748944 A 5/2019

(Continued)

OTHER PUBLICATIONS

"Molecular Nuclear Medicine," First Edition, Wang (ed.), May 31, 2001, 388-391, 11 pages (with English translation).
"Veterinary Microbiology," 4th Edition, Lu (ed.), 2007, p. 304: paragraph 2, p. 408: paragraph 1, p. 419: paragraphs 1-2, 7 pages (with English translation).
[No Author Listed], "Definitive Rules for Nomenclature of Organic Chemistry," Journal of the American Chemistry Society, Nov. 1, 1960, 82(21):5545-5574.
Adlington et al., "Synthesis of novel C-nucleosides with potential applications in combination and parallel synthesis," Tetrahedron Letters, 2000, 41:575-578.

(Continued)

*Primary Examiner* — Traviss C McIntosh, III
(74) *Attorney, Agent, or Firm* — Fish & Richardson P.C.

(57) ABSTRACT

The present disclosure relates to solid forms (e.g. crystalline forms, solvates, and crystalline forms thereof) of a compound which is ((2R,3S,4R,5R)-5-(4-aminopyrrolo[2,1-f][1,2,4]triazin-7-yl)-5-cyano-3,4-dihydroxytetrahydrofuran-2-yl)methyl neopentyl carbonate, which is useful in the treatment of treating viral infections, for example paramyxoviridae, pneumoviridae, picornaviridae, flaviviridae, filoviridae, arenaviridae, orthomyxovirus, and coronaviridae infections.

33 Claims, 8 Drawing Sheets

(56) References Cited

U.S. PATENT DOCUMENTS 9,487,544 B2 11/2016 Cho et al.
9,504,701 B2 11/2016 Casola et al.
9,540,411 B2 1/2017 Kalayanov et al.
9,549,941 B2 1/2017 Cleary et al.
9,605,018 B2 3/2017 Wang et al.
9,616,076 B2 4/2017 Casola et al.
9,701,682 B2 7/2017 Clarke et al.
9,724,360 B2 8/2017 Chun et al.
9,828,408 B2 11/2017 Kalayanov
RE46,762 E 3/2018 Butler et al.
9,938,283 B2 4/2018 Pandey et al.
9,949,994 B2 4/2018 Chun et al.
10,023,600 B2 7/2018 Butler et al.
10,034,893 B2 7/2018 Luly et al.
10,059,716 B2 8/2018 Clarke et al.
10,065,958 B2 9/2018 Mackman et al.
10,251,898 B2 4/2019 Chun et al.
10,251,904 B2 4/2019 Clarke et al.
10,287,307 B2 5/2019 Lai et al.
10,377,761 B2 8/2019 Clarke et al.
RE47,589 E 9/2019 McGuigan
10,675,296 B2 6/2020 Larson
10,682,368 B2 6/2020 Perron et al.
10,695,357 B2 6/2020 Chun et al.
10,695,361 B2 6/2020 Clarke et al.
10,696,679 B2 6/2020 Mackman et al.
10,836,787 B2 11/2020 Brak et al.
10,988,498 B2 4/2021 Butler et al.
11,007,208 B2 5/2021 Clarke et al.
11,225,508 B1 1/2022 Baric et al.
11,260,070 B2 3/2022 Perron et al.
11,266,666 B2 3/2022 Chun et al.
11,266,681 B2 3/2022 Larson et al.
11,344,565 B2 5/2022 Axt et al.
11,377,456 B2 7/2022 Souza et al.
11,382,926 B2 7/2022 Clarke et al.
11,491,169 B2 11/2022 Cihlar
11,492,353 B2 11/2022 Mackman et al.
11,541,071 B1 1/2023 Liang et al.
11,597,742 B2 3/2023 Brak et al.
11,613,553 B2 3/2023 Badalov et al.
11,638,715 B2 5/2023 Burns et al.
11,660,307 B2 5/2023 Cihlar et al.
11,701,372 B2 7/2023 Ellis et al.
11,780,844 B2 10/2023 Bartlett et al.
11,814,406 B2 11/2023 Bunyan et al.
11,845,755 B2 12/2023 Bartlett et al.
11,851,438 B2 12/2023 Bartlett et al.
11,903,953 B2 2/2024 Cihlar
11,926,645 B2 3/2024 Bunyan et al.
11,939,347 B2 3/2024 Byun et al.
11,975,012 B2 5/2024 Cihlar
11,975,017 B2 5/2024 Larson et al.
12,012,431 B2 6/2024 Mohan
12,030,906 B2 7/2024 Brak et al.
12,180,217 B2 * 12/2024 Bartlett ................ A61K 9/0053
2003/0050229 A1 3/2003 Sommadossi et al.
2003/0092775 A1 5/2003 Ernst et al.
2004/0006002 A1 1/2004 Sommadossi et al.
2004/0023901 A1 2/2004 Cook et al.
2004/0063638 A1 4/2004 Roberts et al.
2004/0067901 A1 4/2004 Bhat et al.
2004/0138170 A1 7/2004 Montgomery et al.
2005/0129764 A1 6/2005 Vergez et al.
2005/0187180 A1 8/2005 Loeb et al.
2005/0209166 A1 9/2005 Eckhardt et al.
2005/0215513 A1 9/2005 Boojamra et al.
2005/0250728 A1 11/2005 Bantia et al.
2006/0058303 A1 3/2006 Chambers et al.
2006/0142238 A1 6/2006 McGuigan
2006/0241064 A1 10/2006 Roberts et al.
2008/0107628 A1 5/2008 Boojamra et al.
2008/0161324 A1 7/2008 Johansen et al.
2008/0280842 A1 11/2008 MacCoss et al.
2009/0004138 A1 1/2009 Francom et al.
2009/0221524 A1 9/2009 Kotra et al.
2009/0233879 A1 9/2009 Reddy et al.
2009/0317361 A1 12/2009 Cho et al.
2010/0015094 A1 1/2010 Babu et al.
2010/0016251 A1 1/2010 Sofia et al.
2010/0021425 A1 1/2010 Butler et al.
2010/0035835 A1 2/2010 Narjes et al.
2010/0035836 A1 2/2010 Francom et al.
2010/0065512 A1 3/2010 Bjorsvik
2010/0129437 A1 5/2010 Gaillard
2010/0203015 A1 8/2010 Butler et al.
2010/0234584 A1 9/2010 Chang
2010/0249068 A1 9/2010 Beigelman et al.
2010/0291031 A2 11/2010 Francom et al.
2010/0298257 A1 11/2010 Ross et al.
2010/0305202 A1 12/2010 Hwang et al.
2011/0070194 A1 3/2011 Cho et al.
2011/0084230 A1 4/2011 Knochel et al.
2011/0230654 A1 9/2011 Butler et al.
2011/0257122 A1 10/2011 Sofia et al.
2011/0293563 A1 12/2011 Butler et al.
2012/0009147 A1 1/2012 Cho et al.
2012/0020921 A1 1/2012 Cho et al.
2012/0027752 A1 2/2012 Mackman et al.
2012/0071434 A1 3/2012 Smith et al.
2012/0107274 A1 5/2012 Clarke et al.
2013/0034521 A1 2/2013 Butler et al.
2013/0143835 A1 6/2013 Eneroth et al.
2013/0281686 A1 10/2013 Cho et al.
2013/0315868 A1 11/2013 Mayes
2013/0344028 A2 12/2013 Butler et al.
2014/0219958 A1 8/2014 Luly et al.
2015/0031687 A1 1/2015 Guo et al.
2015/0111839 A1 4/2015 Mackman et al.
2015/0133395 A1 5/2015 Clarke et al.
2015/0152116 A1 6/2015 Mackman et al.
2015/0210682 A1 7/2015 Han et al.
2015/0252057 A1 9/2015 Guo et al.
2015/0274739 A1 10/2015 Girijavallabhan et al.
2016/0024107 A1 1/2016 Clarke et al.
2016/0058779 A1 3/2016 Casola et al.
2016/0122344 A1 5/2016 Han et al.
2016/0122356 A1 5/2016 Axt et al.
2016/0122374 A1 5/2016 Chun
2016/0176899 A1 6/2016 Schwitter et al.
2016/0220586 A1 8/2016 Andre et al.
2016/0237090 A1 8/2016 Hu et al.
2017/0071964 A1 3/2017 Clark et al.
2018/0346504 A1 12/2018 Brak et al.
2019/0023745 A1 1/2019 Baric et al.
2019/0083525 A1 3/2019 Larson
2020/0197422 A1 6/2020 Axt et al.
2020/0360420 A1 11/2020 Larson
2020/0376014 A1 12/2020 Perron et al.
2021/0052613 A1 2/2021 Chun et al.
2021/0061806 A1 3/2021 Mackman et al.
2021/0283150 A1 9/2021 Cihlar et al.
2021/0309689 A1 10/2021 Badalov et al.
2021/0330685 A1 10/2021 Ellis et al.
2021/0393653 A1 12/2021 Cihlar et al.
2021/0393659 A1 12/2021 Clarke et al.
2021/0403497 A1 12/2021 Butler et al.
2022/0081462 A1 3/2022 Bunyan et al.
2022/0175805 A1 6/2022 Cihlar
2022/0280549 A1 9/2022 Larson et al.
2022/0354873 A1 11/2022 Axt et al.
2022/0356196 A1 11/2022 Byun et al.
2023/0027727 A1 1/2023 Clarke et al.
2023/0040586 A1 2/2023 Byun et al.
2023/0069722 A1 3/2023 Han
2023/0125751 A1 4/2023 Mackman et al.
2023/0151043 A1 5/2023 Bunyan et al.
2023/0233587 A1 7/2023 Cihlar
2023/0279013 A1 9/2023 Bartlett et al.
2023/0279014 A1 9/2023 Bartlett et al.
2023/0279015 A1 9/2023 Bartlett et al.
2023/0295172 A1 9/2023 Bartlett et al.
2023/0295214 A1 9/2023 Badalov et al.
2023/0322813 A1 10/2023 Chun et al.

(56) References Cited

U.S. PATENT DOCUMENTS

| | | | |
|---|---|---|---|
| 2023/0346812 | A1 | 11/2023 | Cihlar et al. |
| 2023/0348519 | A1 | 11/2023 | Brak et al. |
| 2023/0382940 | A1 | 11/2023 | Chun et al. |
| 2024/0009220 | A1 | 1/2024 | Bannister et al. |
| 2024/0024341 | A1 | 1/2024 | Ellis et al. |
| 2024/0051962 | A1 | 2/2024 | Dempah et al. |
| 2024/0091251 | A1 | 3/2024 | Larson et al. |
| 2024/0131045 | A1 | 4/2024 | Davis et al. |
| 2024/0150359 | A1 | 5/2024 | Bartlett et al. |
| 2024/0189334 | A1 | 6/2024 | Davis et al. |
| 2024/0199676 | A1 | 6/2024 | Chun et al. |
| 2024/0207291 | A1 | 6/2024 | Bilello |
| 2024/0239830 | A1 | 7/2024 | Bremner et al. |
| 2024/0246986 | A1 | 7/2024 | Bartlett et al. |
| 2024/0287109 | A1 | 8/2024 | Byun et al. |
| 2024/0317790 | A1 | 9/2024 | Bunyan et al. |
| 2024/0409575 | A1 | 12/2024 | Badalov et al. |
| 2024/0417411 | A1 | 12/2024 | Bartlett et al. |
| 2025/0084088 | A1 | 3/2025 | Ensan et al. |
| 2025/0099476 | A1 | 3/2025 | Dempah et al. |
| 2025/0109157 | A1 | 4/2025 | Mackman et al. |
| 2025/0114369 | A1 | 4/2025 | Bartlett et al. |
| 2025/0197410 | A1 | 6/2025 | Bartlett et al. |
| 2025/0205243 | A1 | 6/2025 | Kocevska |

FOREIGN PATENT DOCUMENTS

| | | | | | |
|---|---|---|---|---|---|
| CN | 110234655 A | | 9/2019 | | |
| CN | 110330540 | | 10/2019 | | |
| CN | 110724174 | | 1/2020 | | |
| CN | 110776512 | | 2/2020 | | |
| CN | 111171078 | | 5/2020 | | |
| CN | 111205294 | | 5/2020 | | |
| CN | 111205327 | | 5/2020 | | |
| CN | 111233869 | | 6/2020 | | |
| CN | 111233929 A | | 6/2020 | | |
| CN | 111265532 | | 6/2020 | | |
| CN | 111440176 | | 7/2020 | | |
| CN | 111548384 | | 8/2020 | | |
| CN | 111961057 | | 11/2020 | | |
| CN | 202011613943.3 | | 12/2020 | | |
| CN | 112778310 | | 5/2021 | | |
| CN | 202110562244.9 | | 5/2021 | | |
| CN | 113754665 | | 6/2021 | | |
| CN | 113185519 | | 7/2021 | | |
| CN | 113214334 A | | 8/2021 | | |
| CN | 113248508 | | 8/2021 | | |
| CN | 113292565 | | 8/2021 | | |
| CN | 113387954 | | 9/2021 | | |
| CN | 113735862 | | 9/2021 | | |
| CN | 113698405 | | 11/2021 | | |
| CN | 114292272 | | 12/2021 | | |
| CN | 113999237 | | 1/2022 | | |
| CN | 114181258 | | 3/2022 | | |
| CN | 114409655 | | 4/2022 | | |
| CN | 114437159 | | 5/2022 | | |
| CN | 114621229 | | 6/2022 | | |
| CN | 114765979 | | 7/2022 | | |
| CN | 114869893 | | 8/2022 | | |
| CN | 115521316 | | 12/2022 | | |
| CN | 115583954 | | 1/2023 | | |
| CN | 116172966 | | 5/2023 | | |
| CN | 116970014 | | 10/2023 | | |
| IN | 202121023147 | | 5/2021 | | |
| IN | 202134041493 | | 9/2021 | | |
| IN | 202011021676 | | 11/2021 | | |
| JP | 2005185235 | | 7/2005 | | |
| JP | 2005187428 | | 7/2005 | | |
| JP | 2017512797 A | * | 5/2017 | ............. | A61P 31/18 |
| WO | WO1991019721 | | 12/1991 | | |
| WO | WO1999045029 | | 9/1999 | | |
| WO | WO2000056734 | | 9/2000 | | |
| WO | WO2000075157 | | 12/2000 | | |
| WO | WO2001032153 | | 5/2001 | | |
| WO | WO2001060315 | | 8/2001 | | |
| WO | WO2001090121 | | 11/2001 | | |
| WO | WO2001091737 | | 12/2001 | | |
| WO | WO2001092282 | | 12/2001 | | |
| WO | WO2002008241 | | 1/2002 | | |
| WO | WO2002018404 | | 3/2002 | | |
| WO | WO2002032920 | | 4/2002 | | |
| WO | WO2002057287 | | 7/2002 | | |
| WO | WO2002057425 | | 7/2002 | | |
| WO | WO2003093272 | | 11/2003 | | |
| WO | WO2003093273 | | 11/2003 | | |
| WO | WO2003100009 | | 12/2003 | | |
| WO | WO2004046159 | | 6/2004 | | |
| WO | WO2004046331 | | 6/2004 | | |
| WO | WO2004112687 | | 12/2004 | | |
| WO | WO2005009418 | | 2/2005 | | |
| WO | WO2005092877 | | 10/2005 | | |
| WO | WO2005123087 | | 12/2005 | | |
| WO | WO2006031725 | | 3/2006 | | |
| WO | WO2006050161 | | 5/2006 | | |
| WO | WO2006064033 | | 6/2006 | | |
| WO | WO2006065335 | | 6/2006 | | |
| WO | WO2006121820 | | 11/2006 | | |
| WO | WO2006133978 | | 12/2006 | | |
| WO | WO2007027248 | | 3/2007 | | |
| WO | WO2007056170 | | 5/2007 | | |
| WO | WO2007062542 | | 6/2007 | | |
| WO | WO2007064883 | | 6/2007 | | |
| WO | WO2007064931 | | 6/2007 | | |
| WO | WO2007065289 | | 6/2007 | | |
| WO | WO2007065829 | | 6/2007 | | |
| WO | WO2007095269 | | 8/2007 | | |
| WO | WO2007097991 | | 8/2007 | | |
| WO | WO2007113294 | | 10/2007 | | |
| WO | WO2007135134 | | 11/2007 | | |
| WO | WO 2008005053 A1 | | 1/2008 | | |
| WO | WO2008005542 | | 1/2008 | | |
| WO | WO2008011406 | | 1/2008 | | |
| WO | WO2008055870 | | 5/2008 | | |
| WO | WO2008079206 | | 7/2008 | | |
| WO | WO2008082601 | | 7/2008 | | |
| WO | WO2008085508 | | 7/2008 | | |
| WO | WO2008089105 | | 7/2008 | | |
| WO | WO2008116064 | | 9/2008 | | |
| WO | WO2008121634 | | 10/2008 | | |
| WO | WO2008141079 | | 11/2008 | | |
| WO | WO2009009951 | | 1/2009 | | |
| WO | WO2009018609 | | 2/2009 | | |
| WO | WO2009131926 | | 10/2009 | | |
| WO | WO2009132123 | | 10/2009 | | |
| WO | WO2009132135 | | 10/2009 | | |
| WO | WO2010002877 | | 1/2010 | | |
| WO | WO2010036407 | | 4/2010 | | |
| WO | WO2010039548 | | 4/2010 | | |
| WO | WO2010093608 | | 8/2010 | | |
| WO | WO2010099458 | | 9/2010 | | |
| WO | WO2010108140 | | 9/2010 | | |
| WO | WO2010135569 | | 11/2010 | | |
| WO | WO2011011303 | | 1/2011 | | |
| WO | WO2010111381 | | 3/2011 | | |
| WO | WO2011035231 | | 3/2011 | | |
| WO | WO2011035250 | | 3/2011 | | |
| WO | WO2011080568 | | 7/2011 | | |
| WO | WO2011123645 | | 10/2011 | | |
| WO | WO2011123668 | | 10/2011 | | |
| WO | WO2011123672 | | 10/2011 | | |
| WO | WO2011150288 | | 12/2011 | | |
| WO | WO2012012465 | | 1/2012 | | |
| WO | WO2012012776 | | 1/2012 | | |
| WO | WO2012039787 | | 3/2012 | | |
| WO | WO2012039791 | | 3/2012 | | |
| WO | WO2012051570 | | 4/2012 | | |
| WO | WO2012040127 | | 5/2012 | | |
| WO | WO2012121764 | | 9/2012 | | |
| WO | WO2012142523 | | 10/2012 | | |
| WO | WO2012158643 | | 11/2012 | | |
| WO | WO2013039861 | | 3/2013 | | |
| WO | WO2013084165 | | 6/2013 | | |
| WO | WO2014033617 | | 3/2014 | | |
| WO | WO2014042433 | | 3/2014 | | |

(56) References Cited

FOREIGN PATENT DOCUMENTS

| | | |
|---|---|---|
| WO | WO2014078463 | 5/2014 |
| WO | WO2014078778 | 5/2014 |
| WO | WO2014116755 | 7/2014 |
| WO | WO2011100131 | 8/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO 2016007765 A1 | 1/2016 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO 2016139128 A1 | 9/2016 |
| WO | WO2017049060 | 3/2017 |
| WO | WO2017165489 | 9/2017 |
| WO | WO2017184668 | 10/2017 |
| WO | WO2018085307 | 5/2018 |
| WO | WO2018099946 | 6/2018 |
| WO | WO2018121678 | 7/2018 |
| WO | WO2018145148 | 8/2018 |
| WO | WO 2018169946 A1 | 9/2018 |
| WO | WO2018204198 | 11/2018 |
| WO | WO2018217906 | 11/2018 |
| WO | WO2019014247 | 1/2019 |
| WO | WO2019053696 | 3/2019 |
| WO | WO2019079594 | 4/2019 |
| WO | WO2019113462 | 6/2019 |
| WO | WO2022098371 | 11/2020 |
| WO | WO2021021717 | 2/2021 |
| WO | WO2021040336 | 3/2021 |
| WO | WO2021050961 | 3/2021 |
| WO | WO2021102363 | 5/2021 |
| WO | WO2021147236 | 7/2021 |
| WO | WO2021154530 | 8/2021 |
| WO | WO 2021168930 A1 | 9/2021 |
| WO | WO2021175296 | 9/2021 |
| WO | WO2021188915 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO 2021236570 A1 | 11/2021 |
| WO | WO2022143473 | 12/2021 |
| WO | WO2022008642 | 1/2022 |
| WO | WO2022029704 | 2/2022 |
| WO | WO2022047065 | 3/2022 |
| WO | WO2022047441 | 3/2022 |
| WO | WO2022081870 | 4/2022 |
| WO | WO2022093895 | 5/2022 |
| WO | WO2022165386 | 8/2022 |
| WO | WO2022174194 | 8/2022 |
| WO | WO2022197950 | 9/2022 |
| WO | WO2022217153 | 10/2022 |
| WO | WO2022217154 | 10/2022 |
| WO | WO2022217155 | 10/2022 |
| WO | WO2022218274 | 10/2022 |
| WO | WO2022222994 | 10/2022 |
| WO | WO2022251663 | 12/2022 |
| WO | WO2022265964 | 12/2022 |
| WO | WO2023009977 | 2/2023 |
| WO | WO2023022216 | 2/2023 |
| WO | WO2023056335 | 4/2023 |
| WO | WO2023078416 | 5/2023 |
| WO | WO 2023102472 A1 | 6/2023 |
| WO | WO2023122212 | 6/2023 |
| WO | WO2023167938 | 9/2023 |
| WO | WO2023167944 | 9/2023 |
| WO | WO 2023168194 A1 | 9/2023 |
| WO | WO 2023168254 A1 | 9/2023 |
| WO | WO2023239665 | 12/2023 |
| WO | WO2024006376 | 1/2024 |
| WO | WO 2024054618 A1 | 3/2024 |
| WO | WO 2024076951 A2 | 4/2024 |
| WO | WO 2024091624 A1 | 5/2024 |
| WO | WO 2024226716 A1 | 10/2024 |
| WO | WO 2025049493 A1 | 3/2025 |

OTHER PUBLICATIONS

Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.

Al-Aly et al., "High-dimensional characterization of post-acute sequelae of COVID-19," Nature, Jun. 2021, 594(7862):259-64.

Al-Aly et al., "Long COVID after breakthrough SARS-CoV-2 infection," Nature Medicine, Jul. 2022, 28(7): 1461-7.

Alavi et al., "Severe SARS-CoV-2 infection in a 32-week pregnant woman treated with Remdesivir-Dexamethasone combination therapy: A case report," Clinical Case Reports, Aug. 2022, 10(8) e6241.

Aleissa et al., "New Perspectives on Antimicrobial Agents: Remdesivir Treatment for COVID-19," Antimicrobial Agents and Chemotherapy, Dec. 2020, 65(1): 18 pages.

Alessandrini et al., "Synthesis of Differently Protected 1-C-methyl-ribofuranoses Intermediates for the Preparation of Biologically Active 1'-C-methyl-ribonucleosides," Journal of Carbohydrate Chemistry, 2008, 27(5):332-344.

Ali et al., "Quantitative structure-activity relationships (QSAR) of two series of O-aryl or N-acyl O-ethyl phosphoramidate and phosphorodiamidate fungicides incorporating amino acid ethyl esters," Bulletin of Environmental Contamination and Toxicology, 2000, 65(4):415-420.

Amstutz et al., "Effects of remdesivir in patients hospitalised with COVID-19: A systematic review and individual patient data meta-analysis of randomised controlled trials," The Lancet Respiratory Medicine, Feb. 2023, 11(5): 453-464.

Anderson et al., "The use of convalescent plasma therapy and remdesivir in the successful management of a critically ill obstetric patient with novel coronavirus 2019 infection: A case report," Case Reports in Women's Health, May 2020, 27: 3 pages.

Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop-remdesivir-with-gilead-thanks-to-37-5m-from-nih> Mar. 1, 2020, 5 pages.

Anonymous, "Gillings research on broad-spectrum antiviral could aid public health response to coronavirus outbreaks",—UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.

Anoshchenko et al., "Pharmacokinetics, Safety, and Tolerability of Obeldesivir (OBV; GS-5245) in Healthy Participants," Poster P2620, Presented at European Congress of Clinical Microbiology and Infectious Diseases (ECCMID), Apr. 15-18, 2023, 1 page.

Arimilli et al., "Synthesis, In Vitro Biological Evaluation and Oral Bioavailability of 9-[2-(phosphonomethoxy)propyl]adenine (PMPA) Prodrugs," Antiviral Chemistry & Chemotherapy, 1997, 8(6):557-564.

Asbun et al., "Synthesis of 5-substituted Pyrimidines. II," Journal of Organic Chemistry, 1968, 31:140-142.

Assiri et al., "Epidemiological, Demographic, and Clinical Characteristics of 47 Cases of Middle East Respiratory Syndrome Coronavirus Disease From Saudi Arabia: A Descriptive Study," The Lancet Infectious Dise Sep. 2013, 13(9):752-61.

(56)        References Cited

OTHER PUBLICATIONS

Austin, "An Introduction to Propensity Score Methods for Reducing the Effects of Confounding in Observational Studies," Multivariate behavioral research, May 2011, 46(3): 399-424.

Baker et al., "Prodrugs of 9-Beta-D-Arabinofuranosyladenine. 1. Synthesis and Evaluation of some 5'-(O-Acyl) Derivatives," Journal of Medicinal Chemistry, Dec. 1978, 21(12): 1218-1221.

Ballini et al., "Enantioselective Synthesis of the Lactone Moiety of the Mevinic Acids using D-Xylose as a Chiral Precursor," Journal of the Chemical Society, Perkin Transactions 1, 1991, pp. 490-491.

Balzarini et al., "Inhibition of Feline (FIPV) and Human (SARS) Coronavirus by Semisynthetic Derivatives of Glycopeptide Antibiotics," Andviral Research, 2006, 72:20-33.

Bandini et al., "Indium tribromide: a highly effective catalyst for the addition of trimethylsilyl cyanide to α-hetero-substituted ketone," Tetrahedron Letters, 2001, 42:3041-3043.

Barker et al., "2,3,5-Tri-O-benzyl-D-ribosyl and -L-arabinosyl Bromides," Journal of Organic Chemistry, 1961, 26(11):4605-4609.

Barl et al., "The halogen/magnesium-exchange using iPrMgCl•LiCl and related exchange reagents," Heterocycles, Jan. 2014, 88(2):827-844.

Barnes, "Corticosteroids: The drugs to beat," European Journal of Pharmacology, Mar. 8, 2006, 533(1-3):2-14.

Barrett et al., "Risk for Newly Diagnosed Diabetes > 30 Days After SARS-CoV-2 Infection Among Persons Aged <18 Years—United States, Mar. 1, 2020-Jun. 28, 2021," MMWR Morbidity and Mortality Weekly Report, Jan. 14, 2022, 71(2):59-65.

Beer et al., "Characteristics of Filoviridae: Marburg and Ebola Viruses," Naturwissenschaften, 1999, 86:8-17.

Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.

Beigel et al., "Remdesivir for the Treatment of Covid-19—Final Report," New England Journal of Medicine, Nov. 5, 2020, 383(19): 1813-1826.

Belokon et al., "Optimized catalysts for the asymmetric addition of trimethylsilyl cyanide to aldehydes and ketones," Tetrahedron, 2001, 57: 771-779.

Benksim et al., "A Novel Stereospecific Synthesis of Glycosyl Cyanides from 1,2-O-sulfinyl Derivatives," Organic Letters, 2004, 6(22): 3913-3915.

Benzaria et al., "Synthesis, In Vitro Antiviral Evaluation, and Stability Studies of Bis(S-acy1-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.

Bhimraj et al., "Infectious Diseases Socie y of America guidelines on the treatment and management of patients with COVID-19," Clinical Infectious Diseases, Apr. 27, 2020, 20 pages.

Bio et al., "Practical Synthesis of a Potent Hepatitis C Virus RNA Replication Inhibitor," J. Org. Chem., 2004, 69(19): 6257-6266.

Bobeck et al., "Advances in Nucleoside Monophosphate Prodrugs as Anti-HCV Agents," Antiviral Therapy, 2010, 15: 935-950.

Bobrowski et al., "Synergistic and Antagonistic Drug Combinations against SARS-CoV-2", Molecular Therapy, Feb. 2021, 29(2):873-885.

Boglione et al., "Risk factors and incidence of long-COVID syndrome in hospitalized patients: does remdesivir have a protective effect?," QJM: An International Journal of Medicine, Dec. 2021, 114(12):865-871.

Bojack et al., "Design and Synthesis of Inhibitors of Adenosine and AMP Deaminases," Organic Letters, 2001, 3(6):839-842.

Bonilauri et al., "Animal Coronaviruses and SARS-COV-2 in Animals, What Do We Actually Know?," Life, Feb. 2021, 11(2): 1-17.

Bornholdi et al., "A Two-Antibody Pan-Ebolavirus Cocktail Confers Broad Therapeutic Protection in Ferrets and Nonhuman Primates," Cell Host Microbe, Jan. 2019, 25(1): 49-58, e1-e5.

Bowe et al., "Acute and postacute sequelae associated with SARS-CoV-2 reinfection," Nature Medicine, Nov. 2022, 28(11): 2398-405.

Bowe et al., "Kidney Outcomes in Long COVID," Journal of the American Society of Nephrology, Nov. 2021, 32(11): 2851-62.

Bowie et al., "RIG-I: tri-ing to discriminate between self and non-self RNA," Trends in Immunology, Apr. 2007, 28(4): 147-150.

Boyer et al., "Pathogenesis, diagnosis and management of hepatitis C," Journal of Hepatology, 2000, 32:98-112.

Bozza, "Zika Outbreak, Brazil 2015," ISARIC, 2015, 28 pages.

Bradley et al., "The Management of Community-Acquired Pneumonia in Infants and Children Older Than 3 Months of Age: Clinical Practice Guidelines by the Pediatric Infectious Diseases Society and the Infectious Diseases Society of America," Pediatric Community Pneumonia Guidelines, Clinical Infectious Diseases, Oct. 2011, 53(7):e25-e76.

Brands et al., "Crystallization-Induced Diastereomer Transformations," Chem. Rev., 2006, 106(7): 2711-2733.

Bramman et al., "Post-exposure immunotherapy for two ebolaviruses and Marburg virus in nonhuman primates," Nature Communications, Jan. 2019, 10: 105, 10 pages.

Brittain, "Polymorphism in Pharmaceutical Solids," 2nd Edition, 2009, pp. 183-226, Informa Healthcare USA, Inc.

Brookes et al., "IMPAACT 2032: Remdesivir PK and safety in pregnant and non-pregnant women with COVID-19 [CROI Abstract 676]," Abstracts from CROI 2022 Conference on Retroviruses and Opportunistic Infections, Feb. 2022. 1 page.

Brotschi et al., "Bipyridyl and biphenyl DNA: A recognition motif based on interstrand aromatic stacking," Chemistry—A European Journal, 2005, 11(6):1911-1923.

Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.

Brown et al., "Consistent Effects of Early Remdesivir on Symptoms and Disease Progression Across At-Risk Outpatient Subgroups: Treatment Effect Heterogeneity in PINETREE Study," Infectious Diseases and Therapy, Apr. 2023, 12: 1189-1203.

Brown, "Progress towards improving antiviral therapy for hepatitis C virus polymerase inhibitors," Part O: Nucleoside Analogues, 2009, 18:709-725.

Budi et al., "Remdesivir for pregnancy: A systematic review of antiviral therapy for COVID-19," Heliyon, Jan. 2022,8(1): 10 pages.

Bullard-Feibelman et al., "The FDA-approved drug Sofosbuvir inhibits Zika Virus infection," Antiviral Res., Jan. 1, 2018, 137: 134-140.

Burns, "A Glimmer of Hope for Fatal Feline Disease," JAVMAnews, Dec. 15, 2017, 5 pages.

Burwick et al., "Compassionate Use of Remdesivir in Pregnant Women With Severe Coronavirus Disease," Clinical Infectious Diseases, Dec. 2021, 73(1): e3996-e4004.

Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.

Bwire et al., "Sudan Ebola virus (SUDV) outbreak in Uganda, 2022: lessons learnt and future priorities for sub-Saharan Africa," BMC Medicine, Apr. 2023, 21: 144, 3 pages.

Cabirol et al., "Robust and Efficient, yet Uncatalyzed, Synthesis of Triarylsilyl-protected Cyanohydrins from Ketones," J. Org. Chem., 2008, 73:2446-2449.

Caira, "Crystalline Polymorphism of Organic Compounds," Topics in Current Chemistry, 1998, 198: 163-208.

Cales et al., "Treatment of liver fibrosis: clinical aspects," Gastroentérologie Clinique et Biologique, 2009, 33(10-11): 958-966.

Calisher et al., "Antigenic Relationships between Flaviviruses as Determined by Cross-neutralization Tests with Polyclonal Antisera," Journal of General Virology, 1989, 70: 37-43.

Camps, "Studies on Structurally Simple -αβ-butenolides-II," Tetrahedron, 1982, 38(15): 2395-2402.

(56) References Cited

OTHER PUBLICATIONS

Cao et al., "The Adenosine Analog Prodrug ATV006 is Orally Bioavailable and has Preclinical Efficacy Against Parental SARS-CoV-2 and Variants," Science Translational Medicine, May 2022, 14(661), 16 pages.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRe, retrieved on Jul. 29, 2021, retrieved from URL <"https://www.chemsre.com/en/cas/1476-52-4_1032909.html"> 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRe, retrieved on Jul. 29, 2021, retrieved from URL <"https://www.chemsre.com/en/cas/54-05-7_419322.html">, 16 pages.
CAS Registry No. 1809249-37-3, "L-Alamine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https:commonchemistry.cas.org/detail?cas_rn=1809249-37-3"> 3 pages.
Center for Disease Control and Prevention (CDC) [online], "Animals & COVID-19," COVID-19, last updated Apr. 7, 2023, retrieved on Aug. 29, 2023, retrieved from URL: <https://www.cdc.gov/coronavinis/2019-ncov/daily-life-coping/animals.html> 4 pages.
Center for Disease Control and Prevention (CDC) [online], "Classifications & Definitions, " COVID-19, last updated Mar. 20, 2023, retrieved on Aug. 29, 2023, retrieved from URL: <https://www.cdo.gov/coronavirus/2019-ncov/variants/variant-classifications.html>, 6 pages.
Center for Disease Control and Prevention (CDC) [online], "COVID Data Tracker," last updated Aug. 24, 2023, retrieved on Aug. 25, 2023, retrieved from URL <https://covid.cdc.gov/covid-data-tracker/#datatracker-home> 5 pages.
Center for Disease Control and Prevention (CDC) [online], "People Who Are Immunocompromised," last updated May 1. 023, retrieved from URL <https://www.cdc.gov/coronavirus/2019-ncov/need-extra-precautions/people-who-are-immunocompromised.html>, 4 pages.
Center for Disease Control and Prevention (CDC) [online], "SARS-CoV-2 variant classifications and definitions," last updated Mar. 20, 2023, retrieved on Aug. 25, 2023, retrieved from URL <https://www.cdc.gov/coronavirus/2019-ncov/variants/variant-classifications.html> 6 pages.
Chang et al., "Critical Care Management of a Severe Acute Respiratory Distress Syndrome COVID-19 Patient With Control Cesarean Section," Cureus, Fel ruary 2022, 14(2): 4 pages.
Chapman et al., "RSV604, a Novel Inhibitor of Respiratory Syncytial Virus Replication," Antimicrobial Agents and Chemotherapy, 2007, 51(9): 3346-3353.
Charytan et al., "Decreasing Incidence of Acute Kidney Injury in Patients with COVID-19 Critical Illness in New York City," Kidney International Reports, Apr. 2021, 6(4):916-27.
Chinen et al., "Critical respiratory failure in pregnancy complicated with COVID-19: A case report," Case Reports in Women's Health, Apr. 2021, 30: 4 pages.
Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.
Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.
Choi et al., "Clinical Presentation and Outcomes of Middle East Respiratory Syndrome in the Republic of Korea," Infection & Chemotherapy, Jun. 2016, 48(2): 118-26.
Chokkalingum et al., "Association of Remdesivir Treatment With Mortality Among Hospitalized Adults With COVID-19 in the United States," JAMA Network Open, Dec. 2022, 5(12), 12 pages.
Cihlar et al., "Design and Profiling of GS-9148, a Novel Nucleotide Analog Active against Nucleoside-resistant Variants of Human Immunodeficiency Virus Type 1, and Its Orally Bioavailable Phosphononmidate Prodrug, GS-9131," Antimicrobial Agents and Chemotherapy, 2008, 52(2): 655-665.
Cihlar et al., "Journey of Remdesivir From the Inhibition of Hepatitis C virus to the Treatment of COVID-19," Antiviral Therapy, Mar. 2022, 27(2), 12 pages.
Clark et al., "Design, Synthesis, and Antiviral Activity of 2'-Deoxy-2'-fluoro-2'-C-methyleytidine, a Potent Inhibitor of Hepatitis C Virus Replication," Journal of Medicinal Chemistry, 2005, 48(17): 5504-5508.
Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.
ClinicalTrials.gov [online], "Study of Obeldesivir in Nonhospitalized Participants With COVID-19 (Oaktree)," NCT05715528, last updated Oct. 19, 2023, retrieved on Oct. 19, 2023, retrieved from URL<https://clinicaltrials.gov/study/NCT05715528?term=NCT05715528&rank=1> 13 pages.
ClinicalTrials.gov [online], "Study of Obeldesivir in Participants With COVID-19 Who Have a High Risk of Developing Serious or Severe Illness (BIRCH)," Gilead Sciences, Trial Identifier: NCT05603143, last updated Aug. 3, 2023, retrieved on Aug. 23, 2023, retrieved from URL: <https://classic.clinicaltrials.gov/t2/show/record/NCT05603143>, 8 pages.
Coffin et al., "Persistent Marburg Virus Infection in the Testes of Nonhuman Primate Survivors," Cell Host & Microbe, Sep. 2018, 24(1): 405-416.
Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleie Acids, 2003. 22(11): 2013-2026.
Complexity Scie Hub Vienna [online], "SARS-ANI VIS: A Global Open Access Dataset of Reported SARS-CoV-2 Events in Animals," last updated Jul. 12, 2023, retrieved on Aug. 29, 2023, retrieved from URL: <http://vis.csh.ac.at/sar-ani/#variants>, 2 pages.
Coppock et al., "COVID-19 treatment combinations and associations with mortality in a large multi-site healthcare system," PloS one, Jun. 11, 2021, 16(6): 13 pages.
Cox et al., "Oral prodrug of remdesivir parent GS-441524 is efficacious against SARS-CoV-2 in ferrets," Nature Communications, Nov. 2021, 12(1):1-11.
Cox et al., "Therapeutically administered ribonucleoside analogue MK-4482/EIDD-2801 blocks SARS-CoV-2 transmission in ferrets," Nature Microbiology, 2020, 6(1): 11-18.
Cross et al., Combination therapy protects macaques against advanced Marburg virus disease. Nature Communications, Mar. 2021, 12(1): 1891, 10 pages.
Cross et al., "Combination therapy with remdesivir and monoclonal antibodies protects nonhuman primates against advanced Sudan vinis disease," JCI Insight, May 2022, 7(10): 1-14.
Cross et al., "Natural history of nonhuman primates after conjunctival exposure to Ebola virus," Scientific Repor Mar. 2023, 13(1), 12 pages.
Dai et al., "Synthesis of 2'C-β- Fluoromethyluridine," Organic Letters, 2003, 5(6): 807-810.
Damont et al., "Synthesis of 1'-C-Fluoramethyladenosine," Nucleosides, Nucleotides , and Nucleic Acids, 2007, 26:1431-1434.
Dande et al., "Remdesivir in a pregnant patient with COVID-19 pneumonia," Journal of Community Hospital Internal Medicine Perspectives, Jan. 2021, 11(1): 103-6.

(56) References Cited

OTHER PUBLICATIONS

Davis et al., "Dose Optimization of Obeldesivir for COVID-19 Treatment in Patients With Renal Impairment Using Population Pharmacokinetic Modeling," Presented at the Fourteenth American Conference on Pharmacometrics (ACoP14), Nov. 5-8, 2023, National Harbor, MD, USA, 1 page.
Davis et al., "Long COVID: major findings, mechanisms and recommendations," Nature Reviews Microbiology, Jan. 13, 2023, 21(3): 133-146.
De Clercq, "Antiviral Drugs: Correr State of the Art," J. Clin. Virol., 2001, 22(1): 73-89.
De Clercq, "Molecular Targets for Antiviral Agents," The Journal of Pharmacology and Experimental Therapeutics, 2001, 297(1): 1-10.
De Francesco et al., "Approaching a New Bra for Hepatitis C Virus Therapy: Inhibitors of the NS3-4A Serine: Protease and the NS5B RNA-Dependent RNA Polymerase," Antiviral Research, 2003, 58(1): 1-16.
De Las Heras, "Synthesis of Ribosyl and Arabinosyl Cyanides by Reaction of I-O-Acyl Sugars with Trimethylsilyl Cyanide," Journal of the Chemical Society, Perkin Transactions 1, 1982, pp. 903-907.
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.
De Wit et al., "Prophylactic and Therapeutic Remdesivir (GS-S734) Treatment in the Rhesus Macaque Model of MERS-CoV Infection," Proceedings of the National Academy of Sciences of the United States of America, Mar. 2020, 117(12): 6771-6776.
De Wit et al., "SARS and MERS: Recent Insights Into Emerging Coronaviruses," Nature Review, Jun. 2016: 14: 523-34.
Dehghan et al., "A Lesson for the Future: Determining the Prognosis of the Pregnant Patients with COVID-19 in the Second Trimester? A Case Report," Caspian Journal of Internal Medicine, Apr. 2022, 13(Suppl 3): 284-288.
DeWolf et al., "SARS-CoV-2 in immunocompromised individuals," Immunity, Oct. 11, 2022; 55(10): 1779-98.
Di Bisceglie et al., "The Unmet Challenges of Hepatitis C," Scientific American, Oct. 1999, pp. 80-85.
Dinnon et al., "A mouse-adapted model of SARS-CoV-2 to test COVID-19 countermeasures," Nature, Aug. 2020, 586: 560-566.
Dolzhenko et al., "Pyrazolo[1,5-a][1,3,5]Triazines(5-Aza-9-Deazapurines): Synthesis and Biological Activity," Heterocycles, 2008, 75(7): 1575-1622.
Domingo et al., "The quasispecies (extremely heterogeneous) nature of viral RNA genome populations: biological relevance—a review," Gene, 1985, 40: 1-8.
Dondoni et al., "Thiazole-Based Synthesis of Formyl C-Glycosides," Journal of Organic Chemistry, 1994, 59: 6404-6414.
Douafer et al., "Scope and limitations on aerosol drug delivery for the treatment of infections respiratory diseases," Journal of Controlled Release, Sep. 2020, 325: 276-292.
Dudfield et al., "Synthesis of C-ribosyl imidazo[2,1-f][1,2,4]triazines as inhibitors of adenosine and AMP deaminases," J. Chem. Soc, Perkin Trans 1, 1999, pp. 2929-2936.
Dudfield et al., "Synthesis of C-ribosyl 1,2,4-triazolo[3,4-f][1,2,4 ]triazines as Inhibitors of Adenosine und AMP Deaminasses," J. Chem. Soc., Perkin Trans. 1, 1999, pp. 2937-2942.
Durean et al., "Hydroxychloroquine Blood Levels in Systemic Lupus Erythematosus: Clarifying Dosing Controversies and Improving Adherence", Journal of Rheumatology, 2015, 42(11):2092-2097.
Dymock et al., "Novel approaches to the treatment of hepatitis C virus infection," Antiviral Chemistry & Chemotherapy, 2000, 11(2): 79-96.
Easterlin et al., "Extremely Preterm Infant Born to a Mother With Severe COVID-19 Pneumonia," Journal of Investigative Medicine High Impact Case Reports, Jul. 2020. 8: 1-5.
Eastman et al., "Remdesivir: A Review of Its Discovery and Development Leading to Emergency Use Authorization for Treatment of COVID-19," ACS Central Science, May 4, 2020; 6(5): 672-83.
Eid et al., "Early Administration of Remdesivir and Intensive Care Unit Admission in Hospitalized Pregnant Individuals With Coronavirus Disease 2019 (COVID-19)," Obstetrics & Gynecology, Apr. 2022, 139(4): 619-621.
El Safadi et al., "5-Modified-2' dU and 2'-dC as Mutagenic Anti HIV-1 Proliferation Agents: Synthesis and Activity," Journal of Medicinal Chemistry, 2010, 53(4): 1534-1545.
ERA-EDTA Council et al., "Chronic kidney disease is a key risk factor for severe COVID-19: a call to action by the ERA-EDTA," Nephrology Dialysis Transplantation, Jan. 2021, 36(1): 87-94.
Escaffre et al., "STAT-1 Knockout Mice as a Model for Wild-Type Sudan Virus (SUDV)," Viruses, Jul. 2021, 13(7): 1-16.
European Centre for Disease Prevention and Control (ECDC) [online], "SARS-CoV-2 variants of concern as of Aug. 24, 2023," last updated Aug. 24, 2023, retrieved on Aug. 29, 2023, retrieved from URL: <https://www.ecdc.europa.eu/en/covid-19/variants-concern>, 18 pages.
European Medicines Agency, "New vaccine for prevention of Ebola virus disease recommended for approval in the European Union," Press Release, May 29, 2020, 3 pages.
European Medicines Agency, "Summary on compassionate use: Remdesivir Gilead," Procedure No. EMEA/H/K/005622/CU, Apr. 3, 2020, 45 pages.
Fan et al., "Safety Hle of the antiviral drug remdesivir: An update," Biomedicine & Pharmacotherapy, Oct. 2020 130:3 pages.
Farquhar et al., "Biologically Reversible Phosphate-Protective Groups," Journal of Pharmaceutical Sciences, 1983, 72(3): 324-325.
Fauquet et al., "Abbreviations for vertebrate virus species names", Archives of Virology, Dec. 31, 1999, pp. 1865-1880.
fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.
Feldmann et al., "Chapter 32: Filoviridae: Marburg and Ebola Viruses," in Fields Virology, Sixth Edition, May 2013, 1: 36 pages.
Feldmann et al., "Ebola," New England Journal of Medicine, May 2020, 382: 1832-42.
Flint et al., "Functional analysis of cell surface-expressed hepatitis C virus E2 glycoprotein," J. Virol., Aug. 1999, 73(8): 6782-6790.
Flythe et al., "Characteristics and Outcomes of Individuals With Pre-existing Kidney Disease and COVID-19 Admitted to Intensive Care Units in the United States," American Journal of Kidney Diseases, Feb. 2021, 77(2): 190-203.
Food and Drug Administration (FDA), "Estimating the Maximum Safe Starting Dose in Initial Clinical Trials for Therapeutics in Adult Healthy Volunteers," Jul. 2005, 30 pages.
Food and Drug Administration (FDA), "Fact Sheet for Healthcare Providers: Emergency Use Authorization for Lagevrio™ (molnupiravir) Capsules," FDA Emergency Use Authorization, published Dec. 2021, 21 pages.
Food and Drug Administration (FDA), "Highlights of Prescribing Information for Paxlovid™" revised May 2023, 51 pages.
Foster et al., "Deuterium isotope effects in studies of drug metabolism," Trends in Pharmacological Sciences, Jan. 1984, 5:524-527.
Franchetti et al., "Antitumor Activity of C-Methyl-β-D-ribofuranosyladenine Nuceoside Ribonuceotide Reductase Inhibitors," J. Med. Chem. 2005, 48: 4983-4989.
Freeman et al., "3 Prodrug Design for Phosphates and Phosphonates," Progress in Medicinal Chemistry, 1997, 34: 111-147.
Fukumoto et al., "Viral Dynamics of Hepatitis C Early After Orthotopic Liver Transplantation: Evidence for Rapid Turnover of Serum Virions," Hepatology, 1996, 24: 1351-1354.
Fuse, "Organic Synthesis Using Microflow Reactor," Journal of Synthetic Organic Chemistry Japan, 2012, 70(2): 177-178 (with English abstract).

(56) References Cited

OTHER PUBLICATIONS

Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.
Gardelli et al., "Phosphorumidate Prodrugs of 2'-C-Methyleytidine for Therapy of Hepatitis C Virus Infection," Journal of Medicinal Chemistry, 2009, 52(17): 5394-5407.
Garnett et al., "Scientific white paper on concentration-QTe modeling," J. Pharmacokinet Pharmacodyn., Jun. 2018; 45(3):383-397.
Geisbert et al., "Considerations in the Use of Nonhuman Primate Models of Ebola Virus and Marburg Virus Infection," The Journal of Infectious Diseases, Oct. 2018, 212(Suppl, 2), S91-97.
Geisbert et al., "Single-injection vaccine protects nonhuman primates against infection with marburg virus and three species of ebola virus," Journal of Virology, Jul. 2009, 83(14): 7296-7304.
George et al., "Preparation of silyl- and germylmetallic compounds," Journal of the American Chemical Society, Jan. 1960, 82(2):403-6.
Gil et al., "COVID-19: Drug Targets and Potential Treatments," Journal of Medicinal Chemistry, Jun. 2020, 63(21): 12359-12386.
Gilead Sciences, Inc., "Veklury 100 mg powder for concentrate for solution for infusion," Package Leaflet, last revised Jun. 2023, 12 pages.
Gilead Sciences, Inc., "Veklury™ (remdesivir) Full Prescribing Information" last revised Jul. 2023, 44 pages.
Gleeson et al., "Prediction of the Potency of Inhibitors of Adenosine Deaminase by QM/MM Calculations," Chem. Commun., 2003, pp. 2180-2181.
Goldman et al., "COVID-19 in immunocompromised populations: implications for prognosis and repurposing of immunotherapies," Journal for Immunotherapy of Cancer, Jun. 11, 2021, 9(6): 1-13.
Goldman et al., "Remdesivir for 5 or 10 Days in Patients with Severe Covid-19," New England Journal of Medicine, May 2020, 383(19), 1827-37.
Gordon et al., "Control of Hepatitis C: A Medicinal Chemistry Perspective," J. Med. Chem., 2005, pp. 1-20, vol. 48, No. 1.
Gordon et al., "Efficient Incorporation and Template-Dependent Polymerase Inhibition are Major Determinants for the Broad Spectrum Antiviral Activity of Remdesivir," Journal of Biological Chemistry, Dec. 2021, 298(2): 14 pages.
Gordon et al., "Remdesivir is a direct-acting antiviral that inhibits RNA-dependent RNA polymerase from severe acute respiratory syndrome coronavirus 2 with high potency," J. Biol, Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Gottlieb et al., "Early Remdesivir to Prevent Progression to Severe Covid-19 in Outpatients," New England Journal of Medicine, Jan. 27, 2022, 386(4): 305-315.
Greene et al., "Protective Groups in Organic Synthesis," John Wiley & Sons., 1991, pp. 118-142.
Greene et al., "Protective Groups in Organic Synthesis," published by John Wiley & Sons, v Inc., 1991, pp. 1-4, 10-14, 47-53 and 100-103.
Grein et al., "Compassionate Use of Remdesivir for Patients with Severe Covid-19", The New England Journal of Medicine, Apr. 2020, 382(24): 2327-2336.
Gudmundsson et al., "Synthesis of imidazo[1,2-a]pyridine C-Nucleosides with an Unexpected Site of Ribosylation," Journal of Organic Chemistry, 1997, 62: 3453-3459.
Gudmundsson et al., "The Condensation of 2,6-dichloroimidazo [1,2-a ]pyridine C-nucleoside with an Unexpected Site of Ribosylation," Tetrahedron Letters, 1996, 7(14): 2365-2368.
Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.
Gupta et al., "Factors Associated With Death in Critically Ill Patients With Coronavirus Disease 2019 in the US," JAMA Internal Medicine, Nov. 2020, 180(11): 1436-47.
Gutierrez et al., "Remdesivir use in pregnancy during the SARS-CoV-2 pandemic," The Journal of Maternal-Fetal & Neonatal Medicine, Feb. 2022; 35(25): 9445-51.
Hadi et al., "Outcomes of COVID- 19 in Solid Organ Transplant Recipients: A Propensity-matched Analysis of a Large Research Network," Transplantation, Jun. 1, 2021; 105(6): 1365-71.
Hamann et al., "Synthesis and antiviral evaluation of 7,9-dideaza-8-thiapurine C-nucleoside derivatives," Collection Symposium Series, 2008, 10: 347-349.
Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.
Hammond et al., "Oral Nirmatrelvir for High-Risk, Nonhospitalized Adults with Covid-19, New England Journal of Medicine," Feb. 2022, 386(15): 1397-1408.
Han et al., "Genetic, antigenie and pathogenic characterization of avian coronaviruses isolated from pheasants (*Phasianos colchicus*) in China," Veterinary Microbiology, Nov. 2019, 240: 1-14.
Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.
Hanson et al., "Estimated Global Proportions of Individuals With Persistent Fatigue, Cognitive, and Respiratory Symptom Clusters Following Symptomatic COVID-19 in 2020 and 2021," JAMA Network, Oct. 10, 2022; 328(16): 1604-1615.
Haraguchi et al., "Stereoselective Synthesis of 1'-C-Branched Uracil Nucleosides From Uridine," Nucleosides & Nucleotides, 1995, 14(3-5): 417-420.
Harcourt et al., "Molecular Characterization of the Polymerase Gene and Genomic Termini of Nipah Virus," Virology, 2001, 287: 192-201.
Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.
Harvey et al., "Association of SARS-CoV-2 Seropositive Antibody Test With Risk of Future Infection," JAMA Internal Medicine, Feb. 24, 2021; 181(5): 672-679.
Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.
Hayashi et al., "Gasless laparoendoscopic single-site surgery for management of unruptured tubal pregnancy in a woman with moderate COVID-19 pneumonia after administration of remdesivir and casirivimab-imdevimab: A case report," Case Reports in Women's Health, Jan. 2022, 33: e00368.
He et al., Species Differences in Size Discrimination in the Paracellular Pathway Reflected by Oral Bioavailability of Poly(ethylene glycol) and D-peptides, Journal of Pharmaceutical Sciences, May 1998, 87(5): 626-633.
Hecker et al., "Liver Targeted Prodrugs of 2'-C-Methyladenosine for Therapy of Hepatitis C Virus Infection," J. Med. Chem., 2007, 50(16): 3891-3896.
Henry et al., "Chronic kidney disease is associated with severe coronavirus disease 2019 (COVID-19) infection," International urology and nephrology, Jun. 2020, 52(6): 1193-4.
Herbert et al., "Development of an antibody cocktail for treatment of Sudan virus infection," Proceedings of the National Academy of Sciences, Feb. 2020, 117: 3768-78.
Higgs et al., "Prevail IV: A Randomized, Double-Blind, 2-Phase, Phase 2 Trial of Remdesivir vs Placebo for Reduction of Ebola Virus RNA in the Semen of Male Survivors," Clinical Infectious Diseases, Nov. 2021, 73(10): 1849-1856.
Hoffinann et al., "When, in the context of drug design, can a fluorine atom successfully substitute a hydroxyl group?," International Journal of Quantum Chemistry, 2002, 89: 419-427.
Holshue et al., "First Case of 2019 Novel Coronavirus in the United States", The New England Journal of Medicine, Jan. 2020, 9 pages.

(56) References Cited

OTHER PUBLICATIONS

Hop et al., "Plasma-pooling methods to increase throughput for in vivo pharmacokinetic screening," Journal of Pharmaceutical Sciences, Jul. 1998, 87(7):901-903.
Hoste et al., "Assessment of renal function in recently admitted critically ill patients with normal serum creatinine," Nephrology Dialysis Transplantation, Apr. 2005, 20(4): 747-53.
Hsu et al., COVID-19 Among US Dialysis Patients: Risk Factors and Outcomes From a National Dialysis Provider, American Journal of Kidney Disease, May 2021, 77(5):748-56.
Huang et al., "Recent development of therapeutics for chronic HCV infection," Antiviral Research, Sep. 2006, 71(2-3): 351-362.
Humenink et al., "Pharmacokinetic, Pharmacodynamic, and Drug Interaction Profile of Remdesivir, a SARS-CoV-2 Replication Inhibitor," Clinical pharmacokinetics, May 2021, 60(2021): 569-583.
Igbinosa et al., "Use of remdesivir for pregnant patients with severe novel coronavirus disease 2019," American Journal of Obstetrics & Gynecology, Aug. 2020, 223(5): 768-770.
Ioannou et al., "Rates and Factors Associated With Documentation of Diagnostic Codes for Long COVID in the National Veterans Affairs Health Care System," JAMA Network Open, Jul. 29, 2022, 5(7): 1-11.
Itoh et al., "Divergent and Stereocontrolled Approach to the Synthesis of Uracil Nucleosides Branched at the Anomeric Position," J. Org. Chen, 1995, 60: 656-662.
Jacobson et al., "Use of dexamethasone, remdesivir, convalescent plasma and prone positioning in the treatment of severe COVID-19 infection in pregnancy: A case report," Case Reports in Women's Health, Jan. 2021, 29: 3 pages.
Jasko et al., "5'-Phosphonates of Ribonucleosides and 2'-Deoxyribonucleosides: Synthesis and Antiviral Activity," Nucleosides & Nucleotides, 1993, 12(8): 879-893.
Jeong et al., "Detecting drug-drug interactions between therapies for COVID-19 and concomitant medications through the FDA adverse event reporting system," Frontiers in Pharmacology, Jul. 22, 2022, 13: 14 pages.
Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.
Jones et al., "Di- and Triester Prodrugs of the Varicella-Zoster Antiviral Agent 6-Methoxypurine Arabinoside," Journal of Medicinal Chemistry, Jan. 1992, 35(1):56-63.
Jorgensen et al., "A review of remdesivir for COVID-19 in pregnancy and lactation," Journal of Antimicrobial Chemothe ugust 2021, 77(1): 24-30.
Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.
Julander et al., "Remdesivir efficacy against yellow fever in a hamster model," Antiviral Research, Jul. 2022, 203:105331.
Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.
Kabinger et al., "Mechanism of Molnupiravir-Induced SARS-CoV-2 Mutagenesis," Nature Structural & Molecular Biology, Aug. 2021, 28(9): 740-746.
Kaewkhao et al., "High sensitivity methods to quantify chloroquine and its metabolite in human blood samples using LC-MS/MS", Bioanalysis, Mar. 2019, 11(5):333-347.
Kalil et al., "Baricitinib plus Remdesivir for hospitalized adults with Covid-19," New England Journal of Medicine, Dec. 11, 2020, 13 pages.
Kelly et al., "Post-acute sequelae of SARS-CoV-2 among previously hospitalised individuals with COVID-19: a systematic literature review and meta-analysis," European Respiratory Journal, 2022, 60(Suppl. 66): 4430.
Khamnei et al., "Neighboring Group Catalysis in the Design of Nucleotide Prodrugs," J. Med. Chem., 1996, 39(20): 4109-4115.
Khan et al., "Coronaviruses disease 2019 (COVID-19): Causative agent, mental health concerns, and potential management options," Journal of Infection and Public Health, Dec. 2020, 13(12):1840-1844.
Khbou et al., "Coronavirses in farm animals: Epidemiology and public health implications," Veterinary Medicine and Science, Sep. 2020, 7(2): 322-347.
Kim et al., "Detection of bovine coronavirus in nasal swab of non-captive wild water deer, Korea," Transboundary and Emerging Diseases, Mar. 2018, 65(3): 627-631.
Kim et al., "Reversal of the Progression of Fatal Coronavirus Infection in Cats by a Broad-Spectrum Coronavirus Protease Inhibitor," PLOS Pathogens, Mar. 30, 2016, 18 pages.
Kim et al., "Synthesis and Evaluation of 2-Amino-6-fluoro-9-(4-hydroxy-3-hydroxymethylbut-1-y) purine Mono- and Diesters as Potential Prodrugs of Penciclovir," Bioorganic & Medicinal Chemistry Mar. 1999, 7(3):565-70.
Kim et al., "Synthesis and Evaluation of 2-Amino-9-(1,3-dihydroxy-2-propoxymethyl)-6-fluoropurine Mono- and Diesters as Potential Prodrugs of Ganciclovir," Journal of Medicinal Chemistry, Jan. 1999, 42(2):324-28.
Klumpp et al., "Chapter 20: Discovery and Clinical Evaluation of the Nucleoside Analog Balapiravir (R1626) for the Treatment of HCV Infection," Antiviral Drugs; From Basic Discovery through Clinical Trials, Jun. 20, 2011, pp. 287-304.
Klumpp et al., "The Novel Nucleoside Analog R.1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.
Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.
Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans 1, 1985, pp. 621-630.
Knutsen et al., "Synthesis of Imidazo-fitsed Bridgehead-nitrogen C-Nucleosides via Dehydrative Coupling Reactions of 2,5-Anhydro-3,4,6-tri-O-benzoyl-D-allonie Acid," J. Chem. Soc. Perkin Trans 1, 1984, pp. 229-238.
Kobe et al., "Use of Distance Geometry Approach for the In Vitro Antiviral Activity Evaluation of N-bridgelead C-nucleosides," European J. Med. Chem., 1992. 27(3): 259-266.
Koplon [online], "$37.5 million grant will address research of high-priority infections," UAB News, retrieved on Mar. 13, 2023, URL <https://www.uab.edu/news/health/item/10307-37-5-million-grant-will-address-research-of-high-priority-infections> Mar. 20, 2019, 1 page.
Ksiazek et al., "A Novel Coronavirus Associated with Severe Acute Respiratory Syndrome," New England Journal of Medicine, May 2003, 348(20): 1953-66.
Kuang et al., "Reversion of Ebolavirus Disease from a Single Intramuscular Injection of a Pan-Ebolavirus Imminotherapeutic," Pathogens, Jun. 2022, 11(6): 655, 14 pages.
Kudose et al., "Longitudinal Outcomes of COVID-19-Associated Collapsing Glomerulopathy and Other Podocylopathies," Journal of the American Society of Nephrology, Nov. 2021; 32(11): 2958-69.
Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-35.
Kushner et al., "Pharmacological uses and perspectives of heavy water aid denterated compounds," Canadian Journal of Physiology and Pharmacology, Feb. 1999, 77(2):79-88.
Kuzik et al., "Nebulized Hypertonic Saline in the Treatment of Viral Bronchiolitis in Infants", The Journal of Pediatrics, Sep. 2007, 151(3):266-270.e1.

(56) References Cited

OTHER PUBLICATIONS

Lafont et al., "Targeted SARS-CoV-2 treatment is associated with decreased mortality in immunocompromised patients with COVID-19," Joumal of Antimicrobial Chemotherapy, Jul. 25. 2022, 77(10): 2688-92.
Languon et al., "Filovirus Disease Outbreaks: A Chronological Overview," Virology: Research and Treatment, Jun. 2019, 10: 1-12.
Lat et al., "Therapeutic options in the treatment of severe acute respiratory syndrome coronavirus 2 in pregnant patient," American Journal of Obstetrics & Gynecology MPM, Nov. 2020, 2(4): 100224.
Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.
Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.
Levey et al., "Using standardized serum creatinine values in the modification of diet in renal disease sindy equation for estimating glomerular filtration rate," Annals of Internal Medicine, Aug. 15, 2006, 145(4):247-254.
Leyssen et al., "Molecular strategies to inhibit the replication of RNA Viruses," Antiviral Research, 2008, 78:9-25.
Li et al., "Key Metabolic Enzymes Involved in Remdesivir Activation in Human Lung Cells," Antimicrobial Chemotherapy, Aug. 2021, 65(9): 17 pages.
Li et al., "Remdesivir Metabolite GS-441524 Effectively Inhibits SARS-CoV-2 Infection in Mouse Models," Journal of Medicinal Chemistry, Feb. 2021, 65(4): 2785-2793.
Lim et al., "Pregnancy and Severe ARDS with COVID-19: Epidemiology, Diagnosis, Outcomes and Treatment," Seminars in Fetal and Neonatal Medicine, Feb. 2023, 28(1): 12 pages.
Lin et al., "Animal Coronavirus Diseases: Parallels with COVID-19 in Humans," Viruses, Jul. 2021, 13(8): 1-15.
Lindell et al., "Synthesis and Biochemical Testing of 3-(Carboxyphenylethyl)imidazo[2,1-f][1,2,4] triazines as Inhibitors of AMP Deaminase," ACS Medicinal Chemistry Letters, 2010, 1(6): 286-289.
Liu et al., "Ebola virus persistence and disease recrudescence in the brains of antibody-treated nonhuman primate survivors," Science Translational Medicine, Feb. 2022, 14(631), 13 pages.
Liu et al., "Hydroxychloroquine, a less toxic derivative of chloroquine, is effective in inhibiting SARS-CoV-2 infection in vitro," Cell Discovery, Mar. 18, 2020. 6:16, 4 pages.
Liu et al., "Physiologically-based pharmacokinetic modeling of remdesivir and its metabolites in pregnant women with COVID-19," CPT: Pharmacometrics & Systems Pharmacology, Dec. 2022, 12(2): 148-53.
Lo et al., "Remdesivir (GS-5734) protects African green monkeys from Nipah virus challenge," Science Translational Medicine, May 29, 2019, 11(494):1-6.
Lo et al., "GS-5734 and its parent nucleoside analog inhibit Filo-, Pneumo-, and Paramyxoviruses," Scientific Reports, 2017, 7(43395):1-7.
Lovelette, "1,2,4-Triazines, Synthesis of selected members of the s-triszolo[3,4-f][1,2,4]triazine and tetrazolo[1,5-f][1,2,4]triazine ring systems," Journal of Heterocyclic Chemistry, 1979, 16: 555-560.
Lu, Chengping, Veterinary Microbiology 5th edition, Jan. 31, 2013, p. 431, China Agriculture Press (No English Translation available).
MacKenna et al., "Risk of severe COVID-19 outcomes associated with immune-mediated inflammatory diseases and immune-modifying therapies: a nationwide cohort study in the OpenSafely platform," The Lancet Rheumatology, Jun. 8, 2022, 4(7): e490-e506.
Mackman et al., "Chapter 22: Vekhiry® (Remdesivir), A Nucleotide Prodrug Approved for the treatment of COVID-19," 2022 Medicinal Chemistry Reviews, Dec. 2022, 57: 545-569.
Mackman et al., "Discovery of GS-5245 (Obeldesivir), an Oral Prodrug of Nucleoside GS-441524 that Exhibits Antiviral Efficacy in SARS-CoV-2 Infected African Green Monkeys," BioRxiv, Apr. 28, 2023, 50 pages.
Mackman et al., "Prodrugs of a 1'-CN-4-Aza-7,9-dideazaadenosine C-Nucleoside Leading to the Discovery of Remdesivir (GS-5734) as a Potent Inhibitor of Respiratory Syncytial Virus with Efficacy in the African Green Monkey Model of RSV," Journal of Medicinal Chemistry, Apr. 2021, 64(8): 5001-5017.
Maldarelli et al., "Remdesivir Treatment for Severe COVID-19 in Third-Trimester Pregnancy: Case Report and Management Discussion," Open Forum Infectious Diseases, Sep. 2020, 7(9): 4 pages.
Malin et al., "Remdesivir against COVID-19 and Other Viral Diseases," Clinical Microbiology Reviews, Oct. 14, 2020, 34(1):e00162-20.
Malone et al., "Structural basis for substrate selection by the SARS-CoV-2 replicase," Nature, Feb. 2023, 614(7949): 781-787.
Marikawa et al., "Remdesivir impairs mouse preimplantation embryo development at therapeutic concentrations," Reproductive Toxicology, Aug. 2022, 111: 135-47.
Markham, "REGN-EB3: First Approval," Drugs, Jan. 2021, 81: 175-178.
Martell et al., "Hepatitis C Virus (HCV) Circulates as a Population of Different but Closely Related Genomes: Quasispecies Nature of HCV Genome Distribution," Journal of Virology, 1992, 6695: 3225-3229.
Martin et al., "Genetic Conservation of SARS-CoV-2 RNA Replication Complex in Globally Circulating Isolates and Recently Emerged Variants from Humans and Minks Suggests Minimal Pre-Existing Resistance to Remdesivir," Antiviral Research, Apr. 2021, 188: 7 pages.
Martin et al., "Hint2, A Mitochondrial Apoptotic Sensitizer Down-Regulated in Hepatocellular Carcinoma," Gastroenterology, Jun. 2006, 130(7): 2179-2188.
Martinez et al., "Efficacy of the oral nucleoside prodrug GS-5245 (Obeldesivir) against SARS-CoV-2 and coronaviruses with pandemic potential," BioRxiv, Jun. 28, 2023, 54 pages.
Marzban-Rad et al., "The use of remdesivir among pregnant women and associated clinical ontcomes in mother and the child," Annals of Medicine and Surgery, May 2022, 77: 3 pages.
Mason et al., "Polyadenylation-dependent screening assay for respiratory syncytial virus RNA transcriptase activity and identification of an inhibitor," Nucleic Acids Research, 2004, 32(16): 4758-4767.
Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.
Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.
McCoy et al., "Compassionate use of remdesivir for treatment of severe coronavirus disease 2019 in pregnant women at a United States academic center," American Journal of Obstetrics & Gynecology MFM, Aug. 2020, 2(Suppl 3): 4 pages.
McGuigan et al. "Application of Phosphoramidate ProTide Technology Significantly Improves Antiviral Potency of Carbocyclic Adenosine Derivatives," J. Med. Chem., 2006, 49: 7215-7226.
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.
McGuigan et al., "Design, synthesis and biological evaluation of phosphorodiamidate prodrugs of antiviral and anticancer nucleosides," European Journal of Medical Chemistry, 2013, 70: 326-340.
McGuigan et al., "Intracellular Delivery of Bioactive AZT Nucleotides by Aryl Phosphate Derivatives of AZT" J. Med. Chem., 1993, 36(8): 1048-1052.
Mehellou et al., "Aryloxy Phosphorumidate Triesters: a Technology for Delivering Monophosphorylated Nucleosides and Sugars into Cells," ChemMedChem, 2009, 4:1779-1791.
Meppen et al., "Cyclie phosphoramidates as prodrugs of 2'-C-methylcytidine," European Journal of Medicinal Chemistry, 2009, 49(9): 3765-3770.

(56)                References Cited

OTHER PUBLICATIONS

Meppen et al., "Medi-404—A Prodrug Approach for the Treatment of HCV Infection," Abstracts of papers, 236th ACS National Meeting, Philadelphia, PA, United States, Aug. 17-21, 2008, 1 page.

Metobo et al., "Practical synthesis of 1 '-substituted Tubercidin C-nucleoside analogs," Tetrahedron Letters, Feb. 2012, 53(5):484-486.

Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. I, 1992, pp. 2345-2353.

Mitchell et al., "Synthesis of C-Nucleoside Isosteres of 9-(2-Hydroxyethoxymethyl)guanine (Acyclovir)," J. Het. Chem., 1984, 21(3): 697-699.

Moennig et al., "The Pestiviruses", Advances in Virus Research, 1992, 41: 53-98.

Moorman et al., "5'ester prodrugs of the varicella-zoster antiviral agent, 6-methoxypurine arabinoside," Antiviral Chemistry & Chemotherapy, Jun. 1992, 3(3): 141-46.

Moradpour et al., "Replication of hepatitis C virus," Nature Reviews Microbiology, 2007, 5(6): 453-463.

Morris, "Mechanisms of action and therapeutic role of corticosteroids in asthma", J. Allergy Clin. Immunol., Jan. 1985, 75(1 Pt): 1-13.

Moscow et al., "Reduced Folate Carrier Gene (RFC1) Expression and Anti-Folate Resistance in Transfected and Non-Selected Cell Lines," International Journal of Cancer, 1997, 72: 184-190.

Mossel et al., "Exogenous ACE2 expression allows refractory cell lines to support severe acute respiratory syndrome coronavirus replication," Journal of Virology, Mar. 15, 2005, 79(6): 3846-50.

MotherToBaby, "Remdesivir (Veklury®): Fact Sheet," OTIS, May 2022, 4 pages.

Mozaffari et al., "Immunocompromised patients hospitalized for COVID-19 in the United States: evolving patient characteristics and clinical outcomes across emerging variants," Poster #LB081, Presented at European Congress of Clinical Microbiology and Infectious Diseases (ECCMID), Apr. 15-18, 2023, 1 page.

Mozaffari et al., "Remdesivir Treatment in Hospitalized Patients With Coronavirus Disease 2019 (COVID-19): A Comparative Analysis of In-hospital All-cause Mortality in a Large Multicenter Observational Cohort," Clinical Infectious Diseases, Jul. 2022, 75(1): e450-e458.

Mulangu et al., "A Randomized, Controlled Trial of Ebola Virus Disease Therapeutics," New England Journal of Medicine, Dec. 2019; 381(24): 2293-303.

Munster et al., "Hydroxychloroquine concentration-response relationships in patients with rheumatoid arthritis", Arthritis Rheumatology, Jun. 2002, 46(6): 1460-1469.

Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.

Murakami et al., "Mechanism of Activation of PSI-7851 and Its Diastereoisomer PSI-7977", The Journal of Biological Chemistry, 2010, 285(45): 34337-34347.

Murphy et al., "The Nucleoside Analog GS-441524 Strongly Inhibits Feline Infections Peritonisitis (FIP) Virus in Tissue Culture and Experimental Cat Infection Studies", Veterinary Microbiology, 2018, 219: 226-233.

Naqvi et al., "Tocilizumab and Remdesivir in a Pregnant Patient With Coronavirus Disease 2019 (COVID-19)," Obstetrics & Gynecology, Nov. 2020, 136(5): 1025-9.

Nasrallah et al., "Pharmacological treatment in pregnant women with moderate symptoms of coronavirus disease 2019 (COVID-19) pneumonia," The Journal of Maternal-Fetal & Neonatal Medicine Mar. 2021, 35(25): 5970-5977.

National Institute of Diabetes and Digestive and Kidney Diseases (NIDDK), "2009 CKD-EPI Creatinine Calculator," Chronic Kidney Disease Epidemiology Collaboration (CKD-EPI) equation, last reviewed Dec. 2022, retrieved from URL <https://www.niddk.nih.gov/health-information/professionals/clinical-tools-patient-management/kidney-disease/laboratory-evaluation/glomerular-filtration-rate-calculators/historical> 2 pages.

Neumann et al., "Hepatitis C Viral Dynamics in Vivo and the Antiviral Efficacy of Interferon-α Therapy", Science, 1998, 282: 103-107.

Nevalainen et al., "Effect of remdesivir post hospitalization for COVID-19 infection from the randomized Solidarity Finland trial," Nature Communications, Oct. 2022, 13(1): 6152.

Nguyen et al., "Favipiravir pharmacokinetics in Ebola-Infected patients of the JIKI trial reveals concentrations lower than targeted," PLoS Neglected Tropical Diseases, Feb. 2017, 11(2), 18 pages.

NIH [online], "COVID-19 Treatment Guidelines: Special Considerations During Pregnancy and After Delivery," last updated Apr. 20, 2023, retrieved from URL <https://www.covid19treatmentguidelines.nih.gov/special-populations/pregnancy/> 8 pages.

NIH [online], "Drug-Drug Interactions Between Ritonavir-Boosted Nirmatrelvir (Paxlovid) and Concomitant Medications," last updated Mar. 6, 2023, retrieved from URL <https://www.covid19treatmentguidelines.nih.gov/therapies/antivirals-including-antibody-products/ritonavir-boosted-nirmatrelvir~paxlovid-/paxlovid-drug-drug-interactions>, 8 pages.

Nilsson et al., "Discovery of 4'-azido-2'-deoxy-2'-C-methyl cytidine and prodrugs thereof: A potent inhibitor of Hepatitis C virus replication," Bioorganic & Chemistry Letters, May 2012, 22(9):3265-68.

Nishimura et al., "Synthesis of pyrrolo[2,1-f][1,2,4]triazine C-nucleosides, Isosteres of sangivamycin, tubercidin, and toyocamycin," Carbohydrate Research, 2001, 331: 77-82.

Ogura et al., "Reaction of Ethynyl Compounds with Laciones," Journal of Organic Chemistry, 1972, 37(1): 72-75.

Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.

O'Mahoney, "The prevalence and long-term health effects of Long Covid among hospitalised and non-hospitalised populations: A systematic review and meta-analysis," EClinicalMedicine, Dec. 1, 2022, 55: 1-10.

O'Toole et al., "Tracking the international spread of SARS-CoV-2 lineages B.1.1.7 and B.1.351/501Y-V2," Wellcome Open Research, May 2021, 18 pages.

Otter et al., "Conformational Properties of Purine-Like C-Nucleosides," Nucleosides & Nucleotides, 1996, 15(1-3): 793-807.

Owen et al., "An oral SARS-CoV-2 Mpro Inhibitor Clinical Candidate for the Treatment of COVID-19," Science, Nov. 2021, 374(6575): 1586-1593.

Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5): 121-133.

Ozturk et al., "Mortality analysis of COVID-19 infection in chronic kidney disease, haemodialysis and renal transplant patients compared with patients without kidney disease; a nationwide analysis from Turkey," Nephrology Dialysis Transplantation, Dec. 2020, 35(12): 2083-95.

Pagan et al., "Management of Critically Ill Pregnant Patients with COVID-19 Infection in a Rural State," American Journal of Perinatology, Jan. 2022, 39(2): 165-71.

Paharía, "Study indicates widespread SARS-CoV-2 exposure in wildlife," NewsMedical.net, Nov. 8, 2022, retrieved via Internet Archive Wayback Machine URL <https://web.archive.org/web/2022110903395S/https://www.news-medical.net/news/20221108/Study-indicates-widespread-SARS-CoV-2-exposure-in-wildlife.aspx>, 7 pages.

Pankiewicz et al., "C-Nucleoside Analogues of Nicotinamide Mononucleotide (NMN)," Nucleosides and Nucleotides, 1988 (5&6): 589-593.

(56) References Cited

OTHER PUBLICATIONS

Pankiewicz et al., "Efficient Synthesis of 5-(β-D-Ribofuranosyl)nicotinamide and its α-Isomer," Journal of Organic Chemistry, 1988, 53: 3473-3479.
Patani et al., "Bioisosterism: rational approach in drug design," Chem, Rev., 1996, 96:3147-3176.
Patel et al., "Analysis of MarketSean Data for Immunosuppressive Conditions and Hospitalizations for Acute Respiratory Illness, United States," Emerging Infectious Diseases, Apr. 29, 2020; 26(8): 1720-30.
Patil et al., "4-Aza-7,9-Dideazaadenosine, a New Cytotoxic Synthetic C-Nucleoside Analogue of Adenosine," Tetrahedron Letters, 1994, 35(30): 5339-5342.
Patil et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 1990, 9(7): 937-956.
Patil et al., "Synthesis of Pyrrolo[2,1-f][1,2,4]triazine Congenere of Nucleic Acid Purines via the N-Amination of 2-Substituted Pyrroles," J. Het. Chem., 1994, 31: 781-786.
Patil et al., "Synthesis of some new thieno[3,4-d]pyrimidines and their C-nucleosides," Journal of Heterocyclic Chemistry, 1993, 30(2): 509-515.
Peart Akindele et al., "Effect of remdesivir post-exposure prophylaxis and treatment on pathogenesis of measles in rhesus macaques," Scientific Reports, Apr. 20, 2023, 13:6463.
Pelet et al., "High throughput screening assay for negative single stranded RNA virus polymerase inhibitors," J. Virol. Methods, Sep. 2005, 128(1-2): 29-36.
Perlis et al.. "Prevalence and Correlates of Long COVID Symptoms Among US Adult," JAMA Network Open, Oct. 27, 2022; 5(10): 1-11.
Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry: 2007, 50(8):1840-1849.
Perrone et al., "First Example of Phosphoramidate: Approach Applied to a 4'-Substituted Porine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.
Peterson et al., "Prodrug approaches to improving the oral absorption of antivirul nucleotide analogues," Expert Opinion, Drug Deliv., 2009, 6(4): 405-420.
Piccirilli et al., "A Direct Route to 3-(D-Ribofuranosyl)pyridine Nucleosides," Helvetica Chimica Acta, 1991, 74: 397-406.
Pierce-Williams et al., "Clinical course of severe and critical coronavirus disease 2019 in hospitalized pregnancies: a United States cohort study," American Journal of Obstetrics & Gynecology MEM, Aug. 2020, 2(3): 12 pages.
Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.
Pilcer et al., "Formulation strategy and use of excipients in pulmonary drug delivery," International Journal of Pharmaceutics, Jun. 2010, 392(1-2): 1-19.
Pitts et al., "Efficacy in Multiple SARS-CoV-2 Animal Models Supports Phase 3 Dose Selection for Obeldesivir," presented at IDWeek, Boston, MA, USA, Oct. 11-15, 2023, Abstract 539.
Pitts et al., "Intravenous Delivery of GS-441524 is Efficacious in the African Green Monkey Model of SARS-CoV-2 Infection," Antiviral Rescarch, Jul. 2022, 203: 9 pages.
Pitts et al., "Remdesivir and GS-441524 Retain Antiviral Activity against Delta, Omicron, and Other Emergent SARS-CoV-2 Variants," Antimicrobial agents and chemotherapy, May 9, 2022, 66(6): 13 pages.
Pizzorno et al., "In vitro evaluation of antiviral activity of single and combined repurposable drugs against SARS-CoV-2," Antiviral Research, Sep. 2020, 181: 104878.
Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.
Porter et al., "Remdesivir (GS-5734) Is Efficacious in Cynomolgus Macaques Infected With Marburg Virus," The Journal of Infectious Diseases, Jun. 2020, 222(11): 1894-1901.
Porter et al., "Zika virus, drug discovery, and student projects," ScienceBlogs, Mar. 9, 2016, 7 pages.
Prasad et al., "Natural history of nonhuman primates affer oral exposure to Ebola virus variant Makona," The Journal of Infectious Diseases, Jun. 2023, 22 pages.
Prasad et al., "Resistance of Cynomolgus Monkeys to Nipah and Hendra Virus Disease Is Associated With Cell-Mediated and Humoral Immunity," The Journal of Infectious Diseases, May 2020, 221(Suppl; 4): 5436-447.
Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940): 1-16.
Puech et al., "Intracellular Delivery of Nucleoside Monophosphates through a Reductase-mediated Activation Process," Antiviral Research, 1993, 22(4): 155-174.
Radoshitzky et al., "Expanded profiling of Remdesivir as a broad-spectrum antiviral and low potential for interaction with other medications in vitro," Scientific Reports, Feb. 23, 2023, 13:3131.
Rahim et al., "Postexposure Protective Efficacy of T-705 (Favipiravir) Against Sudan Virus Infection in Guinea Pigs," The Journal of Infectious Diseases, Jul. 2018, 218(Suppl. 5): S649-S657.
Rajme-Lopez et al., "Early Outpatient Treatment With Remdesivir in Patients at High Risk for Severe COVID-19: A Prospective Cohort Study," Open Forum Infectious Diseases, Oct. 6, 2022, 9(10): 1-6.
Ramasamy et al., "Synthesis and Antitumor Activity of Certain 3-B-D-Ribofurunosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.
Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.
Rasmussen et al., "Nucleoside analog GS-441524: pharmacokinetics in different species, safety, and potential effectiveness against Covid-19," Pharmacol. Res. Perspect., Apr. 2022, 10(2):e00945.
Rebeaud et al., "SARS-CoV-2 and the Use of Chloroquine as an Antiviral Treatment," Frontiers in Medicine, Apr. 24, 2020, 7: 184, 6 pages.
Reddy et al., "Stereoselective Synthesis of Nucleoside Monophosphate HepDirectTM Prodrugs," Tet. Lett., 2005, 46: 4321-4324.
Remington's Pharmaceutical Science, 17th ed., Gennaro (ed)., 1985, Chapter 68, 58 pages.
Rodriguez et al., "Remdesivir Retains Potent Activity Against SARS-CoV-2 Variants of Concern," Poster #562, poster presented at: Conference on Retroviruses and Opportunistic Infections (CROI), Feb. 19-22, 2023, 1 page.
Ronco et al., "Kidney Involvement in COVID-19 and Rationale for Extracorporeal Therapies," Nature Reviews Nephrology, Apr. 2020, 16: 308-310.
Rosner-Tenerowicz et al. "Placental pathology in a pregnant woman with severe COVID-19 and successful ECMO treatment: a case report," BMC Pregnancy and Childbirth, Nov. 2021, 21: 760, 6 pages.
Ross et al., "Synthesis of Diastereomerically Pure Nucleotide and Phosphoramidates," J. Org. Chem., 2011, 76: 8311-8319.
Sacramento et al., "The clinically approved antiviral drug Sofosbuvir inhibits Zika Virus replication," Nature, Jan. 18, 2017, 7: 40920, 12 pages.
Sahakijpijarn et al., "Development of Remdesivir as a Dry Powder for Inhalation by Thin Film Freezing," Pharmaceutics, Oct. 2020, 12(11):1002, 27 pages.

(56) References Cited

OTHER PUBLICATIONS

Santos et al., "The REDPINE Study: Efficacy and Safety of Remdesivir in People With Moderately and Severely Reduced Kidney Function Hospitalised for COVID-19 Pneumonia," Poster #2635, Poster presented at 33rd European Congress of Clinical Microbiology and Infectios Diseases (ECCMID), Apr. 15-18, 2023, 1 page.
Saroyo et al., "Remdesivir Treatment for COVID 19 in Pregnant Patients with Moderate to Severe Symptoms: Serial Case Report," Infectious Disease Reports, May 2021, 13(2): 437-443.
Schäfer et al., "Therapeutic efficacy of an oral nucleoside analog of remdesivir against SARS-CoV-2 pathogenesis in mice," bioRxiv Preprint, Sep. 17, 2021, 36 pages.
Schäfer et al., "Therapeutic treatment with an oral prodrug of the remdesivir parental nucleoside is protective against SARS-CoV-2 pathogenesis in mice," Science Translational Medicine, May 2022, 14(643), 16 pages.
Schindell et al., "Persistence and Sexual Transmission of Filoviruses," Viruses, Dec. 2018, 10(12), 22 pages.
Schnetiler et al., "Severe acute respiratory distress syndrome in coronavirus disease 2019-infected pregnancy: obstetric and intensive care considerations," American Journal of Obstetrics & Gynecology MFM, Aug. 2020, 2(Suppl 3): 10 pages.
Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.
Schul et al., "A Dengue Fever Viremia Model in Mice : hows Reduction in Viral Replication and Suppression of the Inflammatory Response affer Treament with Antiviral Drugs," Journal of Infectious Diseases, 2007, 195: 665-674.
Schultz, "Prodrugs of Biologically Active Phosphate Esters," Bioorganic & Medicinal Chemistry; 2003.11: 885-898.
Scott et al., "Interferon-a-2b Plus Ribavirin: A Review of its Use in the Management of Chronic Hepatitis C," Drugs, 2002, 62(3): 507-556.
Sendi et al., "First-generation oral antivirals against SARS-CoV-2," Clin. Microbiol. Infect., Sep. 2022, 28(9):1230-1235.
Sheahan et al., "Broad-spectrum antiviral GS-5734 inhibits both epidemic and zoonotic coronaviruses", Science Translational Medicine, Jun. 2017, 9(396):eaal3653, 11 pages.
Sheahan et al., "Comparative therapeutic efficacy of remdesivir and combination lopinavir, ritonavir, and interferon beta against MERS-CoV," Nature Communications, 2020, 11(222): 1-14.
Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.
Shekunov et al., "Crystallization processes in pharmaceutical technology and drug delivery design," Journal of Crystal Growth, 2000, 211: 122-136.
Shetty et al., "COVID-19-Associated Glomerular Disease," Journal of the American Society of Nephrology, Jan. 2021, 32(1): 33-40.
Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):164-1652.
Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.
Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.
Silverman et al., "The Organic Chemistry of Drug Design and Drug Action," Elsevier Science, 1992, pp. 19-23.
Silverman, "The Organic Chemistry of Drug Design and Drug Action," Elsevier Science, 2nd Ed., 2004, pp. 29-34.
Singh et al., "Treatment With Remdesivir in Two Pregnant Patients With COVID-19 Pneumonia," Cureus, May 2021, 13(5): 6 pages.
Sofia et al., "Discovery of a β-d-2'-Deoxy-2'-a-fluoro-2'-β-C-methyluridine Nucleotide Prodrag (PSI-7977) for the Treatment of Hepatitis C Virus," Journal of Medicinal Chemistry, Sep. 2010, 53(19): 7202-7218.
Song et al., "Risk and Outcome of Breakthrough COVID-19 Infections in Vaccinated Patients With Cancer: Real-World Evidence From the National COVID Cohort Collaborative," Journal of Clinical Oncology, May 1, 2022, 40(13): 1414-1427.
Spinelli et al., "COVID-19 Outcomes and Risk Factors Among People Living with HIV," Current HIV/AIDS Reports, Aug. 5, 2022, 19(5): 425-32.
Spinner et al., "Effect of Remdesivir vs Standard Care on Clinical Status at 11 Days in Patients With Moderate COVID-19: A Randomized Clinical Trial," Jama, Sep. 2020, 324(11): 1048-1057.
Srivastav et al., "Antiviral Activity of Various 1-(2'-Deoxy-β-D-lyxofuranosyl), 1-(2'-Fluoro-β-D-xylofuranosyl), 1-(3'-Floor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.
Stein et al., "Phosphorylation of Nucleoside Analog Antiretrovirals: A Review for Clinicians," Pharmacotherapy, Jan. 2001, 21(1): 11-34.
Stella et al., "Cyclodextrins," Toxicologie Pathology, 2008, 36(1): 30-42.
Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.
Sun, "Remdesivir for Treatment of COVID-19: Combination of Pulmonary and IV Administration May Offer Additional Benefit", The AAPS Joumal, 2020, 22(77):1-6.
Swank et al., "Persistent Circulating Severe Acute Respiratory Syndrome Coronavirus 2 Spike Is Associated With Post-acute Coronavirus Disease 2019 Sequelae," Clinical Infectious Diseases, Sep. 2, 2022, 76(3): e487-e490.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Taki et al., "Ebanga™: The most recent FDA-approved drug for treating Ebola," Frontiers in Pharmacology, Mar. 2023, 14: 1-8.
Tan et al., "Combination Treatment With Remdesivir and Ivermectin Exerts Highly Synergistic and Potent Antiviral Activity Against Murine Coronavirus Infection," Frontiers in Cellular and Infection Microbiology, Jul. 30, 2021, 11(700503):1-10.
Tao et al., "Comparison of Anti-SARS-CoV-2 Activity and Intracellular Metabolism of Remdesivir and its Parent Nucleoside," Current Research in Pharmacology and Drug Discovery, 2021, 2, 7 pages.
Tapia et al., "Combination of a Mutagenic Agent with a Reverse Transcriptase Inhibitor Results n Systematic Inhibition of HIV-I Infection," Virology, 2005, 338: 1-8.
Taylor et al., "Neutralizing Monoclonal Antibodies for Treatment of COVID-19," Nature Reviews Immmmology, Apr. 2021, 21(6): 382-393.
Taylor, "Aulton's Pharmaceutics: The Design and Manufacture of Medicines; Chapter 37: Pulmonary Drug Delivery," 5th ed., Aulton et al (ed), 2018: 653-670.
The Recovery Collaborative Group, "Dexamethasone in Hospitalized Patients with Covid-19," New England Journal of Medicine, Feb. 2020, 384(8): 693-704.
Thi et al., "Rescue of non-human primates from advanced Sudan cholavirus infection with lipid encapsulated siRNA," Nature Microbiology, Aug. 2016, 1: 16142, 21 pages.
Tong, "Gilead quashes microcap biotech's hope of partnering on oral Covid-19 drug," Endpoint News, Jan. 31, 2023, 2 pages.
Totura et al., "Broad-spectrum coronavirus antiviral drug discovery", Expert Opinion on Drug Discovery, Mar. 2019, 17 pages.

(56) References Cited

OTHER PUBLICATIONS

Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inhibition of coronavirus RNA-dependent RNA polymerase by remdesivir reveals a second mechanism of action," J. Biol. Chem., 2020, 295(47): 16156-16165.
U.S. Department of Agriculture (USDA) [online], "Confirmed Cases of SARS-CoV-2 in Animals in the United States," last updated Aug. 29, 2023, retrieved on Aug. 29, 2023, retrieved from URL: <https://www.aphis.usda.gov/aphis/dashboards/tableau/sars-dashboard>, 1 page.
U.S. Department of Health and Human Services (HHS) [online], "Most common forms based on Pango lineage designations," last updated Aug. 25, 2023, retrieved on Aug. 29, 2023, retrieved from URL: <https://cov.lanl.gov/components&sequence/COV/pangocommonforms.comp>, 264 pages.
U.S. Food and Drug Administration (FDA), "First FDA-approved vaccine for the prevention of Ebola virus disease, marking a critical milestone in public health preparedness and response," Press Release, Dec. 19, 2019, 3 pages.
U.S. Food and Drug Administration (FDA), "Regulatory Classification of Pharmaceutical Co-Crystals Guidance for Industry," U.S. Department of Health and Human Services, Center for Drug Evaluation and Research (CDER), Feb. 2018, 7 pages.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.
Vandesompele et al., "Accurate normalization of real-time quantitative RT-PCR data by geometric averaging of multiple internal control genes," Genome Biology, Jun. 2002, 3(7): 1-12.
Vangeel et al., "Remdesivir, Molnupiravir and Nirmatrelvir remain active against SARS-CoV-2 Omicron and other variants of concern," Antiviral Research, Jan. 2022, 198: 3 pages.
Venkatachalam et al., "Effect of change in nucleoside structure on the activation and antiviral activity of phosphoramidate derivatives," Bioorganic & Medicinal Chemistry, 2005, 13: 5408-5423.
Vermillion et al., "Inhaled remdesivir reduces viral burden in a nonbuman primate model of SARS-CoV-2 infection," Science Translational Medicine, Dec. 2021, 20 pages.
Vieira et al., "Development of a Large-Scale Cyanation Process Using Continuous Flow Chemistry En Route to the Synthesis of Remdesivir," Organic Process Research & Development, May 2020, 24(10):2113-2121.
Vkovski et al., "Coronavirus Biology and Replication: Implications for SARS-CoV-2," Nature Reviews Microbiology, Oct. 2021, 19(3): 155-170.
Walker et al., "Plasma chloroquine and desethylchloroquine concentrations in children during and after chloroquine treatment for malaria.", British Journal Clinical Pharmacology, Dec. 1983, 16(6): 701-705.
Wang et al., "Analyses of Risk, Racial Disparity, and Outcomes Among US Patients With Cancer and COVID-19 Infection," JAMA Oncology, Dec. 10, 2021, 7(2): 220-227.
Wang et al., "Annovar: functional annotation of genetic variants from high-throughput sequencing data," Nucleic Acids Research, 2010 ,38(16): e164, 7 pages.
Wang et al., "Preclinical Pharmacokinetics and In Vitro Properties of GS-441524, a Potential Oral Drug Candidate for COVID-19 Treatment," Frontiers in Pharmacology, Aug. 2022, 13: 16 pages.
Wang et al., "Remdesivir and chloroquine effectively inhibit the recently emerged novel coronavirus (2019-nCoV) in vitro", Cell Research, 2020, 30: 269-271.
Wang et al., "Remdesivir in adults with severe COVID-19: a randomised, double-blind, placebo-controlled, multicentre trial," Lancet, Apr. 29, 2020, 395: 1569-1578.
Warfield et al., "Homologous and heterologous protection of non-human primates by Ebola and Sudan virus-like particles," PLoS One, Mar. 2015, 100(3): 16 pages.
Warren et al., "Protection against filovirus diseases by a novel broad-spectrum nucleoside analogue BCX4430", Nature, Apr. 2014, 508(7496): 402-405.
Warren et al., "Therapeutic efficacy of the small molecules GS-5734 against Ebola virus in rhesus monkeys", Nature, Mar. 17, 2016, 531(7594): 381-385.
Wee et al., "Development of a Human Antibody Cocktail that Deploya Multiple Functions to Confer Pan Ebolavirus Protection," Cell Host Microbe, Jan. 2019, 25(1): 39-48, e1-e5.
Wei et al., "Potency and Pharmacokinetics of GS-441524 Derivatives Against SARS-CoV-2," Bioorganic & Medicinal Chemistry, Sep. 2021, 46: 12 pages.
Williamson et al., "Factors associated with COVID-19-related death using OpenSafely," Nature, Aug. 2020, 584(7821): 430-6.
Wohl et al., "Post-Ebola Symptoms 7 Years After Infection: The Natural History of Long Ebola," Clinical Infections Diseases, Feb. 2023, 76(3): 835-840.
Wolfel et al., "Virological sessment of hospitalized patients with COVID-2019," Nature, Apr. 2020, 581: 465-470.
Woolsey et al., "A highly attenuated pan-filovirus VesiculoVax vaccine rapidly protects nonhuman primates against Marburg virus and three species of Ebolavirus," The Journal of Infectious Diseases, May 2023, 20 pages.
Woolsey et al., "A highly attenuated Vesiculovax vaccine rapidly protects nonhuman primates against lethal Marburg virus challenge," PLoS Neglected Tropical Diseases, May 2022, 16(5), 27 pages.
Woolsey et al., "Bundibugyo ebolavirus Survival Is Associated with Early Activation of Adaptive Immunity and Reduced Myeloid-Derived Suppressor Cell Signaling," mBio, Aug. 2021, 12(4), 20 pages.
Woolsey et al., "Natural history of Sudan ebolavirus infection in rhesus and cynomolgus macaques," Emerging Microbes & Infections, Jun. 2022, 11(1): 1635-46.
World Health Organization (WHO) [online], "A clinical case definition of post COVID-19 condition by a Delphi consensus," Oct. 6, 2021, retrieved from URL <https://www.who.int/publications/i/item/WHO-2019-nCOV-Post_COVID-19_condition-Clinical_case_definition-2021.1> 27 pages.
World Health Organization (WHO) [online], "Clinical management of COVID-19: living guideline," Jan. 12, 2023, retrieved from URL <https://app.magicapp.org/#/guideline/jIWBYn>, 183 pages.
World Health Organization (WHO) [online], "Post COVID-19 condition (Long COVID)," Dec. 7, 2022, retrieved from URL <https://www.who.int/europe/news-room/fact-sheets/item/post-covid-19-condition>, 2 pages.
World Health Organization (WHO) [online], "Therapeutics and COVID-19: Living Guideline," Jul. 14, 2022, updated Jan. 13, 2023, retrieved from URL <https://www.who.int/publications/i/item/WHO-2019-nCoV-therapeutics-2022.4>, 142 pages.
World Health Organization (WHO) [online], "Tracking SARS-CoV-2 variants," last updated Aug. 17, 2023, retrieved on Aug. 25, 2023, retrieved from URL <https://www.who.int/en/activities/tracking-SARS-CoV-2-variants>, 11 pages.
World Health Organization (WHO), "Ebola haemorrbagie fever in Zaire, 1976: Report of an International Commission," Bulletin of the World Health Organization, 1978, 56(2): 271-293.
World Health Organization (WHO), "Updated working definitions and primary actions for SARS-CoV-2 variants," Aug. 17, 2023, 4 pages.
World Health Organization (WHO), "WHO Coronavirus (COVID-19) Dashboard," 2020, retrieved on Oct. 19, 2023, retrieved from URL <https://covid19.who.int/>, 1 page.
World Organisation for Animal Health, "SARS CoV-2 in Animals—Situation Report 22," Jun. 30, 2023, 3 pages.
Wu et al., "AKI and Collapsing Glomeralopathy Associated with COVID-19 and APOL1 High-Risk Genotype," Journal of the American Society of Nephrology, Aug. 2020, 31(8):1688-95.
Wu et al., "Synthetic Methodologies for C-Nucleosides," Synthesis, 2004, 10: 1533-1553.
Xie et al., "A nanoluciferase SARS-CoV-2 for rapid neutralization testing and screening of anti-infective dnigs for COVID-19," Nature Communications, Oct. 15, 2020, 11(1):1-11.

(56) References Cited

OTHER PUBLICATIONS

Xie et al., "Engineering SARS-CoV-2 using a reverse genetic system," Nature protocols, Jan. 29, 2021, 16(3): 1761-1784.
Xie et al., "Long-term cardiovascular outcomes of COVID-19," Nature Medicine, Mar. 2022, 28(3): 583-90.
Xie et al., "Weinreb Amide Approach to the Practical Synthesis of a Key Remdesivir Intermediate," The Journal of Organic Chemistry, 2021, 86:5065-8072.
Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.
Yamamoto et al., "High-Dose Corticosteroids for a Pregnant Woman Critically Ill With Coronavirus Disease 2019," Cureus, Aug. 2021, 13(8): 5 pages.
Yamanaka et al., "Metabolic Studies on BMS-200475, a New Antiviral Compound Active against Hepatitis B Virus," Antimicrobial Agents and Chemotherapy, 1999, p. 43(1): 190.
Yan et al., "Advantages of the Parent Nucleoside GS-441524 over Remdesivir for Covid-19 Treatment," ACS Medicinal Chemistry Letters, Jun. 30, 2020, 11(7):1361-1366.
Yan et al., "Gilead should ditch remdesivir and focus on its simpler and safer ancestor," STAT Health Care News, May 14, 2020, 6 pages.
Yan et al., "Pharmacokinetics of 1 Orally Administered GS-441524 in Dogs," bioRxiv Preprint, May 31, 2021, 18 pages.
Yang et al., "Biotransformation and transplacental transfer of the anti-viral remdesivir and predominant metabolite, GS-441524 in pregnant rats," EBioMedicine, Jul. 2022, 81: 11 pages.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Yates et al., "The evolution of antiviral nucleoside analogues: A review for chemists and non-chemists. PartII: Complex modifications to the nucleoside scaffold", Antiviral Research, Dec. 8, 2018, 162: 5-21.
Yoon et al., "High-throughput screening-based identification of paramyxovirus inhibitors," J. Biomol. Screen., Aug. 2008, 13(7): 591-608.
Yoshimura et al., "Synthesis and Biological Evaluation of 1'-C-Cyano-Pyrimidine Nucleosides," Nuclcosides & Nucleotides, 1996, 15(1-3): 305-324.
Youssef et al., "Brief Report: Rapid Clinical Recovery From Critical Coronavirus Disease 2019 With Respiratory Failure in a Pregnant Patient Treated With IV Vasoactive Intestinal Peptide," Critical Care Explorations, Jan. 2022, 4(1): e0607.
Zeng et al., "Identification and pathological characterization of persistent asymptomatic Ebola virus infection in rhesus monkeys," Nature Microbiology, Jul. 2017, 2(1), 11 pages.
Zhang et al., "A bacterial artificial chromosome (BAC)-vectored noninfectious replicon of SARS-CoV-2", Antiviral Research, Jan. 2021, 185(1), 9 pages.
Zhang et al., "A Practical Synthesis of (2R)-3,5-di-O-benzoyl-2-fluoro-2-C-methyl-D-ribono-y-lactone", Tetrahedron: Asymmetry, 2009, 20: 305-312.
Zhang et al., "Pharmacokinetics & Safety of Remdesivir in Renal Impairment," Poster # 083, Presented at 2022 American College of Clinical Pharmacology Annual Meeting, Sep. 11, 2022, 1 page.
Zhu et al., "A novel coronavirus from patients with pneumonia in China, 2019," New England Journal of Medicine, Jan. 24, 2020, 14 pages.
PCT International Search Report and Written Opinion in International Appln. No. PCT/US2023/026612, dated Sep. 15, 2023, 15 pages.
U.S. Appl. No. 18/879,491, filed May 20, 2020, Richard L. Mackman.
Berge et al., "Pharmaceutical Salts," Journal of Pharmaceutical Sciences, Jan. 1977, 66(1):1-19.
Gareava et al., "Synthesis of Modified Purine Ribonucleosides from 3'(5')-O-Succinyladenosine and 5'-Amino-5'-deoxyadenosine," Bioorganicheskaya Khimiya, Jan. 1995, 21(9):717-723 (with English Abstract).
Kern, "In vitro activity of potential anti-poxvirus agents," Antiviral Research, Jan. 2003, 57(1-2):35-40.
Kumar et al., "An overview of automated systems relevant in pharmaceutical salt screening," Drug Discovery Today, Nov. 29, 2007, 12(23-24):1046-1053.
Mish et al., "Preparation and biological evaluation of 1'-cyano-2'-C-methyl pyrimidine nucleosides as HCV NS5B polymerase inhibitors," Bioorganic and Medicinal Chemistry Letters, Jul. 15, 2014, 24(14):3092-3095.
Nabiqasim Industries, "IVIREM Remdesivir—100mg," Product Brochure, 2020, 4 pages.
Nakanga, Wisdom P., et al. "Prevalence of impaired renal function among rural and urban populations: findings of a cross-sectional study in Malawi." Wellcome open research 4 (2019).
Rajsri et al., "Poxvirus-driven human diseases and emerging therapeutics," Therapeutic Advances in Infectious Disease, Nov. 14, 2022, 9:20499361221136751, 18 pages.
Wang et al., "Evaluation of the efficacy and safety of intravenous remdesivir in adult patients with severe COVID-19: study protocol for a phase 3 randomized, double-blind, placebo-controlled, multicentre trial," Trials, May 24, 2020, 21(1):422, 11 pages.
wmic.wales.nhs.uk, "Evidence Summary: Antiviral treatment options for human monkeypox infection," Jun. 1, 2022, retrieved on Mar. 4, 2024, retrieved from URL<https://www.wmic.wales.nhs.uk/wp-content/uploads/2022/06/Evidence-Summary-Table-final.pdf>, 6 pages.
U.S. Appl. No. 13/813,886, filed Jun. 25, 2013, Acsop Cho.
U.S. Appl. No. 18/215,881, filed Jun. 29, 2023, Kassibla E. Dempah.
"Medical Microbiology," Fourth Edition, Baron (ed.), University of Texas Medical Branch at Galveston, 1996, Chapters 59 and 72, 38 pages.
"Molecular Nuclear Medicine," Second Edition, Wang (ed.), Union Medical College of China, 2004, pp. 417-419 (with English translation).
Beaucourt et al., "Ribavirin: a drug active against many viruses with multiple effects on virus replication and propagation. Molecular basis of ribavirin resistance," Current Opinions in Virology, May 2014, 8:10-15.
Choe et al., "Exploration for the effect of renal function and renal replacement therapy on pharmacokinetics of remdesivir and GS-441524 in patients with COVID-19: A limited case series," Clinical and Translational Science, Nov. 20, 2021, 15(3):732-740.
Food and Drug Administration (FDA), "Fact Sheet for Healthcare Providers: Emergency Use Authorization for Paxlovid," FDA Emergency Use Authorization, published Dec. 2021, revised Feb. 2023, 36 pages.
Harbeson et al., "Deuterium in Drug Discovery and Development," Annual Reports in Medicinal Chemistry, Dec. 31, 2011, 46:403-417.
McGuigan et al., "Application of Phosphoramidate Pronucleotide Technology to Abacavir Leads to a Significant Enhancement of Antiviral Potency", J. Med. Chem. 2005, 48(10):3504-3515.
Ssentongo et al., BMC Infectious Diseases, "SARS-CoV-2 vaccine effectiveness against infection, symptomatic and severe COVID-19: a systematic review and meat-analysis", vol. 22, Article 439, 2022. (Year: 2022).
US Department of Health and Human Services [online] , "What is Long COVID?" retrieved on Jul. 24, 2023, retrieved from URL <https://www.covid.gov/longcovid/definitions>, 2 pages.
Eyer et al., "Nucleoside analogs as a rich source of antiviral agents active against arthropod-borne flaviviruses," Antiviral Chemistry and Chemotherapy, Mar. 2018, 26:1-28.
Gudmundsdottir et al., "Intranasal administration of midazolam in a cyclodextrin based formulation: bioavailability and clinical evaluation in humans," Pharmazie, Dec. 2001, 56(12):963-6.
Korn et al., "Dose optimization during drug development: whether and when to optimize," JNCI: Journal of the National Cancer Institute, May 1, 2023, 115(5):492-7.
Leyssen et al., "The predominant mechanism by which ribavirin exerts its antiviral activity in vitro against flaviviruses and

(56) References Cited

OTHER PUBLICATIONS paramyxoviruses is mediated by inhibition of IMP dehydrogenase," Journal of Virology, Feb. 1, 2005, 79(3):1943-7.
Li et al., "Chemical stability of 4'-azidocytidine and its prodrug balapiravir," Drug Development and Industrial Pharmacy, 2010, 36(4):413-420.
Maag, "Overcoming poor permeability—the role of prodrugs for oral drug delivery," Drug Discovery Today: Technologies, Jun. 1, 2012, 9(2):e121-30.
Morisette et al., "High-through put crystallization: polymorphs, salts, co-crystals and solvates of pharmaceutical solids," Advanced Drug Delivery Reviews, 2004, 56:275-300.
PCT International Preliminary Report on Patentability in International Appln. No. PCT/US2023/026612, mailed on Jan. 9, 2025, 8 pages.
Pinto et al., "Beclomethasone/cyclodextrin inclusion complex for dry powder inhalation," STP pharma sciences, May 1999, 9(3):253-6.
Sekharan et al., "Selecting a stable solid form of remdesivir using microcrystal electron diffraction and crystal structure prediction," RSC Advances, 2021, 11:17408-17412.
Sofia, "Nucleotide prodrugs for HCV therapy," Antiviral Chemistry and Chemotherapy, Oct. 2011, 22(1):23-49.
Tchesnokov et al., "Template-dependent inhibition of coronavirus RNA-dependent RNA polymerase by remdesivir reveals a second mechanism of action," Journal of Biological Chemistry, Nov. 20, 2020, 295(47):16156-65.
Zeitlinger et al., "Pharmacokinetics/pharmacodynamics of antiviral agents used to treat SARS-CoV-2 and their potential interaction with drugs and other supportive measures: a comprehensive review by the PK/PD of Anti-Infectives Study Group of the European Society of Antimicrobial Agents," Clinical pharmacokinetics, Oct. 2020, 59(10):1195-216.
U.S. Appl. No. 13/189,373, filed Jul. 22, 2011, Richard L. Mackman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 19/400,517, filed Nov. 25, 2025, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.
U.S. Appl. No. 18/128,850, filed Mar. 30, 2023, Tomas Cihlar.
U.S. Appl. No. 18/540,002, filed Dec. 14, 2023, Tomas Cihlar.
U.S. Appl. No. 18/791,542, filed Aug. 1, 2024, Tomas Cihlar.
U.S. Appl. No. 19/077,090, filed Mar. 12, 2025, Tomas Cihlar.
U.S. Appl. No. 17/222,125, filed Apr. 5, 2021, Scott Ellis.
U.S. Appl. No. 18/202,751, filed May 26, 2023, Scott Ellis.
U.S. Appl. No. 19/036,126, filed Jan. 24, 2025, Scott Ellis.
U.S. Appl. No. 17/158,391, filed Jan. 26, 2021, Tomas Cihlar.
U.S. Appl. No. 18/131,106, filed Apr. 5, 2023, Tomas Cihlar.
U.S. Appl. No. 18/735,429, filed Jun. 6, 2024, Tomas Cihlar.
U.S. Appl. No. 19/024,390, filed Jan. 16, 2025, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 18/655,876, filed May 6, 2024, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 18/241,303, filed Sep. 1, 2023, Nate Larson.
U.S. Appl. No. 19/057,134, filed Feb. 19, 2025, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.
U.S. Appl. No. 17/578,682, filed Jan. 19, 2022, Michel Joseph Perron.
U.S. Appl. No. 17/895,123, filed Aug. 25, 2022, Michel Joseph Perron.
U.S. Appl. No. 18/133,612, filed Apr. 12, 2023, Michel Joseph Perron.
U.S. Appl. No. 18/519,194, filed Nov. 27, 2023, Michel Joseph Perron.
U.S. Appl. No. 18/761,601, filed Jul. 2, 2024, Michel Joseph Perron.
U.S. Appl. No. 19/049,253, filed Feb. 10, 2025, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 18/673,406, filed May 24, 2024, Katrien Brak.
U.S. Appl. No. 19/011,704, filed Jan. 7, 2025, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 18/402,949, filed Jan. 3, 2024, Michael O'Neil Hanrahan Clarke.
U.S. Appl. No. 18/884,697, filed Sep. 13, 2024, Michael O'Neil Hanrahan Clarke.
U.S. Appl. No. 19/188,074, filed Apr. 24, 2025, Michael O'Neil Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 18/134,792, filed Apr. 14, 2023, Byoung Kwon Chun.
U.S. Appl. No. 18/523,984, filed Nov. 30, 2023, Byoung Kwon Chun.
U.S. Appl. No. 18/773,661, filed Jul. 16, 2024, Byoung Kwon Chun.
U.S. Appl. No. 19/059,366, filed Feb. 21, 2025, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho .
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 18/820,882, filed Aug. 30, 2024, Thomas Butler.
U.S. Appl. No. 19/178,960, filed Apr. 15, 2025, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 18/286,971, filed Oct. 13, 2023, Stacy Bremner.
U.S. Appl. No. 17/458,023, filed Aug. 26, 2021, Elaine Bunyan.
U.S. Appl. No. 18/098,950, filed Jan. 19, 2023, Elaine Bunyan.
U.S. Appl. No. 18/410,236, filed Jan. 11, 2024, Elaine Bunyan.
U.S. Appl. No. 19/174,267, filed Apr. 9, 2025, Elaine Bunyan.
U.S. Appl. No. 19/411,771, filed Dec. 8, 2025, Elaine Bunyan.
U.S. Appl. No. 18/115,895, filed Mar. 1, 2023, Rao V. Kalla.
U.S. Appl. No. 18/115,955, filed Mar. 1, 2023, Mark J. Bartlett.

(56) References Cited

OTHER PUBLICATIONS

U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 18/237,152, filed Aug. 25, 2023, Mark J. Bartlett.
U.S. Appl. No. 18/601,528, filed Mar. 11, 2024, Mark J. Bartlett.
U.S. Appl. No. 18/938,495, filed Nov. 6, 2024, Mark J. Bartlett.
U.S. Appl. No. 17/355,813, filed Jun. 23, 2021, Daniel H. Byun.
U.S. Appl. No. 18/544,561, filed Dec. 19, 2023, Daniel H. Byun.
U.S. Appl. No. 19/264,949, filed Jul. 10, 2025, Daniel H. Byun.
U.S. Appl. No. 18/205,745, filed Jun. 5, 2023, Roy Maxim Bannister.
U.S. Appl. No. 18/243,812, filed Sep. 8, 2023, Casey B. Davis.
U.S. Appl. No. 18/394,488, filed Dec. 22, 2023, Casey B. Davis.
U.S. Appl. No. 18/512,088, filed Nov. 17, 2023, John Philip Bilello.
U.S. Appl. No. 18/384,060, filed Oct. 26, 2023, Kimberly T. Barrett.
U.S. Appl. No. 18/431,038, filed Feb. 2, 2024, Kimberly T. Barrett.
U.S. Appl. No. 19/233,288, filed Apr. 10, 2025, Kimberly T. Barrett.
U.S. Appl. No. 18/215,217, filed Jun. 28, 2023, Kassibla E. Dempah.
U.S. Appl. No. 18/884,419, filed Sep. 13, 2024, Mark J. Bartlett.
U.S. Appl. No. 18/989,013, filed Dec. 20, 2024, Stefani Kocevska.
U.S. Appl. No. 18/825,549, filed Sep. 5, 2024, Kassibla E. Dempah.
U.S. Appl. No. 18/899,540, filed Sep. 27, 2024, Richard L. Mackman.
U.S. Appl. No. 18/645,671, filed Apr. 25, 2024, Mark J. Bartlett.

* cited by examiner

Figure 1. XRPD pattern of compound of Formula (I) ethanol solvate Form E1
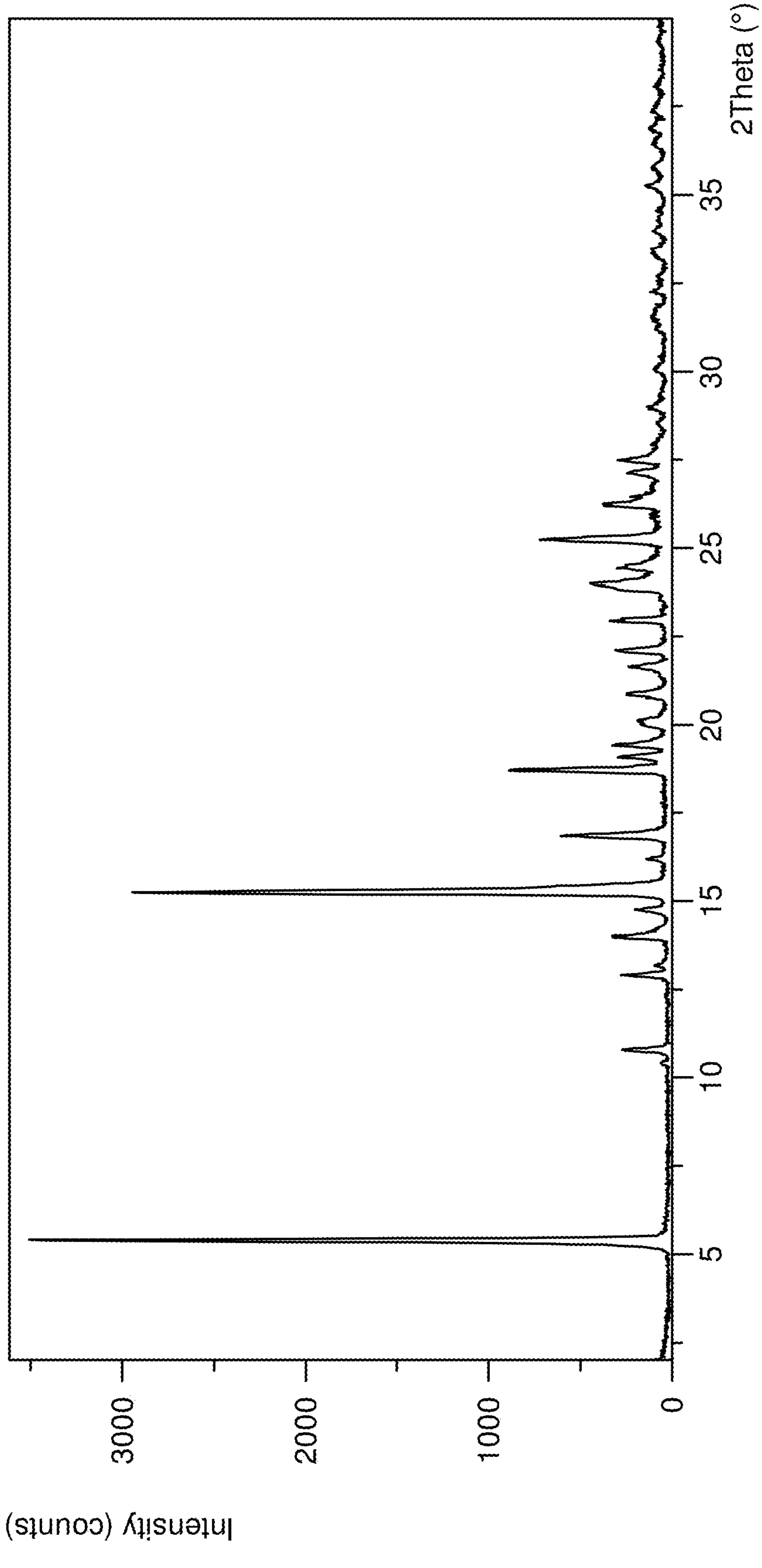

Figure 2. XRPD pattern of compound of Formula (I) Form I
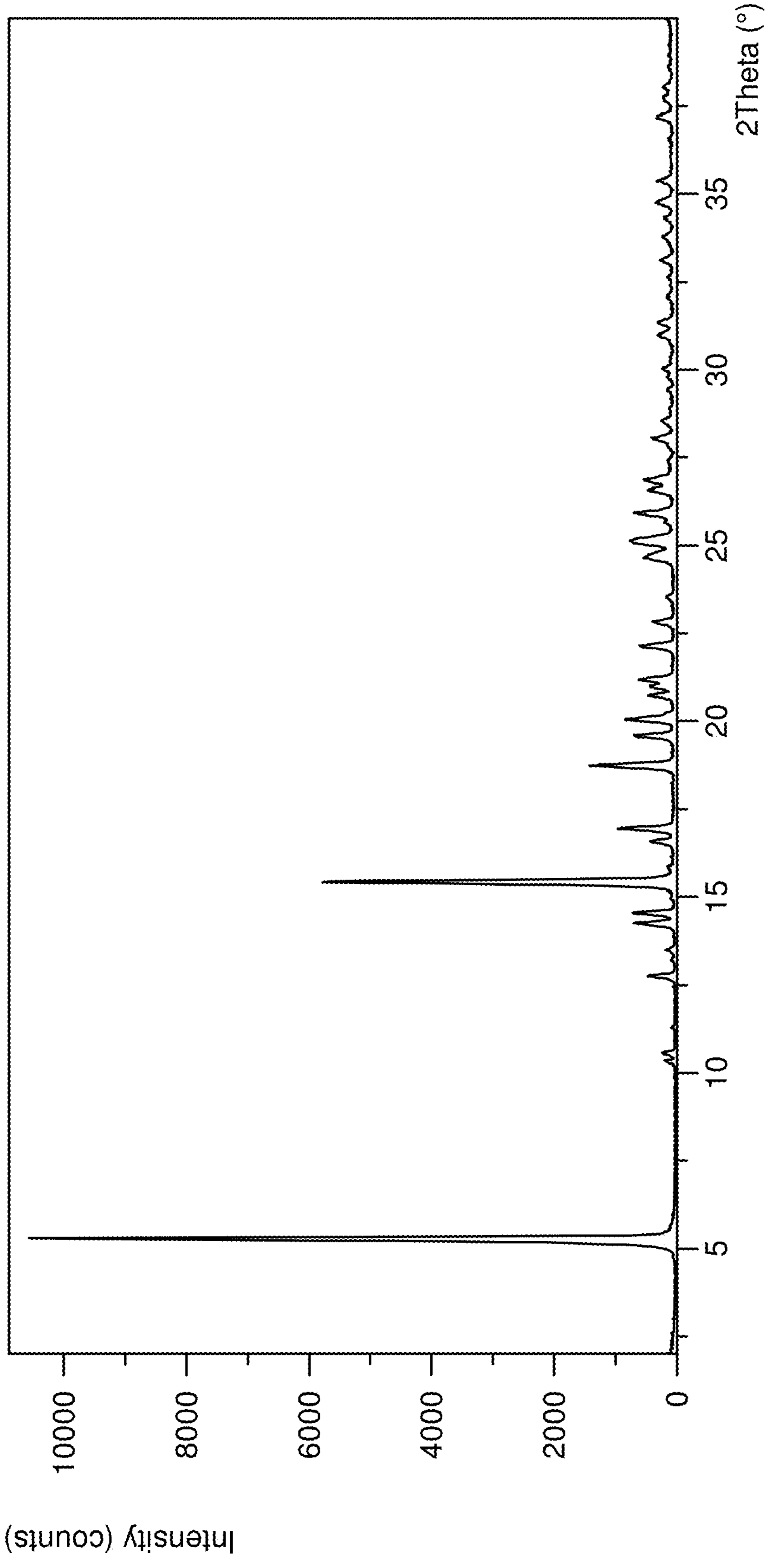

Figure 3. DSC thermogram of compound of Formula (I) Form I
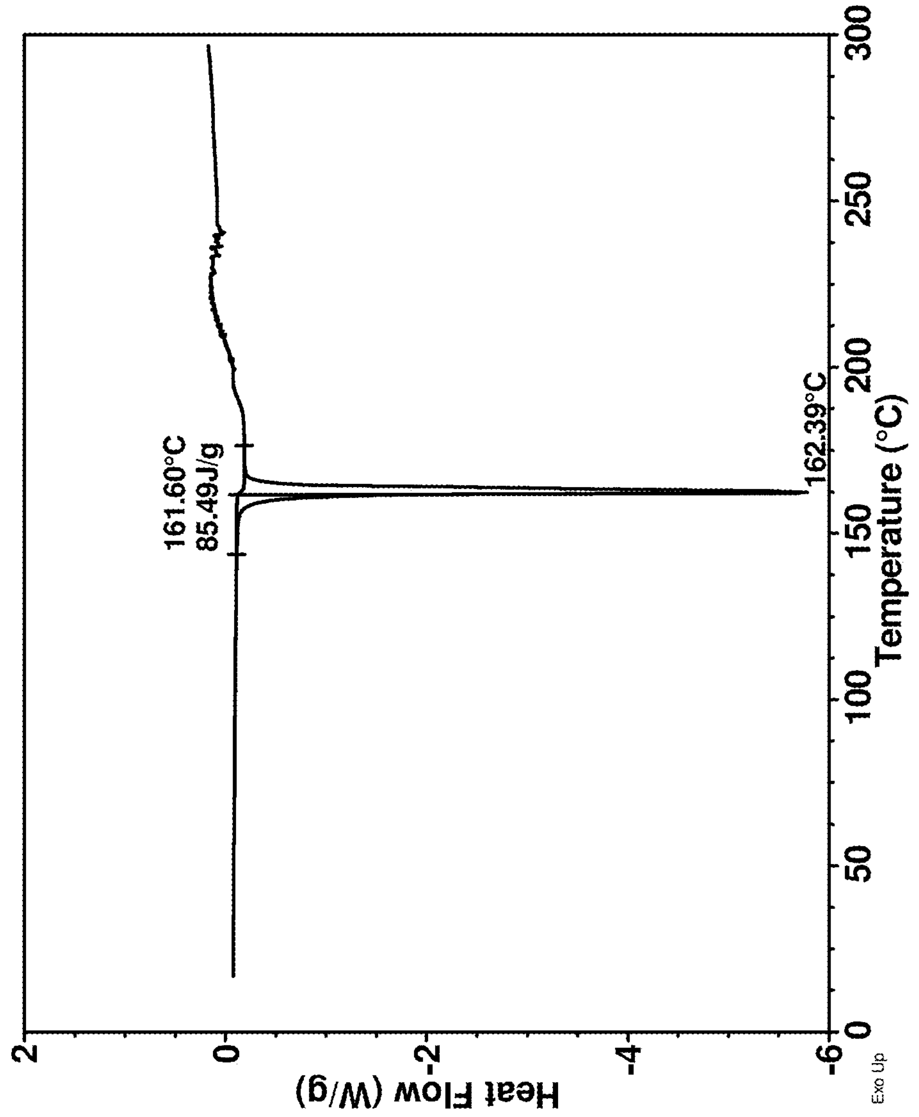

Figure 4. TGA thermogram of compound of Formula (I) Form I
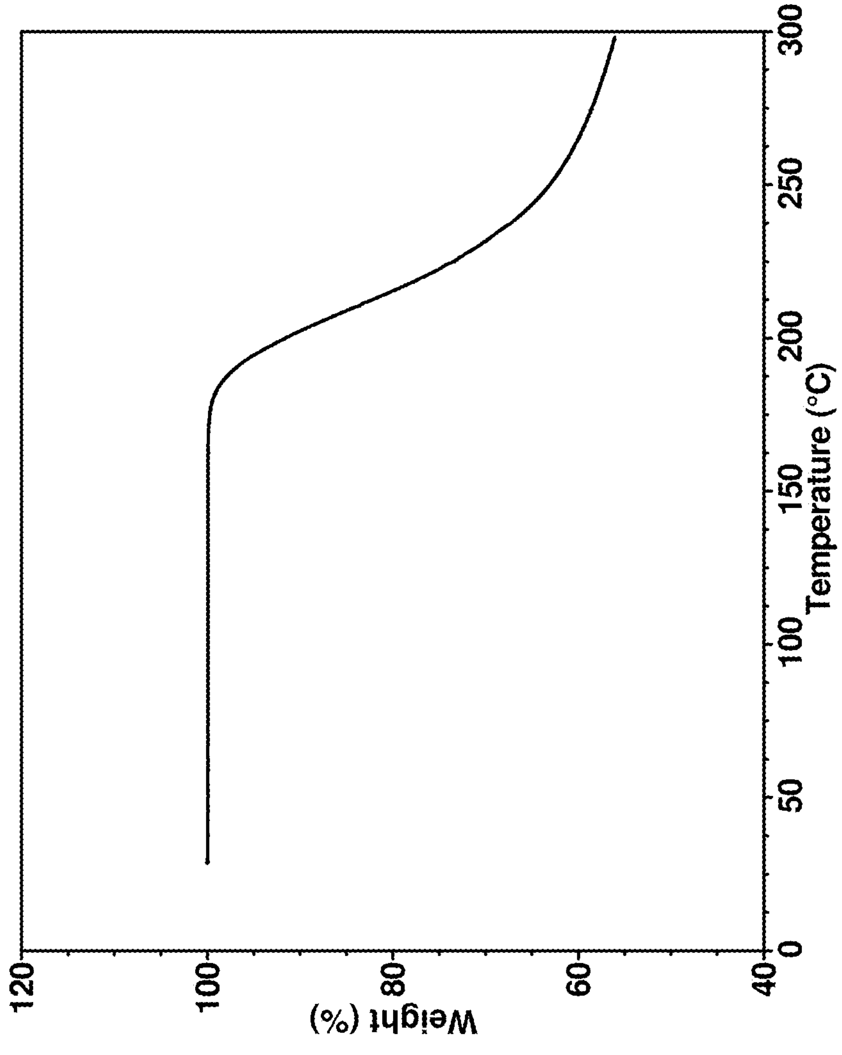

Figure 5. XRPD pattern of compound of Formula (I) acetonitrile solvate Form ACN1
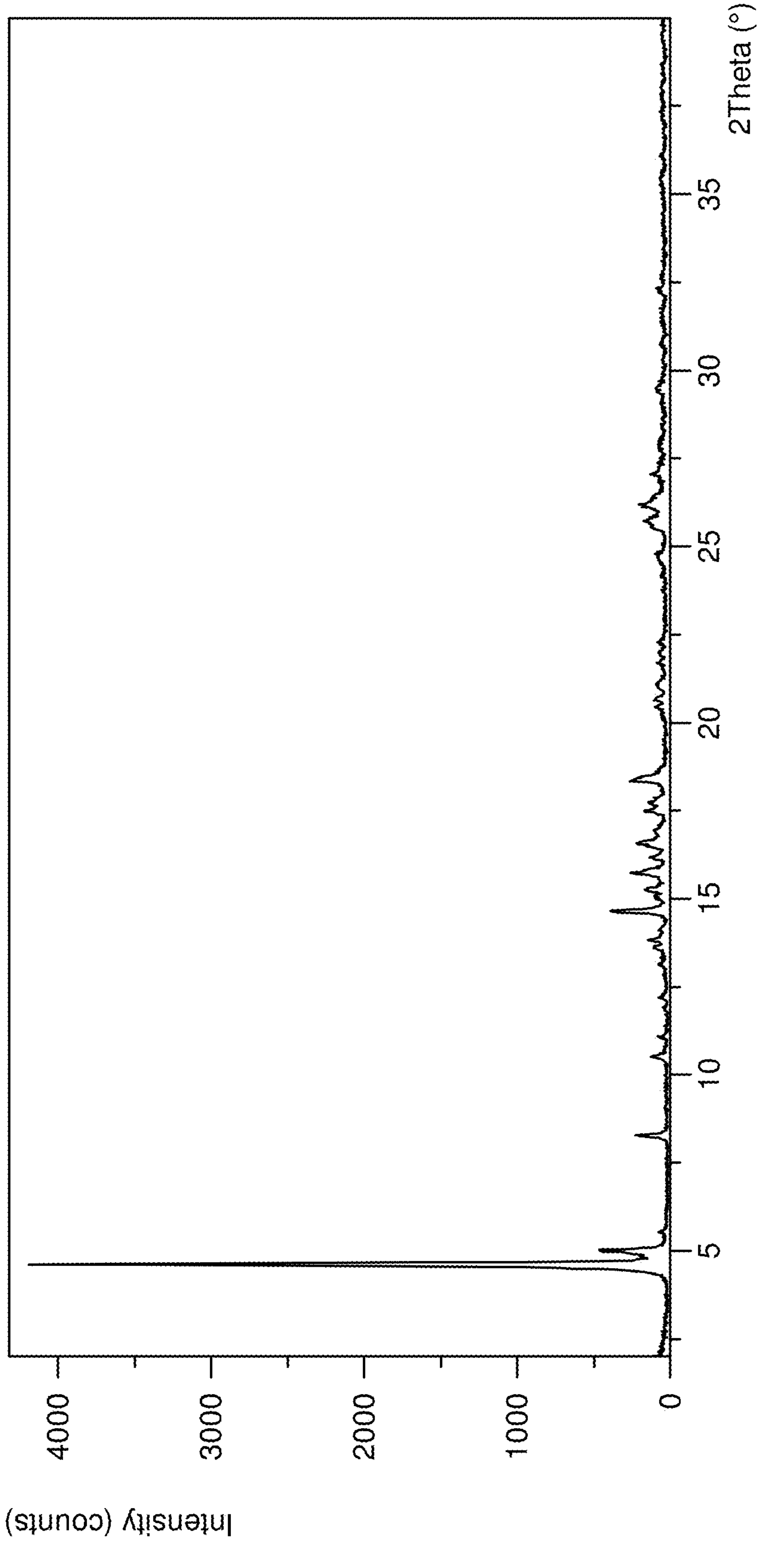

Figure 6. XRPD pattern of compound of Formula (I) Form II
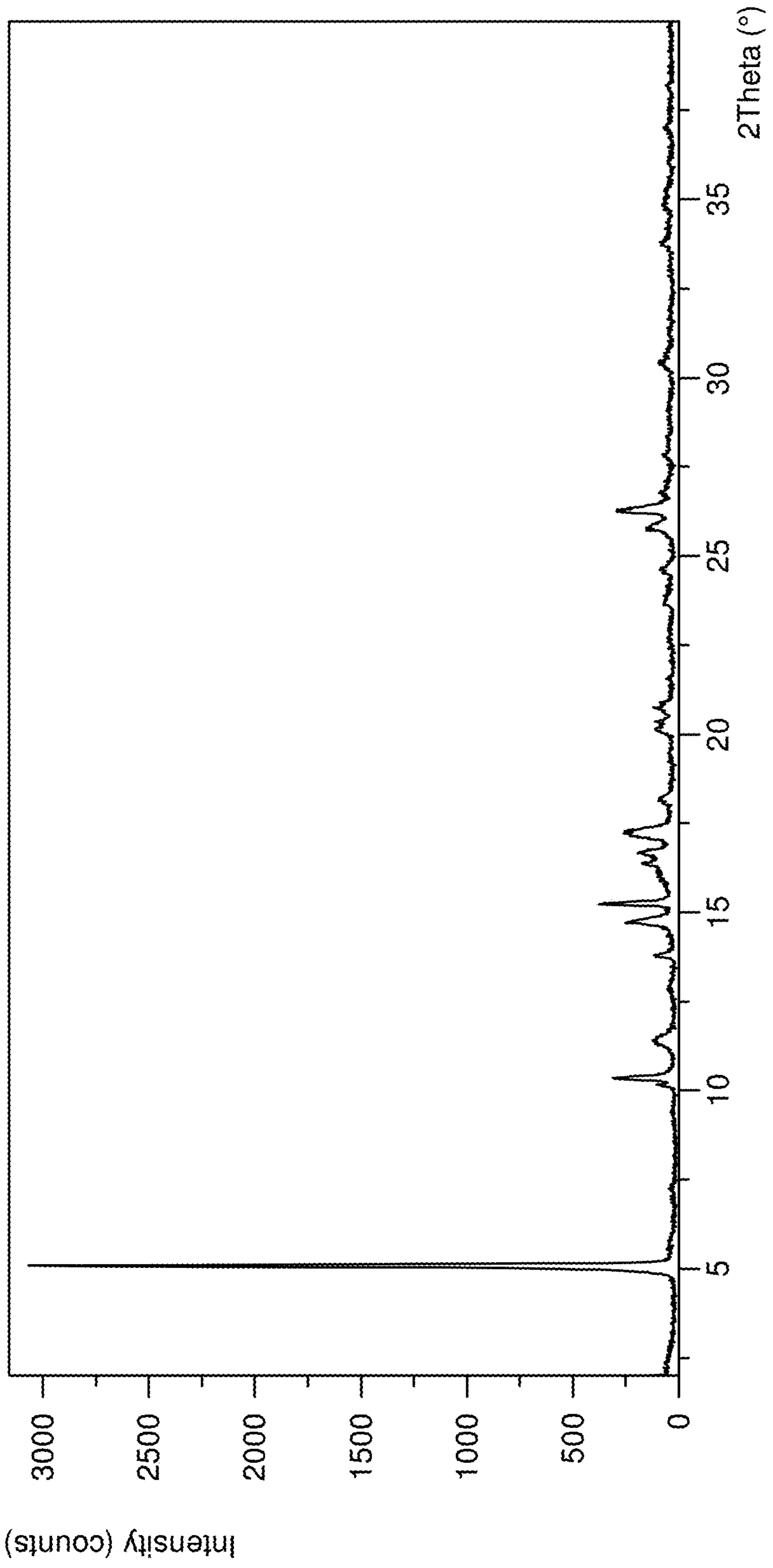

Figure 7. DSC thermogram of compound of Formula (I) Form II
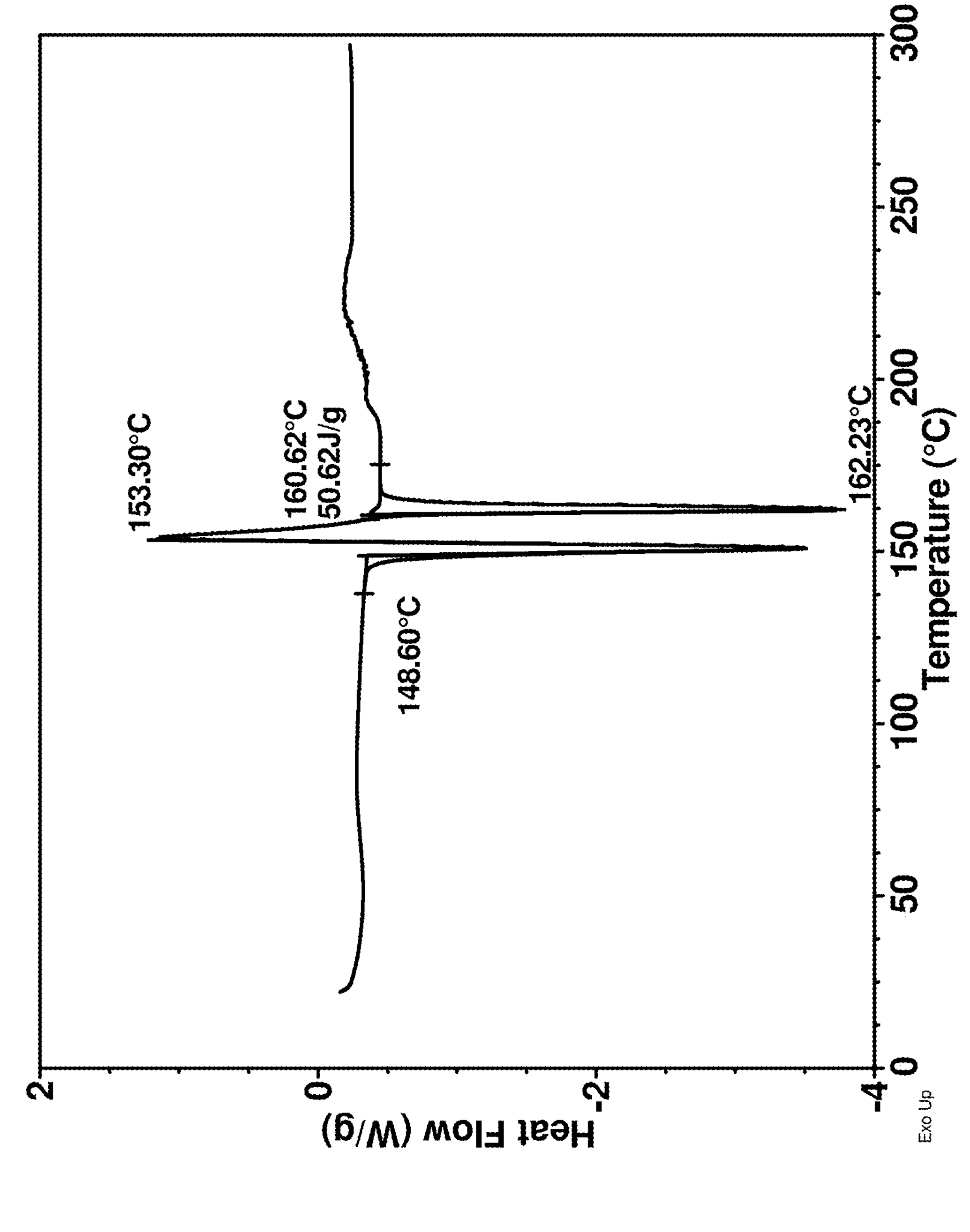

Figure 8. TGA thermogram of compound of Formula (I) Form II
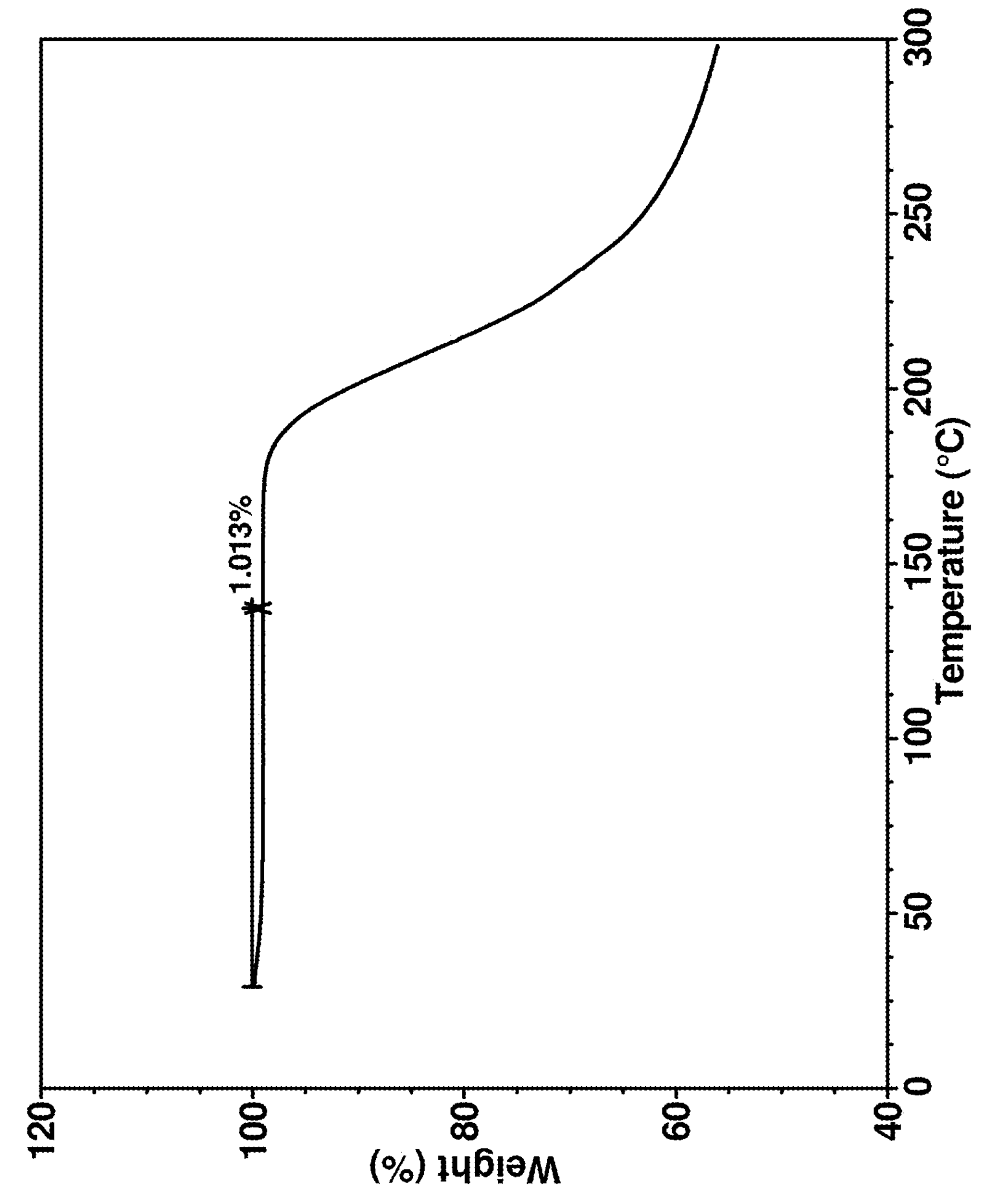

SOLID FORMS OF A NUCLEOSIDE ANALOGUE AND USES THEREOF

CROSS REFERENCE

This application claims priority to U.S. Provisional Application No. 63/357,346, filed Jun. 30, 2022, which application is incorporated herein in its entirety for all purposes.

TECHNICAL FIELD

The present disclosure relates to solid forms of ((2R,3S,4R,5R)-5-(4-aminopyrrolo[2,1-f][1,2,4]triazin-7-yl)-5-cyano-3,4-dihydroxytetrahydrofuran-2-yl)methyl neopentyl carbonate, for use in the treatment of a viral infections. The present disclosure also relates to pharmaceutical compositions comprising the solid forms disclosed herein, and methods of treating or preventing viral infections.

BACKGROUND

There is an ongoing need for antiviral agents and methods for treating viral infections, for example paramyxoviridae, pneumoviridae, picornaviridae, flaviviridae, filoviridae, arenaviridae, orthomyxovirus, and coronaviridae infections. There is also a constant need to develop methods for preparation and purification of the antiviral agents, as well as prepare improved pharmaceutical formulations of the same. The solid forms disclosed herein help meet these and other needs.

SUMMARY

The present application provides solid forms of the compound of Formula (I):

Formula (I)

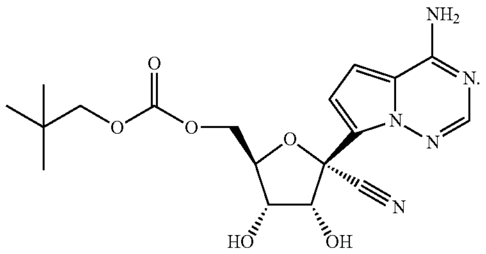

The present application further provides crystalline forms of the compound of Formula (I).

The present disclosure further provides solvates and hydrates of the compound of Formula (I), and crystalline forms thereof.

The present application further provides methods of making the solid forms disclosed herein.

The present application further provides a pharmaceutical composition comprising the solid forms disclosed herein and a pharmaceutically acceptable excipient.

The present application further provides a kit comprising the solid forms disclosed herein and a pharmaceutically acceptable excipient.

The present application further provides a method of treating or preventing a viral infection in a human in need thereof, wherein the method comprises administering to the human the solid forms or the pharmaceutical compositions disclosed herein.

The present application further provides method for manufacturing a medicament for treating or preventing a viral infection in a human in need thereof, characterized in that a crystalline form or pharmaceutical compositions disclosed herein is used.

The present application further provides use of the solid forms or pharmaceutical compositions disclosed herein for the manufacture of a medicament for the treatment or prevention of a viral infection in a human in need thereof.

The present application further provides the solid forms or pharmaceutical compositions disclosed herein for use in treatment or prevention of a viral infection in a human in need thereof.

BRIEF DESCRIPTION OF THE DRAWINGS

FIG. 1. Shows the XRPD pattern of compound of Formula (I) ethanol solvate Form E1.

FIG. 2. Shows the XRPD pattern of compound of Formula (I) Form I.

FIG. 3. Shows the DSC thermogram of compound of Formula (I) Form I.

FIG. 4. Shows the TGA thermogram of compound of Formula (I) Form I.

FIG. 5. Shows the XRPD pattern of compound of Formula (I) Acetonitrile solvate Form ACN1.

FIG. 6. Shows the XRPD pattern of compound of Formula (I) Form II.

FIG. 7. Shows the DSC thermogram of compound of Formula (I) Form II.

FIG. 8. Shows the TGA thermogram of compound of Formula (I) Form II.

DETAILED DESCRIPTION

The present disclosure relates to new solid ((2R,3S,4R,5R)-5-(4-aminopyrrolo[2,1-f][1,2,4]triazin-7-yl)-5-cyano-3,4-dihydroxytetrahydrofuran-2-yl)methyl neopentyl carbonate (i.e. the compound of Formula (I), see below). One skilled in the art understands that a compound structure may be named or identified using commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC).

Compound of Formula (I)

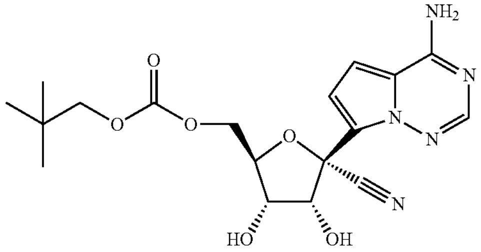

The solid forms of the invention include salt forms (both amorphous and crystalline) as well as cocrystal forms of the compound of Formula (I). As used herein, "solid form" generally refers to a solid chemical substance that can be amorphous or crystalline. In some embodiments, the solid form of the invention is a salt of compound of Formula (I) which can be amorphous or crystalline. In some embodiments, the solid form of the invention is a solvate (e.g. hydrate) of compound of Formula (I) which can be amorphous or crystalline. In further embodiments, the solid form can be a cocrystal of compound of Formula (I), in which compound of Formula (I) has formed a crystalline solid together with a coformer molecule. The crystalline salts, solvates, and cocrystals of compound of Formula (I) can exist in different crystalline forms (i.e., have different polymorphic or pseudopolymorphic forms).

As used herein, the term "cocrystal" refers to a compound (such as compound of Formula (I)) crystallized together with one or more coformer molecules (e.g., molecules other than the compound). Depending on the chemical nature and proportion of coformers present in the cocrystal, different physical properties related to, for example, dissolution and solubility may be observed compared with solid forms of the compound by itself or salts thereof. In some instances, the coformer molecule may be a protic acid, and whether the protic acid forms a salt or a cocrystal will often depend on the relative pKa's of the compound and coformer. See, e.g., *Regulatory Classification of Pharmaceutical Co-Crystals: Guidance for Industry*, revised August 2016, published by the U.S. Dept. of Health and Human Services, FDA, Center for Drug Evaluation and Research (CDER).

As used herein, "crystalline form" is meant to refer to a certain lattice configuration of a crystalline substance (e.g., a salt or a cocrystal). Different crystalline forms of the same substance typically have different crystalline lattices (e.g., unit cells) which are attributed to different physical properties that are characteristic of each of the crystalline forms. In some instances, different lattice configurations have different water or solvent content.

According to the present invention, a crystalline form of compound of Formula (I) can be useful in the synthesis and/or purification of the compound of Formula (I). For example, a crystalline form of compound of Formula (I) can be an intermediate in the synthesis of the compound 1 of Formula (I). In addition, different crystalline forms of compound of Formula (I) may have different properties with respect to bioavailability, stability, purity, and/or manufacturability for medical or pharmaceutical uses. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, the crystalline forms of compound of Formula (I) may provide advantages such as improving the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different crystalline forms of compound of Formula (I) which may exhibit one or more of the favorable characteristics described above. The processes for the preparation of the crystalline forms described herein and characterization of these crystalline and cocrystal forms are described in detail below.

In some embodiments, the crystalline forms described herein are purified or substantially isolated. By "substantially isolated" is meant that the crystalline form is at least partially or substantially separated from the environment in which it was formed or detected. Partial separation can include, for example, a composition enriched in the crystalline form of the disclosure. Substantial separation can include compositions containing at least about 50%, at least about 60%, at least about 70%, at least about 80%, at least about 90%, at least about 95%, at least about 97%, or at least about 99% by weight of the crystalline form of the disclosure. In some embodiments, the crystalline form of the disclosure can be prepared with a purity of about 75% or more, 80% or more, 85% or more, 90% or more, 95% or more, 98% or more, or 99% or more.

The different crystalline forms can be identified by solid state characterization methods such as by X-ray powder diffraction (XRPD). Other characterization methods such as differential scanning calorimetry (DSC) and thermogravimetric analysis (TGA) further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 5% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

The present invention provides crystalline forms of the compound of Formula (I). In some embodiments, the crystalline form may be substantially anhydrous. In some embodiments, the crystalline form may be hydrated or solvated.

Compound of Formula (I) Ethanol Solvate Form E1

In some embodiments, the disclosure provides solvates of the compound of Formula (I). In some embodiments, the solvate is a hydrate. In some embodiments, the solvate is an organic solvent solvate. In some embodiments, the solvate is methanol, ethanol, isopropanol, 1-butanol, 2-butanol, acetone, acetonitrile, ethyl acetate, isopropyl acetate, butyl acetate, methyl t-butyl ether (MTBE), tetrahydrofuran, toluene, 1-butanone (methyl ethyl ketone), 2-methyl tetrahydrofuran, heptane, cyclohexane, cyclopentyl methyl ether, dichloromethane, N,N-dimethylacetamide, N,N-dimethylformamide, ethyleneglycol, hexane, propylene glycol, methyl butyl ketone, methylcyclohexane, methylisobutylketone, N-methylpyrrolidone, t-butyl alcohol, acetic acid, anisole, dimethyl sulfoxide, isobutyl acetate, methyl acetate, 2-methyl-1-propanol, ethyl ether, ethyl formate, formic acid, pentane, 1-pentanol, propyl acetate, or triethylamine solvate. In some embodiments, the solvate is amorphous. In some embodiments, the solvate is crystalline.

In some embodiments, the present disclosure provides crystalline form of a solvate of the compound of Formula (I). In some embodiments, the disclosure provides crystalline form of ethanol solvate of the compound of Formula (I). In some embodiments, the crystalline form is ethanol solvate Form E1 ("ethanol solvate crystalline Form E1"). In some embodiments, ethanol solvate crystalline Form E1 has an XRPD profile substantially as shown in FIG. 1. In some embodiments, ethanol solvate crystalline Form E1 has an XRPD pattern displaying at least two, at least three, at least four, at least five, or at least six of the degree 2θ-reflections as the XRPD pattern substantially as shown in FIG. 1.

In some embodiments, the ethanol solvate crystalline Form E1 is characterized by an XRPD pattern comprising degree 2θ-reflections (±0.2 degrees 2θ) at about 5.4°, 15.2°, and 23.8°. In some embodiments, the ethanol solvate crystalline Form E1 has an XRPD pattern comprising degree 2θ-reflections (±0.2 degrees 2θ) at 5.4°, 15.2°, and 23.8°, and one, two or three of the degree 2θ-reflections (±0.2 degrees 2θ) at 12.9°, 18.7°, and 25.2°. In some embodiments, the ethanol solvate crystalline Form E1 has an XRPD pattern comprising degree 2θ-reflections (±0.2 degrees 2θ) at 5.4°, 15.2°, and 23.8°, and one or two of the degree 2θ-reflections (±0.2 degrees 2θ) at 12.9°, 18.7°, and 25.2°. In some embodiments, the ethanol solvate crystalline Form E1 has an XRPD pattern comprising degree 2θ-reflections (±0.2 degrees 2θ) at 5.4°, 15.2°, and 23.8°, and one of the degree 2θ-reflections (±0.2 degrees 2θ) at 12.9°, 18.7°, and 25.2°. In some embodiments, the ethanol solvate crystalline Form E1 has an XRPD pattern comprising degree 2θ-reflections (±0.2 degrees 2θ) at 5.4°, 15.2°, and 23.8°, and two of the degree 2θ-reflections (±0.2 degrees 2θ) at 12.9°, 18.7°, and 25.2°. In some embodiments, the ethanol solvate crystalline Form E1 has an XRPD pattern comprising degree 2θ-reflections (±0.2 degrees 2θ) at 5.4°, 12.9°, 15.2°, 18.7°, 23.8° and 25.2°. In some embodiments, the ethanol solvate crystalline Form E1 has an XRPD pattern comprising any three degree 2θ-reflections (±0.2 degrees 2θ) selected from the group consisting of 5.4°, 12.9°, 15.2°, 18.7°, 23.8° and 25.2°.

In some embodiments, the ethanol solvate crystalline Form E1 has an XRPD pattern comprising degree 2θ-reflections (±0.2 degrees 2θ) at 5.4°, 12.9°, 15.2°, 18.7°, 23.8° and 25.2°, and one, two, or three of the degree 2θ-reflections (±0.2 degrees 2θ) at 14.0°, 16.8°, and 24.0°. In some embodiments, the ethanol solvate crystalline Form E1 has an XRPD pattern comprising degree 2θ-reflections (±0.2 degrees 2θ) at 5.4°, 12.9°, 15.2°, 18.7°, 23.8° and 25.2°, and one or two of the degree 2θ-reflections (±0.2 degrees 2θ) at 14.0°, 16.8°, and 24.0°. In some embodiments, the ethanol solvate crystalline Form E1 has an XRPD pattern comprising degree 2θ-reflections (±0.2 degrees 2θ) at 5.4°, 12.9°, 15.2°, 18.7°, 23.8° and 25.2°, and one of the degree 2θ-reflections (±0.2 degrees 2θ) at 14.0°, 16.8°, and 24.0°. In some embodiments, the ethanol solvate crystalline Form E1 has an XRPD pattern comprising degree 2θ-reflections (±0.2 degrees 2θ) at 5.4°, 12.9°, 15.2°, 18.7°, 23.8° and 25.2°, and two of the degree 2θ-reflections (±0.2 degrees 2θ) at 14.0°, 16.8°, and 24.0°. In some embodiments, the ethanol solvate crystalline Form E1 has an XRPD pattern comprising degree 2θ-reflections (±0.2 degrees 2θ) at 5.4°, 12.9°, 14.0°, 15.2°, 16.8°, 18.7°, 23.8°, 24.0°, and 25.2°. In some embodiments, the ethanol solvate crystalline Form E1 has an XRPD pattern comprising three of the degree 2θ-reflections (±0.2 degrees 2θ) at 5.40, 12.90, 14.00, 15.20, 16.80, 18.70, 23.80, 24.00, and 25.20.

In some embodiments, the ethanol solvate crystalline Form E1 has a XRPD pattern comprising peaks at:

| Pos. [°2Th.] | Rel. Int. [%] |
|---|---|
| 5.4 | 100 |
| 10.4 | 1 |
| 10.8 | 7 |
| 12.9 | 6 |
| 14.0 | 7 |
| 14.8 | 5 |
| 15.2 | 81 |
| 16.2 | 3 |
| 16.8 | 15 |
| 18.7 | 25 |
| 19.1 | 7 |
| 19.4 | 8 |
| 20.0 | 3 |
| 20.1 | 4 |
| 20.9 | 6 |
| 21.6 | 6 |
| 22.1 | 8 |
| 22.9 | 8 |
| 23.8 | 7 |
| 24.0 | 12 |
| 24.4 | 7 |
| 25.2 | 19 |
| 26.2 | 9 |
| 27.1 | 6 |
| 27.5 | 7 |
| 28.5 | 1 |
| 29.0 | 2 |
| 30.0 | 1 |
| 31.6 | 2 |
| 32.3 | 2 |
| 33.4 | 2 |
| 34.0 | 1 |
| 35.3 | 3 |
| 35.8 | 2 |
| 36.4 | 1 |
| 36.9 | 2 |
| 37.4 | 1 |
| 38.1 | 1 |

Compound of Formula (I) Solvated Form ACN1

In some embodiments, the disclosure provides solvated crystalline form of the compound of Formula (I). In some embodiments, the disclosure provides acetonitrile solvate forms of the compound of Formula (I). In some embodiments, the disclosure provides acetonitrile solvate form ACN1 of the compound of Formula (I) ("crystalline Form ACN1"). In some embodiments, crystalline Form ACN1 has an XRPD profile substantially as shown in FIG. 5. In some embodiments, crystalline Form ACN1 has an XRPD pattern displaying at least two, at least three, at least four, at least five, or at least six of the degree 2θ-reflections as the XRPD pattern substantially as shown in FIG. 5.

In some embodiments, the crystalline Form ACN1 is characterized by an XRPD pattern comprising degree 2θ-reflections (±0.2 degrees 2θ) at about 4.6°, 14.6°, and 18.3°. In some embodiments, the crystalline Form ACN1 has an XRPD pattern comprising degree 2θ-reflections (±0.2 degrees 2θ) at 4.6°, 14.6°, and 18.3°, and one, two or three of the degree 2θ-reflections (±0.2 degrees 2θ) at 5.0°, 15.7°, and 26.2°. In some embodiments, the crystalline Form ACN1 has an XRPD pattern comprising degree 2θ-reflections (±0.2 degrees 2θ) at 4.6°, 14.6°, and 18.3°, and one or two of the degree 2θ-reflections (±0.2 degrees 2θ) at 5.0°, 15.7°, and 26.2°. In some embodiments, the crystalline Form ACN1 has an XRPD pattern comprising degree 2θ-reflections (±0.2 degrees 2θ) at 4.6°, 14.6°, and 18.3°, and one of the degree 2θ-reflections (±0.2 degrees 2θ) at 5.0°, 15.7°, and 26.2°. In some embodiments, the crystalline Form ACN1 has an XRPD pattern comprising degree 2θ-reflections (±0.2 degrees 2θ) at 4.6°, 14.6°, and 18.3°, and two of the degree 2θ-reflections (±0.2 degrees 2θ) at 5.0°, 15.7°, and 26.2°. In some embodiments, the crystalline Form ACN1 has an XRPD pattern comprising degree 2θ-reflections (±0.2 degrees 2θ) at 4.6°, 5.0°, 14.6°, 15.7°, 18.3°, and 26.2°. In some embodiments, the crystalline Form ACN1 has an XRPD pattern comprising any three degree 2θ-reflections (±0.2 degrees 2θ) selected from the group consisting of 4.6°, 5.0°, 14.6°, 15.7°, 18.3°, and 26.2°.

In some embodiments, the crystalline Form ACN1 has an XRPD pattern comprising degree 2θ-reflections (±0.2 degrees 2θ) at 4.6°, 5.0°, 14.6°, 15.7°, 18.3°, and 26.2°, and one, two, or three of the degree 2θ-reflections (±0.2 degrees 2θ) at 8.3°, 16.6°, and 17.5°. In some embodiments, the crystalline Form ACN1 has an XRPD pattern comprising degree 2θ-reflections (±0.2 degrees 2θ) at 4.6°, 5.0°, 14.6°, 15.7°, 18.3°, and 26.2°, and one or two of the degree 2θ-reflections (±0.2 degrees 2θ) at 8.3°, 16.6°, and 17.5°. In some embodiments, the crystalline Form ACN1 has an XRPD pattern comprising degree 2θ-reflections (±0.2 degrees 2θ) at 4.6°, 5.0°, 14.6°, 15.7°, 18.3°, and 26.2°, and one of the degree 2θ-reflections (±0.2 degrees 2θ) at 8.3°, 16.6°, and 17.5°. In some embodiments, the crystalline Form ACN1 has an XRPD pattern comprising degree 2θ-reflections (±0.2 degrees 2θ) at 4.6°, 5.0°, 14.6°, 15.7°, 18.3°, and 26.2°, and two of the degree 2θ-reflections (±0.2 degrees 2θ) at 8.3°, 16.6°, and 17.5°. In some embodiments, the crystalline Form ACN1 has an XRPD pattern comprising degree 2θ-reflections (±0.2 degrees 2θ) at 4.6°, 5.0°, 8.3°, 14.6°, 15.7°, 16.6°, 17.5°, 18.3°, and 26.2°. In some embodiments, the crystalline Form ACN1 has an XRPD pattern comprising three of the degree 2θ-reflections (±0.2 degrees 2θ) at 4.6°, 5.0°, 8.3°, 14.6°, 15.7°, 16.6°, 17.5°, 18.3°, and 26.2°.

In some embodiments, the crystalline Form ACN1 has a XRPD pattern comprising peaks at:

| Pos. [°2Th.] | Rel. Int. [%] |
|---|---|
| 4.6 | 100 |
| 5.0 | 11 |
| 5.5 | 1 |
| 8.3 | 5 |
| 10.5 | 2 |
| 11.1 | 1 |
| 12.2 | 1 |
| 13.2 | 1 |
| 13.6 | 2 |
| 13.8 | 3 |
| 14.1 | 1 |
| 14.6 | 9 |
| 15.2 | 3 |
| 15.7 | 5 |
| 16.2 | 3 |
| 16.6 | 5 |
| 16.9 | 2 |
| 17.5 | 3 |
| 17.7 | 2 |
| 18.3 | 6 |
| 20.4 | 1 |
| 20.7 | 2 |
| 21.1 | 1 |
| 21.7 | 1 |
| 22.1 | 1 |
| 22.3 | 1 |

-continued

| Pos. [°2Th.] | Rel. Int. [%] |
|---|---|
| 24.8 | 1 |
| 25.7 | 3 |
| 26.2 | 4 |
| 27.1 | 2 |
| 27.8 | 1 |
| 29.5 | 1 |
| 30.7 | 1 |
| 32.3 | 1 |
| 35.4 | 1 |

Compound of Formula (I) Form I

In some embodiments, the present disclosure provides a crystalline Form I of the compound of Formula (I) (compound of Formula (I) Form I). The compound of Formula (I) Form I exhibits an X-ray powder diffraction (XRPD) pattern substantially as shown in FIG. 2. The compound of Formula (I), Form I may exhibit a differential scanning calorimetry (DSC) thermogram substantially as shown in FIG. 3. The compound of Formula (I) Form I may exhibit a thermogravimetric analysis (TGA) graph substantially as shown in FIG. 4. The compound of Formula (I) Form I is unsolvated (i.e. free of solvent).

In some embodiments of the compound of Formula (I) Form I, at least one, at least two, at least three, or all of the following (a)-(c) apply: (a) compound of Formula (I) Form I has an XRPD pattern substantially as shown in FIG. 2; (b) compound of Formula (I) Form I has a DSC thermogram substantially as shown in FIG. 3; and (c) compound of Formula (I) Form I has a TGA graph substantially as shown in FIG. 4.

In some embodiments, compound of Formula (I) Form I has an XRPD pattern displaying at least two, at least three, at least four, at least five, or at least six of the degree 2θ-reflections as the XRPD pattern substantially as shown in FIG. 2.

In some embodiments, compound of Formula (I) Form I has an XRPD pattern comprising degree 2θ-reflections (±0.2 degrees 2θ) at 5.3°, 18.7°, and 20.0°. In some embodiments, compound of Formula (I) Form I has an XRPD pattern comprising degree 2θ-reflections (±0.2 degrees 2θ) at 5.3°, 18.7°, and 20.0°, and one, two or three of the degree 2θ-reflections (±0.2 degrees 2θ) at 14.3°, 15.4°, and 25.1°. In some embodiments, compound of Formula (I) Form I has an XRPD pattern comprising degree 2θ-reflections (±0.2 degrees 2θ) at 5.3°, 18.7°, and 20.0°, and one or two of the degree 2θ-reflections (±0.2 degrees 2θ) at 14.3°, 15.4°, and 25.1°. In some embodiments, compound of Formula (I) Form I has an XRPD pattern comprising degree 2θ-reflections (±0.2 degrees 2θ) at 5.3°, 18.7°, and 20.0°, and one of the degree 2θ-reflections (±0.2 degrees 2θ) at 14.3°, 15.4°, and 25.1°. In some embodiments, compound of Formula (I) Form I has an XRPD pattern comprising degree 2θ-reflections (±0.2 degrees 2θ) at 5.3°, 18.7°, and 20.0°, and two of the degree 2θ-reflections (±0.2 degrees 2θ) at 14.3°, 15.4°, and 25.1°. In some embodiments, compound of Formula (I) Form I has an XRPD pattern comprising degree 2θ-reflections (±0.2 degrees 2θ) at 5.3°, 14.3°, 15.4°, 18.7°, 20.0°, and 25.1°. In some embodiments, compound of Formula (I) Form I has an XRPD pattern comprising any three degree 2θ-reflections (±0.2 degrees 2θ) selected from the group consisting of 5.3°, 14.3°, 15.4°, 18.7°, 20.0°, and 25.1°.

In some embodiments, compound of Formula (I) Form I has an XRPD pattern comprising degree 2θ-reflections (±0.2 degrees 2θ) at 5.3°, 14.3°, 15.4°, 18.7°, 20.0°, and 25.10, and one, two, or three of the degree 2θ-reflections (±0.2 degrees 2θ) at 14.6°, 17.0°, and 25.9°. In some embodiments, compound of Formula (I) Form I has an XRPD pattern comprising degree 2θ-reflections (±0.2 degrees 2θ) at 5.3°, 14.3°, 15.4°, 18.7°, 20.0°, and 25.10, and one or two of the degree 2θ-reflections (±0.2 degrees 2θ) at 14.6°, 17.0°, and 25.9°. In some embodiments, compound of Formula (I) Form I has an XRPD pattern comprising degree 2θ-reflections (±0.2 degrees 2θ) at 5.3°, 14.3°, 15.4°, 18.7°, 20.0°, and 25.10, and one of the degree 2θ-reflections (±0.2 degrees 2θ) at 14.6°, 17.0°, and 25.9°. In some embodiments, compound of Formula (I) Form I has an XRPD pattern comprising degree 2θ-reflections (±0.2 degrees 2θ) at 5.3°, 14.3°, 15.4°, 18.7°, 20.0°, and 25.10, and two of the degree 2θ-reflections (±0.2 degrees 2θ) at 14.6°, 17.0°, and 25.9°. In some embodiments, compound of Formula (I) Form I has an XRPD pattern comprising degree 2θ-reflections (±0.2 degrees 2θ) at 5.3°, 14.3°, 14.6°, 15.4°, 17.0°, 18.7°, 20.0°, 25.10, and 25.9°. In some embodiments, compound of Formula (I) Form I has an XRPD pattern comprising three of the degree 2θ-reflections (±0.2 degrees 2θ) at 5.3°, 14.3°, 14.6°, 15.4°, 17.0°, 18.7°, 20.0°, 25.1°, and 25.9°.

In some embodiments, compound of Formula (I) Form I has a XRPD pattern comprising peaks at:

| Pos. [°2Th.] | Rel. Int. [%] |
|---|---|
| 5.3 | 100 |
| 10.3 | 1 |
| 10.6 | 2 |
| 12.8 | 4 |
| 13.2 | 1 |
| 13.5 | 1 |
| 14.3 | 6 |
| 14.6 | 6 |
| 15.4 | 54 |
| 15.8 | 1 |
| 16.6 | 4 |
| 17.0 | 9 |
| 18.7 | 13 |
| 19.6 | 6 |
| 20.0 | 8 |
| 20.7 | 3 |
| 21.0 | 4 |
| 21.2 | 5 |
| 22.1 | 5 |
| 22.8 | 3 |
| 23.5 | 1 |
| 24.6 | 4 |
| 25.1 | 6 |
| 25.2 | 5 |
| 25.9 | 6 |
| 26.6 | 3 |
| 26.9 | 5 |
| 27.4 | 1 |
| 28.1 | 3 |
| 28.6 | 2 |
| 29.4 | 1 |
| 29.8 | 1 |
| 30.0 | 1 |
| 30.9 | 2 |
| 31.3 | 2 |
| 32.1 | 1 |
| 32.6 | 1 |
| 33.1 | 2 |
| 33.8 | 1 |
| 34.3 | 1 |
| 34.7 | 2 |
| 35.4 | 2 |
| 37.2 | 2 |
| 37.7 | 1 |
| 38.1 | 1 |

In some embodiments, compound of Formula (I) Form I is characterized by a DSC thermogram substantially as shown in FIG. 3.

In some embodiments, compound of Formula (I) Form I is characterized by an endothermic transition with an onset at about 162° C.

In some embodiments, compound of Formula (I) Form I is characterized by a TGA curve substantially as shown in FIG. 4. The TGA curves indicates that the compound of Formula (I) Form I is unsolvated.

Compound of Formula (I) Form II

In some embodiments, the present disclosure provides a crystalline Form II of the compound of Formula (I) (compound of Formula (I) Form II). The compound of Formula (I) Form II exhibits an X-ray powder diffraction (XRPD) pattern substantially as shown in FIG. 6. The compound of Formula (I), Form II may exhibit a differential scanning calorimetry (DSC) thermogram substantially as shown in FIG. 7. The compound of Formula (I) Form II may exhibit a thermogravimetric analysis (TGA) graph substantially as shown in FIG. 8. The compound of Formula (I) Form II is desolvated (i.e. free of solvent).

In some embodiments of the compound of Formula (I) Form II, at least one, at least two, at least three, or all of the following (a)-(c) apply: (a) compound of Formula (I) Form II has an XRPD pattern substantially as shown in FIG. 6; (b) compound of Formula (I) Form II has a DSC thermogram substantially as shown in FIG. 7; and (c) compound of Formula (I) Form II has a TGA graph substantially as shown in FIG. 8.

In some embodiments, compound of Formula (I) Form II has an XRPD pattern displaying at least two, at least three, at least four, at least five, or at least six of the degree 2θ-reflections as the XRPD pattern substantially as shown in FIG. 6.

In some embodiments, compound of Formula (I) Form II has an XRPD pattern comprising degree 2θ-reflections (±0.2 degrees 2θ) at 5.1°, 10.3°, and 15.2°. In some embodiments, compound of Formula (I) Form II has an XRPD pattern comprising degree 2θ-reflections (±0.2 degrees 2θ) at 5.1°, 10.3°, and 15.2°, and one, two or three of the degree 2θ-reflections (±0.2 degrees 2θ) at 14.7°, 17.3°, and 26.2°. In some embodiments, compound of Formula (I) Form II has an XRPD pattern comprising degree 2θ-reflections (±0.2 degrees 2θ) at 5.1°, 10.3°, and 15.2°, and one or two of the degree 2θ-reflections (±0.2 degrees 2θ) at 14.7°, 17.3°, and 26.2°. In some embodiments, compound of Formula (I) Form II has an XRPD pattern comprising degree 2θ-reflections (±0.2 degrees 2θ) at 5.1°, 10.3°, and 15.2°, and one of the degree 2θ-reflections (±0.2 degrees 2θ) at 14.7°, 17.3°, and 26.2°. In some embodiments, compound of Formula (I) Form II has an XRPD pattern comprising degree 2θ-reflections (±0.2 degrees 2θ) at 5.1°, 10.3°, and 15.2°, and two of the degree 2θ-reflections (±0.2 degrees 2θ) at 14.7°, 17.3°, and 26.2°. In some embodiments, compound of Formula (I) Form II has an XRPD pattern comprising degree 2θ-reflections (±0.2 degrees 2θ) at 5.1°, 10.3°, 14.7°, 15.2°, 17.3°, and 26.2°. In some embodiments, compound of Formula (I) Form II has an XRPD pattern comprising any three degree 2θ-reflections (±0.2 degrees 2θ) selected from the group consisting of 5.1°, 10.3°, 14.7°, 15.2°, 17.3°, and 26.2°.

In some embodiments, compound of Formula (I) Form II has an XRPD pattern comprising degree 2θ-reflections (±0.2 degrees 2θ) at 5.1°, 10.3°, 14.7°, 15.2°, 17.3°, and 26.2°, and one, two, or three of the degree 2θ-reflections (±0.2 degrees 2θ) at 11.4°, 13.8°, and 25.8°. In some embodiments, compound of Formula (I) Form II has an XRPD pattern comprising degree 2θ-reflections (±0.2 degrees 2θ) at 5.1°, 10.3°, 14.7°, 15.2°, 17.3°, and 26.2°, and one or two of the degree 2θ-reflections (±0.2 degrees 2θ) at 11.4°, 13.8°, and 25.8°. In some embodiments, compound of Formula (I) Form II has an XRPD pattern comprising degree 2θ-reflections (±0.2 degrees 2θ) at 5.1°, 10.3°, 14.7°, 15.2°, 17.3°, and 26.2°, and one of the degree 2θ-reflections (±0.2 degrees 2θ) at 11.4°, 13.8°, and 25.8°. In some embodiments, compound of Formula (I) Form II has an XRPD pattern comprising degree 2θ-reflections (±0.2 degrees 2θ) at 5.1°, 10.3°, 14.7°, 15.2°, 17.3°, and 26.2°, and two of the degree 2θ-reflections (±0.2 degrees 2θ) at 11.4°, 13.8°, and 25.8°. In some embodiments, compound of Formula (I) Form II has an XRPD pattern comprising degree 2θ-reflections (±0.2 degrees 2θ) at 5.1°, 10.3°, 11.4°, 13.8°, 14.7°, 15.2°, 17.3°, 25.8°, and 26.2°. In some embodiments, compound of Formula (I) Form II has an XRPD pattern comprising three of the degree 2θ-reflections (±0.2 degrees 2θ) at 5.1°, 10.3°, 11.4°, 13.8°, 14.7°, 15.2°, 17.3°, 25.8°, and 26.2°.

In some embodiments, compound of Formula (I) Form II has a XRPD pattern comprising peaks at:

| Pos. [°2Th.] | Rel. Int. [%] |
|---|---|
| 5.1 | 100 |
| 10.2 | 2 |
| 10.3 | 10 |
| 11.4 | 3 |
| 12.9 | 1 |
| 13.8 | 3 |
| 14.7 | 7 |
| 15.2 | 11 |
| 16.4 | 5 |
| 16.7 | 5 |
| 17.3 | 7 |
| 18.2 | 2 |
| 20.1 | 3 |
| 20.8 | 2 |
| 23.7 | 1 |
| 24.6 | 1 |
| 25.8 | 4 |
| 26.2 | 7 |
| 26.8 | 1 |
| 27.8 | 1 |
| 30.4 | 1 |
| 33.8 | 2 |
| 35.0 | 1 |
| 37.0 | 1 |

In some embodiments, compound of Formula (I) Form II is characterized by a DSC thermogram substantially as shown in FIG. 7.

In some embodiments, compound of Formula (I) Form II is characterized by a DSC thermogram having one or both of (i) a first endothermic transition at about 149° C. followed by an immediate exotherm, indicating a melting/recrystallization transition, at 153° C. and (ii) a second endotherm with an onset at about 161° C.

In some embodiments, compound of Formula (I) Form II is characterized by a TGA curve substantially as shown in FIG. 8. The TGA curve indicates that the compound of Formula (I) Form II is desolvated (i.e. free of solvent).

Preparation of the Solid Forms

In some embodiments, the disclosure provides methods of preparing the solid forms disclosed herein.

In some embodiments, the disclosure provides a method of making a solvate of the compound of Formula (I), wherein the method comprises (i) slurrying the compound of Formula (I) in a solvent and (ii) isolating the solvate or the crystalline form of Formula (I). In some embodiments, isolating the solvate or the crystalline form comprises centrifugation. In some embodiments, about 10-500 mg of the compound of Formula (I) is slurried per mL of solvent. In some embodiments, about 75-350 mg of the compound of Formula (I) is slurried per mL of solvent. In some embodiments, about 100-250 mg of the compound of Formula (I) is slurried per mL of solvent. In some embodiments, the solvent comprises water, methanol, ethanol, isopropanol, 1-butanol, 2-butanol, acetone, acetonitrile, ethyl acetate, isopropyl acetate, butyl acetate, methyl t-butyl ether (MTBE), tetrahydrofuran, toluene, 1-butanone (methyl ethyl ketone), 2-methyl tetrahydrofuran, heptane, cyclohexane, cyclopentyl methyl ether, dichloromethane, N,N-dimethylacetamide, N,N-dimethylformamide, ethyleneglycol, hexane, propylene glycol, methyl butyl ketone, methylcyclohexane, methylisobutylketone, N-methylpyrrolidone, t-butyl alcohol, acetic acid, anisole, dimethyl sulfoxide, isobutyl acetate, methyl acetate, 2-methyl-1-propanol, ethyl ether, ethyl formate, formic acid, pentane, 1-pentanol, propyl acetate, triethylamine, or a mixture thereof. In some embodiments, the solvent comprises water, ethanol, acetonitrile, or a mixture thereof. In some embodiments, the solvent comprises ethanol. In some embodiments, the solvent comprises acetonitrile.

In some embodiments, the method further comprises drying the solvates of the compound of Formula (I) to obtain a crystalline form of the compound of Formula (I), wherein the crystalline form is not a solvate. In some embodiments, the drying is at a temperature of about 20° C. to 100° C. In some embodiments. the drying is at a temperature of about 50° C. In some embodiments, the drying is under vacuum.

In some embodiments, the solvent is acetonitrile and the compound of Formula (I) ethanol solvate Form E1 is isolated. In some embodiments, the compound of Formula (I) ethanol solvate Form E1 is dried to obtain the compound of Formula (I) Form I.

In some embodiments, the solvent is ethanol and the compound of Formula (I) acetonitrile solvate Form ACN1 is isolated. In some embodiments, the compound of Formula (I) acetonitrile solvate Form ACN1 is dried to obtain the compound of Formula (I) Form II.

Pharmaceutical Compositions

The solid forms disclosed herein may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally comprise excipients such as those set forth in the "Handbook of Pharmaceutical Excipients" (1986). Pharmaceutically acceptable excipients include ascorbic acid and other antioxidants, chelating agents such as EDTA, carbohydrates such as dextran, hydroxyalkylcellulose, hydroxyalkylmethylcellulose, stearic acid and the like. In some embodiments, the formulations comprise one or more pharmaceutically acceptable excipients. The pH of the formulations ranges from about 3 to about 11, but is ordinarily about 7 to 10. In some embodiments, the pH of the formulations ranges from about 2 to about 5, but is ordinarily about 3 to 4.

While it is possible for the solid forms of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

In some embodiments, the pharmaceutical formulation is for subcutaneous, intramuscular, intravenous, oral, or inhalation administration.

In some embodiments, the solid forms described herein have optimized/improved pharmacokinetic properties and are amenable to oral administration. For example, the solid forms disclosed herein have improved bioavailability and can therefore be administered by oral administration.

In some embodiments, the formulations of the present invention are suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In some embodiments, the tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a solid form disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some examples, the suspending agent is Sulfobutyl ether beta-cyclodextrin (SEB-beta-CD), for example Captisol®.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 mg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the solid forms disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the solid forms used herein are formulated and dosed as dry powder. In some embodiments, the solid forms used herein are formulated and dosed as a nebulized formulation. In some embodiments, the solid forms used herein are formulated for delivery by a face mask. In some embodiments, the solid forms used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Solid forms of the disclosure may be used to provide controlled release pharmaceutical formulations containing as active ingredient one or more solid forms of the invention ("controlled release formulations") in which the release of the active ingredient are controlled and regulated to allow less frequency dosing or to improve the pharmacokinetic or toxicity profile of a given active ingredient.

Kits

Also provided herein are kits that includes a solid form disclosed herein. In some embodiments the kits described herein may comprise a label and/or instructions for use of the solid form in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the solid form disclosed herein in the treatment of the disease or condition in a subject (e.g., human) in need thereof.

In some embodiments, the kits provided herein comprises individual dose units of a solid form as described herein. Examples of individual dosage units may include pills, tablets, capsules, prefilled syringes or syringe cartridges, IV bags, inhalers, nebulizers etc., each comprising a therapeutically effective amount of the solid form in question. In some embodiments, the kit may contain a single dosage unit and in others, multiple dosage units are present, such as the number of dosage units required for a specified regimen or period.

Also provided are articles of manufacture that include a solid form disclosed herein and a container. In some embodiments, the container of the article of manufacture is a vial, jar, ampoule, preloaded syringe, blister package, tin, can, bottle, box, an intravenous bag, an inhaler, or a nebulizer.

Administration

One or more solid forms of the disclosure are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, solid form disclosed herein are administered by inhalation or intravenously. In some embodiments, the solid form disclosed herein are administered orally. It will be appreciated that the preferred route may vary with for example the condition of the recipient.

In the methods of the present invention for the treatment of a viral infection, the solid form disclosed herein can be administered at any time to a human who may come into contact with the virus or is already suffering from the viral infection. In some embodiments, the solid form disclosed herein can be administered prophylactically to humans coming into contact with humans suffering from the viral infection or at risk of coming into contact with humans suffering from the viral infection, e.g., healthcare providers. In some embodiments, administration of the solid form disclosed herein can be to humans testing positive for the viral infection but not yet showing symptoms of the viral infection. In some embodiments, administration of the solid form disclosed herein can be to humans upon commencement of symptoms of the viral infection.

In some embodiments, the methods disclosed herein comprise event driven administration of the solid form disclosed herein to the subject.

As used herein, the terms "event driven" or "event driven administration" refer to administration of the solid form described herein, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, a solid form disclosed herein is administered before exposure of the subject to the virus.

In some embodiments, a solid form disclosed herein is administered before and after exposure of the subject to the virus.

In some embodiments, a solid form disclosed herein is administered after exposure of the subject to the virus.

An example of event driven dosing regimen includes administration a solid form disclosed herein within 24 to 2 hours prior to the virus, followed by administration of a solid form disclosed herein every 24 hours during the period of exposure, followed by a further administration of a solid form disclosed herein after the last exposure, and one last administration of a solid form disclosed herein 24 hours later.

A further example of an event driven dosing regimen includes administration of a solid form disclosed herein within 24 hours before the viral exposure, then daily administration during the period of exposure, followed by a last administration approximately 24 hours later after the last exposure (which may be an increased dose, such as a double dose).

The specific dose level of a solid form disclosed herein for any particular subject will depend upon a variety of factors including the activity of the specific solid form employed, the age, body weight, general health, sex, diet, time of administration, route of administration, and rate of excretion, drug combination and the severity of the particular disease in the subject undergoing therapy. For example, a dosage may be expressed as number of milligrams of a solid form disclosed herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a solid form disclosed herein administered per dose or per day. Daily dosage of a solid form disclosed herein may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a solid form disclosed herein may be adjusted over the course of the treatment, based on the judgment of the administering physician.

The solid forms disclosed herein may be administered to an individual (e.g., a human) in a therapeutically effective amount. In some embodiments, the solid forms are administered once daily.

The solid forms disclosed herein can be administered by any useful route and means, such as by oral or parenteral (e.g., intravenous) administration. Therapeutically effective amounts of the solid forms may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the solid forms provided herein include from about 0.3 mg to about 30 mg per day, or from about 30 mg to about 300 mg per day, or from about 0.3 mg to about 30 mg per day, or from about 30 mg to about 300 mg per day.

A solid form of the present disclosure may be combined with one or more additional therapeutic agents in any dosage amount of the solid form of the present disclosure (e.g., from 1 mg to 1000 mg of solid form). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the solid forms are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the solid forms of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a solid form provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1-4,000 mg/day, between about 1-3,000 mg/day, between 1-2,000 mg/day, about 1-1,000 mg/day, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day. In some embodiments, the total daily dosage for a human subject may be about 100-200, 100-300, 100-400, 100-500, 100-600, 100-700, 100-800, 100-900, 100-1000, 500-1100, 500-1200, 500-1300, 500-1400, 500-1500, 500-1600, 500-1700, 500-1800, 500-1900, 500-2000, 1500-2100, 1500-2200, 1500-2300, 1500-2400, 1500-2500, 2000-2600, 2000-2700, 2000-2800, 2000-2900, 2000-3000, 2500-3100, 2500-3200, 2500-3300, 2500-3400, 2500-3500, 3000-3600, 3000-3700, 3000-3800, 3000-3900, or 3000-4000 mg/day. In some embodiments, the total daily dosage for a human subject is about 500-1000 mg/day administered once or twice daily.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose. In some embodiments, the total daily dosage for a human subject may be about 1500 mg/day administered in a single dose. In some embodiments, the total daily dosage for a human subject may be about 2000 mg/day administered in a single dose. In some embodiments, the total daily dosage for a human subject may be about 2500 mg/day administered in a single dose. In some embodiments, the total daily dosage for a human subject may be about 3000 mg/day administered in a single dose. In some embodiments, the total daily dosage for a human subject may be about 4000 mg/day administered in a single dose.

In some embodiments, the total daily dosage for a human subject may be about 100 mg/day administered in two doses daily. In some embodiments, the total daily dosage for a human subject may be about 150 mg/day administered in two doses daily. In some embodiments, the total daily dosage for a human subject may be about 200 mg/day administered in two doses daily. In some embodiments, the total daily dosage for a human subject may be about 250 mg/day administered in two doses daily. In some embodiments, the total daily dosage for a human subject may be about 300 mg/day administered in two doses daily. In some embodiments, the total daily dosage for a human subject may be about 350 mg/day administered in two doses daily. In some embodiments, the total daily dosage for a human subject may be about 400 mg/day administered in two doses daily. In some embodiments, the total daily dosage for a human subject may be about 450 mg/day administered in two doses daily. In some embodiments, the total daily dosage for a human subject may be about 500 mg/day administered in two doses daily. In some embodiments, the total daily dosage for a human subject may be about 550 mg/day administered in two doses daily. In some embodiments, the total daily dosage for a human subject may be about 600 mg/day administered in two doses daily. In some embodiments, the total daily dosage for a human subject may be about 650 mg/day administered in two doses daily. In some embodiments, the total daily dosage for a human subject may be about 700 mg/day administered in two doses daily. In some embodiments, the total daily dosage for a human subject may be about 750 mg/day administered in two doses daily. In some embodiments, the total daily dosage for a human subject may be about 800 mg/day administered in two doses daily. In some embodiments, the total daily dosage for a human subject may be about 850 mg/day administered in two doses daily. In some embodiments, the total daily dosage for a human subject may be about 900 mg/day administered in two doses daily. In some embodiments, the total daily dosage for a human subject may be about 950 mg/day administered in two doses daily. In some embodiments, the total daily dosage for a human subject may be about 1000 mg/day administered two doses daily. In some embodiments, the total daily dosage for a human subject may be about 1500 mg/day administered two doses daily. In some embodiments, the total daily dosage for a human subject may be about 2000 mg/day administered two doses daily. In some embodiments, the total daily dosage for a human subject may be about 2500 mg/day administered two doses daily. In some embodiments, the total daily dosage for a human subject may be about 3000 mg/day administered two doses daily. In some embodiments, the total daily dosage for a human subject may be about 4000 mg/day administered two doses daily.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a solid form disclosed herein is administered once daily in a method disclosed herein. In some embodiments, a solid form disclosed herein is administered twice daily in a method disclosed herein. In some embodiments, a solid form disclosed herein is administered three times daily in a method disclosed herein.

In some embodiments, a solid form disclosed herein is administered once daily in the total daily dose of 100-4000 mg/day. In some embodiments, a solid form disclosed herein is administered twice daily in the total daily dose of 100-4000 mg/day. In some embodiments, a solid form disclosed herein is administered three times daily in the total daily dose of 100-4000 mg/day. In some embodiments, a solid form disclosed herein is administered once daily in the total daily dose of 300-900 mg/day.

The frequency of dosage of the solid form of the present disclosure will be determined by the needs of the individual patient and can be, for example, once per day or twice, or more times, per day. Administration of the solid form continues for as long as necessary to treat the viral infection. For example, a solid form can be administered to a human being infected with the virus for a period of from 20 days to 180 days or, for example, for a period of from 20 days to 90 days or, for example, for a period of from 30 days to 60 days.

Administration can be intermittent, with a period of several or more days during which a patient receives a daily dose of a solid form of the present disclosure followed by a period of several or more days during which a patient does not receive a daily dose of the solid form. For example, a patient can receive a dose of the solid form every other day, or three times per week. Again by way of example, a patient can receive a dose of the solid form each day for a period of from 1 to 14 days, followed by a period of 7 to 21 days during which the patient does not receive a dose of the solid form, followed by a subsequent period (e.g., from 1 to 14 days) during which the patient again receives a daily dose of the solid form. Alternating periods of administration of the solid form, followed by non-administration of the solid form, can be repeated as clinically required to treat the patient.

The solid forms of the present disclosure or the pharmaceutical compositions thereof may be administered once, twice, three, or four times daily, using any suitable mode described above. Also, administration or treatment with the solid forms may be continued for a number of days; for example, commonly treatment would continue for at least 3 days, at least 5 days, at least 7 days, 14 days, or 28 days, for one cycle of treatment.

Methods of Use

The present disclosure also provides a method of treating or preventing a viral infection in a subject (e.g., human) in need thereof, the method comprising administering to the subject a solid form described herein.

In some embodiments, the present disclosure provides a method of treating a viral infection in a subject (e.g., human) in need thereof, the method comprising administering to a subject in need thereof a solid form described herein.

In some embodiments, the solid form described herein is administered to the human via oral, intramuscular, intravenous, subcutaneous, or inhalation administration.

In some embodiments, the present disclosure provides for methods of treating or preventing a viral infection in a subject (e.g., human) in need thereof, the method comprising administering to the subject a solid form disclosed herein and at least one additional active therapeutic or prophylactic agent.

In some embodiments, the present disclosure provides for methods of treating a viral infection in a subject (e.g., human) in need thereof, the method comprising administering to the subject a solid form disclosed herein, and at least one additional active therapeutic or prophylactic agent.

In one embodiment, the present disclosure provides for methods of inhibiting a viral polymerase in a cell, the methods comprising contacting the cell infected by a virus with a solid form disclosed herein, whereby the viral polymerase is inhibited.

In one embodiment, the present disclosure provides for methods of inhibiting a viral polymerase in a cell, the methods comprising contacting the cell infected by a virus with a solid form disclosed herein, and at least one additional active therapeutic agent, whereby the viral polymerase is inhibited.

Also provided here are the uses of the solid forms disclosed herein for use in treating or preventing a viral infection in a subject in need thereof. For example, provided herein are uses of the solid forms disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g., a human) in need thereof, the method comprising administering to the subject a solid form disclosed herein. Paramyxoviridae viruses include, but are not limited to Nipah virus, Hendra virus, measles, mumps, and parainfluenze virus.

In some embodiments, the viral infection is a human parainfluenza virus, Nipah virus, Hendra virus, measles, or mumps infection.

In some embodiments, the viral infection is a pneumoviridae virus infection. As such, in some embodiments, the present disclosure provides a method of treating a pneumoviridae virus infection in a human in need thereof, the method comprising administering to the human a solid form provided herein. Pneumoviridae viruses include, but are not limited to, respiratory syncytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a solid form disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a solid form provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a solid form disclosed herein, wherein the administration is by inhalation.

In some embodiments, the present disclosure provides a method for reducing the viral load associated with RSV infection, wherein the method comprises administering to a human infected with RSV a solid form disclosed herein.

In some embodiments, the viral infection is a picornaviridae virus infection. As such, in some embodiments, the present disclosure provides a method of treating a picornaviridae virus infection in a human in need thereof, the method comprising administering to the human a solid form of the present disclosure. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection (HRV). In some embodiments, the Picornaviridae virus infection is HRV-A, HRV-B, or HRV-C infection.

In some embodiments, the viral infection is selected from the group consisting of Coxsackie A virus infection, Coxsackie A virus infection, enterovirus D68 infection, enterovirus B69 infection, enterovirus D70 infection, enterovirus A71 infection, and poliovirus infection.

In some embodiments, the present disclosure provides a solid form, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a solid form described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese encephalitis virus infection. In some embodiments, the flaviviridae virus infection is a hepatitis C virus infection.

In some embodiments, the flaviviridae virus infection is a dengue virus infection, yellow fever virus infection, West Nile virus infection, tick borne encephalitis, Kunjin Japanese encephalitis, St. Louis encephalitis, Murray valley encephalitis, Omsk hemorrhagic fever, bovine viral diarrhea, zika virus infection, or a HCV infection.

In some embodiments, the present disclosure provides use of a solid form disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a solid form disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a solid form for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a solid form provided herein. In some embodiments, the coronavirus infection is a Severe Acute Respiratory Syndrome (SARS-CoV) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant), P.1 variant (the Brazil variant), B.1.1.7 with E484K variant, B.1.1.207 variant, B.1.1.317 variant, B.1.1.318 variant, B.1.429 variant, B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a solid form for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, and zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a solid form disclosed herein. In some embodiments, the arenaviridae virus infection is a Lassa infection or a Junin infection.

In some embodiments, the present disclosure provides a solid form for use in the treatment of an arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

As described more fully herein, the solid forms described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

Combination Therapy

The solid forms described herein can also be used in combination with one or more additional therapeutic agents. As such, also provided herein are methods of treatment of the a viral infection in a subject in need thereof, wherein the methods comprise administering to a subject in need thereof a solid form of the disclosure and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, Cytochrome P450 3A4 inhibitors, Peptidyl-prolyl cis-trans isomerase A inhibitors, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, or a combination thereof. In some embodiments, the additional therapeutic agent is β-D-N4-hydroxycytidine.

In some embodiments, the additional therapeutic agent is a pyrophosphate analogue. For example, in some embodiments, the additional therapeutic agent is foscarnet or phosphonoacetic acid.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof. In some embodiments, the additional therapeutic agent is sangivamycin, 0-d-N4-Hydroxycytidine (NHC), MK-4482 (EIDD-2801), EIDD-1931, or a combination thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof. In some embodiments, the antiviral agent is S-217622.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of AT-527, daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, DAS-181, XC-221 and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, interferon alfa 2 ligand, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof. In some examples, the additional therapeutic agent is interferon-beta. For example, the additional therapeutic agent is interferon-beta-1a, such as SNG-001. In some embodiments, the additional therapeutic agent is an interferon-inducing agent, such as tilorone hydrochloride. In some embodiments, the additional therapeutic agent is IL-17 antagonist such as ixekizumab, secukinumab, IMU-838, and vidofludimus.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, azoximer bromide, IMM-101 and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the antiviral agent is DFV890. In some embodiments, the antiviral agent is MAS825. In some embodiments, the antiviral agent is emetine. In some embodiments, the antiviral agent is virafin. In some embodiments, the antiviral agent is berdazimer sodium. In some embodiments, the antiviral agent is KT-07. In some embodiments, the antiviral agent is iorta-carrageenan. In some embodiments, the antiviral agent is polyoxidonium. In some embodiments, the antiviral agent is bitespiramycin. In some embodiments, the antiviral agent is an anti-Adrenomedullin antibody, such as enibarcimab. In some embodiments, the antiviral agent is an annexin A5 stimulator, such as SY-005.spyke. In some embodiments, the antiviral agent is a COVID19 replicase polyprotein lab inhibitor, such as DC-402234. In some embodiments, the antiviral agent is a host cell factor modulator, such as GBV-006.

In some embodiments, the antiviral agent is protoporphyrin IX, stannous, SnPP protoporphyrin and verteporfin. In some embodiments, the antiviral agent is RBT-9. In some embodiments, the antiviral agent is thymosin.

In some embodiments, the additional therapeutic agent is ivermectin.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. For example, the additional therapeutic agent is dihydroartemisinin piperaquine, Pyramax.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, AT-527, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to AIC-649, alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, CRV-431, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, thymalfasin, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies, autologous stem cell therapies). In some embodiments, the additional therapeutic agent is an immunotherapeutic peptides such as tertomotide. In some embodiments, the additional therapeutic agent is a CCL26 gene inhibitor, such as mosedipimod. In some embodiments, the additional therapeutic agent is FT-516.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors (i.e. idelalisib, duvelisib), HIV antibodies, and bispecific antibodies, and "antibody-like" therapeutic proteins, and combinations thereof.

In some examples, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine-; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some examples, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, GC-376, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some examples, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, isoquercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional-therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), EOM-613 anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, balixafortide, motixafortide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some examples, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof. In some examples, the additional therapeutic agent is a HIV vaccine, such as DermaVir.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is a COVID19 Spike glycoprotein inhibitor, such as tafoxiparin.

In some embodiments, the additional therapeutic agent is a Furin inhibitor, such as BOS-857, BOS-981, alpha defensins.

In some embodiments, the additional therapeutic agent is a CD73 agonist, such as FP-1201.

In some embodiments, the additional therapeutic agent is a CGRP receptor antagonist, such as BHV-3500.

In some embodiments, the additional therapeutic agent is a Cytochrome P450 3A4 inhibitor/Peptidyl-prolyl cis-trans isomerase A inhibitor, such as alisporivir.

In some embodiments, the additional therapeutic agent is a progesterone receptor agonist, such as Progesterone-IBSA.

In some embodiments, the additional therapeutic agent is a GABA A receptor modulator, such as brexanolone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), abivertinib maleate (STI-5656), zanubrutinib (BGB-3111), CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, TL-895, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is a receptor tyrosine kinase inhibitor (RTKI). In some embodiments, the additional therapeutic agent is tyrphostin A9 (A9). In some embodiments, the additional therapeutic agent is a TEK receptor tyrosine kinase inhibitor.

In some embodiments, the additional therapeutic agent is a tyrosine kinase inhibitor, such as masitinib.

In some embodiments, the additional therapeutic agent is a sphingosine kinase-2 (sk2) inhibitor, such as opaganib.

In some embodiments, the additional therapeutic agent is a Syk tyrosine kinase inhibitor, such as fostamatinib disodium.

In some embodiments, the additional therapeutic agent is a cholesterol ester transfer protein inhibitor, such as dalcetrapib.

In some embodiments, the additional therapeutic agent is a kinase inhibitor such as pacritinib.

In some embodiments, the additional therapeutic agent is an Axl tyrosine kinase receptor inhibitor, such as bemcentinib.

In some embodiments, the additional therapeutic agent is a FYVE finger phosphoinositide kinase inhibitor.

In some embodiments, the additional therapeutic agent is a checkpoint kinase inhibitor, such as prexasertib;

In some embodiments, the additional therapeutic agent is a MAP kinase inhibitor, such as KTH-222, ATI-450.

In some embodiments, the additional therapeutic agent is a casein kinase II inhibitor, such as silmitasertib.

In some embodiments, the additional therapeutic agent is a Bcr-Abl tyrosine kinase inhibitor, such as radotinib.

In some embodiments, the additional therapeutic agent is a phospholipase A2 inhibitor, such as icosapent ethyl.

In some embodiments, the additional therapeutic agent is a mTOR inhibitor, such as sirolimus.

In some embodiments, the additional therapeutic agent is a pi3k/mTOR inhibitor such as dactolisib.

In some embodiments, the additional therapeutic agent is a Hsp90 inhibitor, such as ganetespib, ADX-1612.

In some embodiments, the additional therapeutic agent is a MEK inhibitor such as ATR-002.

In some embodiments, the additional therapeutic agent is a topoisomerase II inhibitor, such as etoposide.

In some embodiments, the additional therapeutic agent is an exportin 1 inhibitor, such as selinexor, verdinexor.

In some embodiments, the additional therapeutic agent is a dual inhibitor of PARP1/2 and Tankyrase 1/2, such as stenoparib (2X-121).

In some embodiments, the additional therapeutic agent is a cyclin dependent kinase inhibitor, such as CYC-065, CYC-202, fadraciclib, seliciclib.

In some embodiments, the additional therapeutic agent is a cytosine DNA methyltransferase inhibitor, such as decitabine, azacytidine, DUR-928.

In some embodiments, the additional therapeutic agent is a DHFR inhibitor, such as methotrexate.

In some embodiments, the additional therapeutic agent is a Deoxyribonuclease stimulator, such as Descartes-30.

In some embodiments, the additional therapeutic agent is a Ribonuclease stimulator, such as ranpirnase.

In some embodiments, the additional therapeutic agent is an eukaryotic initiation factor 4A1 (eIF4A1) inhibitor, such as zotatifin.

In some embodiments, the additional therapeutic agent is a small ubiquitin related modifier inhibitor, such as TAK-981.

In some embodiments, the additional therapeutic agent is a Ubiquitin ligase modulator, such as KPG-818.

In some embodiments, the additional therapeutic agent is an integrin agonist such as 7HP-349.

In some embodiments, the additional therapeutic agent is a BET inhibitor, such as apabetalone.

In some embodiments, the additional therapeutic agent is a BRD4 inhibitor, such as CPI-0610, ABBV-744.

In some embodiments, the additional therapeutic agent is an ER1 inhibitor, such as toremifene.

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, disulfiram+copper gluconate, and combinations thereof. in some embodiments, the additional therapeutic agent is carfilzomib. In some embodiments, the additional therapeutic agent is an alkylating agent, such as melphalan.

In some embodiments, the additional therapeutic agent is a vaccine. For example, in some embodiments, the additional therapeutic agent is a DNA vaccine, RNA vaccine, live-attenuated vaccine, inactivated vaccine (i.e. inactivated SARS-CoV-2 vaccine), therapeutic vaccine, prophylactic vaccine, protein based vaccine, viral vector vaccine, cellular vaccine, dendritic cell vaccine (i.e. LV-SMENP-DC, LV-SMENP-DC, or AV-COVID-19) or a combination thereof. In some embodiments, the additional therapeutic agent is mRNA-1273, mRNA-1273.211, mRNA-1273.351, mRNA-1283, CVnCoV, DS-5670-, SP-0254, ARCoV, Nanocovax-. In some embodiments, the additional therapeutic agent is INO-4800 or INO-4700. In some embodiments, the therapeutic agent is a DNA vaccine, such as AG301-COVID19, bacTRL-Spike, GX-19, AG-0301-COVID19, ZyCoC-D, GLS-5310, CORVax. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is an HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g. influenza A [H5N1] virus monovalent vaccine and influenza A [H1N1] 2009 virus monovalent vaccines), (ii) trivalent vaccine for influenza A and B viruses (e.g. Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g. Adenovirus Type 4 and Type 7 Vaccine, Live, Oral). In some embodiments, the additional therapeutic agent is a rotavirus vaccine (e.g. Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g. Havrix and Vagta). In some embodiments, the additional therapeutic agent is poliovirus vaccines (e.g. Kinrix, Quadracel, OPV, and Ipol). In some embodiments, the additional therapeutic agent is a yellow fever virus vaccine (e.g. YF-Vax). In some embodiments, the additional therapeutic agent is a Japanese encephalitis virus vaccines (e.g. Ixiaro and JE-Vax). In some embodiments, the additional therapeutic agent is a measles vaccine (e.g. M-M-R II and ProQuad). In some embodiments, the additional therapeutic agent is a mumps vaccine (e.g. M-M-R II and ProQuad). In some embodiments, the additional therapeutic agent is a rubella vaccine (e.g. M-M-R II and ProQuad). In some embodiments, the additional therapeutic agent is a varicella vaccine (e.g. ProQuad). In some embodiments, the additional therapeutic agent is a rabies vaccine (e.g. Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g. HEV239). In some embodiments, the additional therapeutic agent is a MERS vaccine (e.g. MVA-MERS-S, VTP-500). In some embodiments, the additional therapeutic agent is a BCG vaccine. In some embodiments, the additional therapeutic agent is a recombinant protein subunit vaccine (e.g. ZF-2001), EuCorVAc-19, GBP-510, Sinopharma vaccine, SpyCatcher vaccine, SP-0253, VBI-2902, UB-612, MVC-COV1901. In some embodiments, the additional therapeutic agent is a live attenuated bacterial vaccine (e.g. MV-130). In some embodiments, the additional therapeutic agent is a recombinant non-replicating vaccine (e.g. JNJ78436735 (Ad26 SARS-CoV-2)). In some embodiments, the additional therapeutic agent is poly-TLR agonist polyantigenic vaccine (e.g. *Mycobacterium* w).

In some embodiments, the additional therapeutic agent is a QAZCOVID-IN vaccine. In some embodiments, the additional therapeutic agent is a GRAd-COV2 vaccine. In some embodiments, the additional therapeutic agent is an EpiVacCorona vaccine. In some embodiments, the additional therapeutic agent is a 2019-nCov vaccine. In some embodiments, the additional therapeutic agent is Ad5-nCoV. In some embodiments, the additional therapeutic agents is the mRNA vaccine CV-07050101, BNT-162, BNT162a1, BNT162b1, BNT162b2, BNT-162b3, BNT-162b1, BNT162c2 (prime/boost, single or multiple doses), SW-0123, CoV-2 SAM (LNP) vaccine, PTX-COVID19-B. In some embodiments, the additional agent is a self-replicating RNA vaccine, such as EXG-5003. In some embodiment, the additional agent is AZD1222 (ChAdOx1 nCov-19) vaccine. In some embodiments, the additional agent is Gam-COVID-Vac (Ad26), Gam-COVID-Vac (Ad5), Gam-COVID-Vac (Ad26 Prime-boost), Sputnik-Light vector vaccine (rAd26), Covax-19, NasoVAX, NDV-HXP-S vaccine, AdCOVID, VSV-vector based vaccine-. In some embodiments, the additional therapeutic agents is TiterQuil-1055 adjuvanted vaccine. In some embodiments, the additional therapeutic agents is LUNAR-COV19 (ARCT-021), Terra-CoV2. In some embodiments, the additional agent is COVID-19 S-Trimer. In some embodiments, the additional agent is TNX-1810, and/or TNX-1820, and/or TNX-1830. In some embodiments, the additional agent is VaxiPatch COVID-19 vaccine. In some embodiments, the additional agent is VBI-2901. In some embodiments, the additional agent is VLA-2001. In some embodiments, the additional agent is exoVACC-SARS-CoV2. In some embodiments, the additional agent is SCB-2019. In some embodiments, the additional agent is MV-SARS-CoV-2. In some embodiments, the additional agent is NVX-CoV2373, Matrix-M and NVX-CoV2373. In some embodiments, the additional agent is BBV152A, B, C, PicoVacc, KBP-COVID-19, MF59 adjuvanted SARS-CoV-2 Sclamp, MVC-COV1901, SCB-2019 (COVID-19 S-Trimer+CpG1018+AS03), TMV-083, V-591, VPM1002, V-SARS-, AdCLD-Cov19, AKS-452, BVRS-GamVac, BVRS-GamVac-Combi, CIGB-2020, COVAC-2, FINLAY-FR-1, KD-414, S-268019, T-COVID, CDX-005, COH-04S1, ABNCoV2, ERUCOV-VAC, fakhravac, Kocak-19 inaktif adjuvanh COVID-19 vaccine, NBP-2001, CoVepiT, VXA-CoV2-1, CoVac-1, AT-301, LNP-nCoVsaRNA, AdimrSC-2f, BBV-154, COVID-19 XWG-03, FINLAY-FR-2, MV-014-212, MVA-SARS-2-S, RAZI Cov Pars, SPFN_1B-06-PL, V-590, Ad5-Covid-S/N, CORAL.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS- CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody. In some embodiments, the additional therapeutic agent is anti-IL-6R mAb. For example, the additional therapeutic agent is TZLS-501 or siltuximab. In some embodiments, the additional therapeutic agent is an antibody that targets specific sites on ACE2. In some embodiments, the additional therapeutic agent is a polypeptide targeting SARS-CoV-2 spike protein (S-protein). In some embodiments, the additional therapeutic agent is a virus suppressing factor (VSF, HzVSFv13).

In some embodiments, the additional therapeutic agent is an anti-CD147 antibody. For example, the additional therapeutic agent is meplazumab.

In some embodiments, the additional therapeutic agent is a phosphodiesterase type 4 (PDE4) or phosphodiesterase type 5 (PDE5) inhibitor. In some embodiments, the additional therapeutic agent is a PDE5 inhibitor, for example, the additional therapeutic agent is sildenafil. In some embodiments, the additional therapeutic agent is a PDE3/PDE4 inhibitor, for example, the additional therapeutic agent is brilacidin, ensifentrine.

In some embodiments, the additional therapeutic agent is an agent targeting NKGA2. In some embodiments, the additional therapeutic agent is a checkpoint inhibitor. In some embodiments, the additional therapeutic agent is NKG2 A B activating NK receptor antagonist, such as monalizumab. In some examples, the additional therapeutic agent is a CTLA-4 checkpoint inhibitor, such as BPI-002.

In some embodiments, the additional therapeutic agent is a CD73 antagonist, such as CPI-006, AK-119.

In some embodiments, the additional therapeutic agent is recombinant cytokine gene-derived protein injection. In some embodiments, the additional therapeutic agent is amnion-derived cellular cytokine solution, such as ST-266.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of AT-527, ribavirin, favipiravir, lamivudine, galidesivir, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is a beta-catenin inhibitor. For example, the additional therapeutic agent is tetrandrine.

In some embodiments, the additional therapeutic agent is a trypsin inhibitor, for example the additional therapeutic agent is ulinastatin, TAK-671.

In some embodiments, the additional therapeutic agent is selected from the group consisting of ABBV-744, dBET6, MZ1, CPI-0610, Sapanisertib, Rapamycin, Zotatifin, Verdinexor, Chloroquine, Dabrafenib, WDB002, Sanglifehrin A, FK-506, Pevonedistat, Ternatin 4, 4E2RCat, Tomivosertib, PS3061, IHVR-19029, Captopril, Lisinopril, Camostat, Nafamostat, Chloramphenicol, Tigecycline, Linezolid, and combinations thereof.

In some embodiments, the additional therapeutic agent is selected form the group consisting of JQ-1, RVX-208, silmitasertib, TMCB, apicidin, valproic acid, Bafilomycin A1, E-52862, PD-144418, RS-PPCC, PD28, haloperidol, entacapone, indomethacin, LTX-109, MAS-825, Metformin, Metformin glycinate, MRG-001, Medregen, MRx-0004, thimerosal, Ponatinib, H-89, Merimepodib, Migalastat, Mycophenolic acid, Ribavirin, XL413, CCT 365623, Midostaurin, Ruxolitinib, ZINC1775962367, ZINC4326719, ZINC4511851, ZINC95559591, AC-55541, AZ8838, Daunorubicin, GB110, S-verapamil, AZ3451, and combinations thereof.

In some embodiments, the additional therapeutic agent is a drug targeting the coronavirus main protease 3CLpro (e.g. lopinavir). In some embodiments the additional therapeutic agent is a drug targeting the papain-like protease PLpro (e.g. lopinavir). In some examples, the additional therapeutic agent is a drug that functions as a virus-host cell fusion inhibitor to prevent viral entry into host cells (e.g. arbidol). In some embodiments, the additional therapeutic agent is a TMPRSS2 inhibitor (e.g. camostat mesylate).

In some embodiments, the additional therapeutic agent is a serine protease inhibitor, such as LB1148, upamostat, RHB-107, alpha-1 antitrypsin, tranexamic acid.

In some embodiments, the additional therapeutic agent is a replicase polyprotein 1a inhibitor/replicase polyprotein lab inhibitor/protease inhibitor/coronavirus 3C protease like inhibitor, such as PF-07304814.

In some embodiments, the additional therapeutic agent is a SARS coronavirus 3C protease like inhibitor, such as PF-07321332.

In some embodiments, the additional therapeutic agent is a serine protease inhibitor, such as DS-2319, repurposed nafamostat mesylate.

In some embodiments, the additional therapeutic agent is a serine protease inhibitor/Transmembrane serine protease 2 inhibitor, such as nafamostat.

In some embodiments, the additional therapeutic agent is a cysteine protease inhibitor, such as SLV-213

In some embodiments, the additional therapeutic agent is a serine threonine protein kinase ATR inhibitor, such as berzosertib.

In some embodiments, the additional therapeutic agent is an inhibitor of neutrophil elastase, such as lonodelestat.

In some embodiments, the additional therapeutic agent is an α-ketoamide.

In some examples, the additional therapeutic agent is a poly-ADP-ribose polymerase 1 (PARP1) inhibitor, for example, the additional therapeutic agent is CVL218.

In some embodiments, the additional therapeutic agent is selected from the group consisting of 6'-fluorinated aristeromycin analogues, acyclovir fleximer analogues, disulfiram, thiopurine analogues, ASC09F, CNM-AgZn-17, genistein, JAN-101, nitric oxide (inhalant), nitric oxide based antiviral formulation (oral), RTD-1, PrEP-001, QBKPN, RUTI, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5] decan-3-one derivatives, 5-1226, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an anti-CD147 antibody. For example, the additional therapeutic agent is meplazumab.

In some embodiments, the additional therapeutic agent is an antibody that binds to a coronavirus, for example an antibody that binds to SARS or MERS. In some embodiments, the additional therapeutic agent is a 2019-nCoV virus antibody. In some embodiments, the antibody is ABBV-47D11. In some embodiments, the antibody is COVID-GUARD. In some embodiments, the antibody is C144-LS+C135-LS. In some embodiments, the antibody is DXP-604. In some embodiments, the antibody is JMB-2002. In some embodiments, the antibody is LY-CovMab. In some embodiments, the antibody is LY-CoV555. In some embodiments, the antibody is S309. In some embodiments, the antibody is SAB-185. In some embodiments, the antibody is SI-F019. In some embodiments, the antibody is CB6. In some embodiments, the antibody is COR-101. In some embodiments, the antibody is STI-1499. In some embodiments, the antibody is JS016. In some embodiments, the antibody is VNAR. In some embodiments, the antibody is VIR-7832 and/or VIR-7831. In some embodiments, the antibody is REGN-COV2 (casirivimab+imdevimab or REGN10933+RGN10987). In some embodiments, the antibody is BAT2020, BAT2019. In some embodiments, the antibody is 47D11. In some embodiments, the antibody cocktail is COVID-SHIELD. In some embodiments, the antibody is BRII-196, BRII-198. In some embodiments, the antibody is ADG-20. In some embodiments, the antibody is ABP-300. In some embodiments, the antibody is BI-767551. In some embodiments, the antibody is GSK-4182136. In some embodiments, the antibody is AZD-7442. In some embodiments, the antibody is regdanvimab. In some embodiments, the antibody is etesevimab. In some embodiments, the antibody is SAB-301. In some embodiments, the antibody is AOD-01. In some embodiments, the antibody is COVID-AMG. In some embodiments, the antibody is MW-33. In some embodiments, the antibody is DXP-593. In some embodiments, the antibody is BSVEQAb. In some embodiments, the antibody is anti-SARS-CoV-2 IgY. In some embodiments, the antibody is COVID-EIG. In some embodiments, the antibody is CSL-760. In some embodiments, the antibody is REGN-3048-3051. In some embodiments, the antibody is ADM-03820. In some embodiments, the antibody is HFB-30132A. In some embodiments, the additional therapeutic agent is an anti-Hemolysin alpha antibody, such as tosatoxumab. In some embodiments, the additional therapeutic agent is an anti-LPS antibody IMM-124-E. In some embodiments, the antibody is INM-005, SCTA01, TY-027, XAV-19.

Compositions of the invention are also used in combination with other active ingredients. For the treatment of 2019-nCoV virus infections, preferably, the other active therapeutic agent is active against coronavirus infections, for example 2019-nCoV virus infections. The solid forms and compositions of the present invention are also intended for use with general care provided patients with 2019-nCoV viral infections, including parenteral fluids (including dextrose saline and Ringer's lactate) and nutrition, antibiotic (including metronidazole, amphotericin B, amoxicillin/clavulanate, trimethoprim/sulfamethoxazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K, vitamin D, cholecalciferol, vitamin C and zinc sulfate), anti-inflammatory agents (such as ibuprofen or steroids), corticosteroids such as methylprednisolone, prednisone, mometasone, immunomodulatory medications (e.g. interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine. In some examples, the additional therapeutic agent is a corticosteroid, for example the additional therapeutic agent is ciclesonide, budesonide. In some embodiments, the additional therapeutic agent is EIDD-2801 (MH-4482, Molnupiravir).

In some embodiments, the solid forms disclosed herein are used in combination with inhibitors such as Panaphix (PAX-1), which inhibit production of pro-inflammatory cytokines. In some embodiments, the solid forms disclosed herein are used in combination with inhibitors such as NCP-112 which inhibit excessive immune response such as cytokine storm.

In some embodiments, the additional therapeutic agent is an antifungal agent, for example itraconazole or 17-OH-itraconazole.

In some examples, the additional therapeutic agent is an immunomodulator.

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators (i.e nivolumab); programmed death-ligand 1 (Pd-L1) modulators (i.e. camrelizumab, pembrolizumab); IL-15 modulators; interleukin-7 modulators (i.e. efineptakin alfa, plaquenil (hydroxychloroquine), CYT-107); proleukin (aldesleukin, IL-2); interferon alfa; interferon alfa-2b; interferon alfa-n3; lactoferrin, ozanimod, pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; interleukin-15/Fc fusion protein, AM-0015, ALT-803, NIZ-985, NKTR-255, NKTR-262, NKTR-214, normferon, peginterferon alfa-2a, peginterferon alfa-2b, peginterferon lambda-1a, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide. In some embodiments, the additional therapeutic agent is CD24Fc. In some embodiments, the additional therapeutic agent is a type I IL-1 receptor antagonists, such as anakinra, astegolimab (MSTT1041A, RG-6149), UTTR1147A In some embodiments, the additional therapeutic agent is Ampligen.

In some embodiments, the additional therapeutic agent is lefitolimod.

In some embodiments, the additional therapeutic agent is gamunex.

In some embodiments, the additional therapeutic agent is a CD3 antagonist, such as foralumab.

In some embodiments, the additional therapeutic agent is a KEAP1 modulator, such as SFX-01.

In some embodiments, the additional therapeutic agent is a PARP inhibitor, such as BGP-15.

In some embodiments, the additional therapeutic agent is octagam.

In some embodiments, the additional therapeutic agent is RPH-104. In some embodiments, the additional therapeutic agent is canakinumab.

In some embodiments, the additional therapeutic agent is a leukocyte Ig like receptor A4 modulator, such as daxdilimab.

In some embodiments, the additional therapeutic agent is a Melanocortin MC1 receptor agonist, such as PL-8177.

In some embodiments, the additional therapeutic agent is an IL-33 ligand inhibitor such as MEDI3506.

In some embodiments, the additional therapeutic agent is an IL-5 receptor antagonist, such as mepolizumab.

In some embodiments, the additional therapeutic agent is an IL-12/IL23 inhibitor, such as apilimod, apilimod dimesylate.

In some embodiments, the additional therapeutic agent is a IL-15 receptor agonist, such as N-803.

In some embodiments, the additional therapeutic agent is an IL-18 ligand inhibitor, such as tadekinig-alfa.

In some embodiments, the additional therapeutic agent is an IL-22 agonist, such as efmarodocokin alfa, F-652.

In some embodiments, the additional therapeutic agent is an interferon gamma ligand inhibitor, such as emapalumab.

In some embodiments, the additional therapeutic agent is an IL-6 inhibitor, for example tocilizumab, sarilumab, olokizumab, sirukumab, clazakizumab, levilimab or a combination thereof. In some embodiments, the additional therapeutic agent is tocilizumab biosimilar (e.g. CMAB-806).

In some embodiments, the additional therapeutic agent is Apolipoprotein B modulator/IL-6 receptor antagonist/Serum amyloid A protein modulator/Transthyretin modulator. For example, the additional agent is Amilo-5MER.

In some embodiments, the additional therapeutic agent is a Melanocortin MC1/MC3 receptor agonist. For example, the additional therapeutic agent is AP-1189.

In some embodiments, the additional therapeutic agent is a NLRP3 inflammasome inhibitor. In some embodiments, the additional therapeutic agent is dapansutrile, DFV-890.

In some embodiments, the additional therapeutic agent is a nicotinamide phosphoribosyltransferase inhibitors. For example, the additional therapeutic agent is enamptcumab.

In some embodiments, the additional therapeutic agent is a dipeptidase 1 (DPEP-1) inhibitor. For example, the additional therapeutic agent is Metablok (LSALT peptide).

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a TNF alpha ligand inhibitor, such as XPro1595.

In some embodiments, the additional therapeutic agent is a JAK inhibitor, for example the additional therapeutic agent is baricitinib, filgotinib, tofacitinib, olumiant, TD-0903 or a combination thereof. In some examples, the additional therapeutic agent is jaktinib.

In some embodiments, the additional therapeutic agent is an inflammation inhibitor, for example pirfenidon, LYT-100.

In some embodiments, the additional therapeutic agent is anti-inflammatory agent, such as dociparstat sodium, eicosapentaenoic acid, didodecyl methotrexate, rabeximod, EG-009.

In some embodiments, the additional agent is a TREM receptor 1 antagonist.

In some embodiments, the additional therapeutic agent is a CCR1 antagonist, such as MLN-3897.

In some embodiments, the additional therapeutic agent is a Complement C3 inhibitor, such as NGM-621, AMY-101.

In some embodiments, the additional therapeutic agent is a Complement C1s subcomponent inhibitor, such as RLS-0071.

In some embodiments, the additional therapeutic agent is a Complement factor C2 modulator, such as ARGX-117.

In some embodiments, the additional therapeutic agent is a Galectin-3 inhibitor, such as belapectin.

In some embodiments, the additional therapeutic agent is a heparanase inhibitor, such as tridecasodium pixatimod.

In some embodiments, the additional therapeutic agent is an anti-MASP2 antibody, such as narsoplimab.

In some embodiments, the additional therapeutic agent is a calcium channel modulator, such as dantrolene sodium.

In some embodiments, the additional therapeutic agent is a sodium channel stimulator, such as solnatide.

In some embodiments, the additional therapeutic agent is a alkaline phosphatase stimulator such as bovine alkaline phosphatase.

In some embodiments, the additional therapeutic agent is a complement factor D inhibitor, such as ACH-0144471.

In some embodiments, the additional therapeutic agent is a NK1 antagonist, such as LY-686017.

In some embodiments, the additional therapeutic agent is a Zonulin inhibitor, such as larazotide acetate.

In some embodiments, the additional therapeutic agent is a stem cell antigen-1 inhibitor, such as ampion.

In some embodiments, the additional therapeutic agent is a dual complement C5 factor/Leukotriene BLT receptor antagonist, such as nomacopan.

In some embodiments, the additional therapeutic agent is a superoxide dismutase stimulator, such as avasopasem manganese.

In some embodiments, the additional therapeutic agent is an opioid receptor antagonist, such as naltrexone.

In some embodiments, the additional therapeutic agent is an opioid receptor agonist, such as metenkefalin.

In some embodiments, the additional therapeutic agent is a BMP10/BMP15 gene inhibitor, such as lucinactant.

In some embodiments, the additional therapeutic agent is an actin antagonist, such as gelsolin.

In some embodiments, the additional therapeutic agent is a CD95 antagonist, such as asunercept.

In some embodiments, the additional therapeutic agent is a Fractalkine ligand (CX3CL1) inhibitor, such as quetmolimab.

In some embodiments, the additional therapeutic agent is a Platelet glycoprotein VI (GPVI) inhibitor, such as glenzocimab.

In some embodiments, the additional therapeutic agent targets IKKβ and NFκβ, such as OP-101.

In some embodiment, the additional therapeutic agent is a glucocorticoid receptor agonist, such as hydrocortisone, dexamethasone, dexamethasone phosphate.

In some embodiment, the additional therapeutic agent is a PDGF receptor antagonist/TGF beta receptor antagonist/p38 MAP kinase inhibitor, such as deupirfenidone.

In some embodiment, the additional therapeutic agent is a PGD2 antagonist, such as asapiprant.

In some embodiment, the additional therapeutic agent is a prostaglandin E synthase-1 inhibitor, such as sonlicromanol hydrochloride.

In some embodiment, the additional therapeutic agent is a superoxide dismutase modulator, such as Tempol.

In some embodiment, the additional therapeutic agent is a TLR-4 agonist, such as REVTx-99.

In some embodiment, the additional therapeutic agent is a TLR-2/TLR-4 antagonist, such as VB-201.

In some embodiment, the additional therapeutic agent is a TLR-7/TLR-8 antagonist, such as M-5049.

In some embodiments, the additional therapeutic agent is an immunosuppressant, such as tacrolimus, BXT-10, ibudilast, FP-025, apremilast, abatacept, crizanlizumab, itolizumab, bardoxolone methyl.

In some embodiments, the additional therapeutic agent is a RIP-1 kinase inhibitor, such as DNL-758.

In some embodiments, the additional therapeutic agent is an IL-8 receptor antagonist, such as BMS-986253 (HuMax-IL8), DF-1681 (reparixin).

In some embodiments, the additional therapeutic agent is a CD14 inhibitor, such as IC-14, atibuclimab.

In some embodiments, the additional therapeutic agent is a cyclophilin A inhibitor, such as CRV-431.

In some embodiments, the additional therapeutic agent is a Dihydroorotate dehydrogenase (DHODH) inhibitor, such as brequinar, PCT-299, ASLAN-003.

In some embodiments, the additional therapeutic agent is a G-protein coupled bile acid receptor 1 agonist (GPCR19) agonist, such as HY-209.

In some embodiments, the additional therapeutic agent is a Grp78 calcium binding protein inhibitor/Jun N terminal kinase inhibitor/Transferrin modulator/p38 MAP kinase modulator, such as IT-139.

In some embodiments, the additional therapeutic agent is a Histone deacetylase-6 (HDAC-6) inhibitor, such as CKD-506.

In some embodiments, the additional therapeutic agent is a Lyn tyrosine kinase stimulator, such as tolimidone.

In some embodiments, the additional therapeutic agent is a Tek tyrosine kinase receptor stimulator, such as AV-001.

In some embodiments, the additional therapeutic agent is an Integrin alpha-V/beta-1 and alpha-V/beta-6 antagonist, such as PLN-74809.

In some embodiments, the additional therapeutic agent is an IRAK-4 protein kinase inhibitor, such as PF-06650833.

In some embodiments, the additional therapeutic agent is a plasma kallikrein inhibitor/KLKB1 gene inhibitor, such as IONIS-PKK-LRx.

In some embodiments, the additional therapeutic agent is a Leukocyte elastase inhibitor, such as alvelestat, lonodelestat acetate.

In some embodiments, the additional therapeutic is a Maxi K potassium channel inhibitor, such as ENA-001.

In some embodiments, the additional therapeutic is a Nuclear factor kappa B inhibitor/p38 MAP kinase inhibitor, such as GLS-1027.

In some embodiments, the additional therapeutic is a Nuclear factor kappa B inhibitor such as timbetasin, liposomal curcumin.

In some embodiments, the additional therapeutic is anti-fibrotic, such as RT-1840, nintedanib, GB-0139, nintedanib, pamrevlumab.

In some embodiments, the additional therapeutic is a hepatocyte growth factor (HGF) mimetic, such as SNV-003 (ANG-3777).

In some embodiments, the additional therapeutic agent is an A3 adenosine receptor (A3AR) antagonist, for example the additional therapeutic agent is piclidenoson.

In some embodiments, the additional therapeutic agent is an antibiotic for secondary bacterial pneumonia. For example, the additional therapeutic agent is macrolide antibiotics (e.g. azithromycin, clarithromycin, and *Mycoplasma pneumoniae*), fluoroquinolones (e.g. ciprofloxacin, besifloxacin and levofloxacin), tetracyclines (e.g. doxycycline and tetracycline), or a combination thereof. In some embodiments, the antibiotic is XEL 1004. In some embodiments, the antibiotic is eravacycline.

In some embodiments, the additional therapeutic agent is a bactericidal permeability protein inhibitor/Outer membrane protein inhibitor, such as RECCE-327.

In some embodiments, the solid forms disclosed herein are used in combination with pneumonia standard of care (see e.g. Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g. aspirin, ibuprofen (Advil, Motrin IB, others) and acetaminophen (Tylenol, others)). In some embodiments, the additional therapeutic agent is bromhexine anti-cough.

In some embodiments, the solid forms disclosed herein are used in combination with immunoglobulin from cured COVID-19 patients. In some embodiments, the solid forms disclosed herein are used in combination with plasma transfusion. In some embodiments, the solid forms disclosed herein are used in combination with plasma-derived anti-SARS-CoV-2 IgG. In some embodiments, the solid forms disclosed herein are used in combination with TAK-888, NP-028 (anti-SARS-CoV-2 polyclonal hyperimmune globulin (H-IG)), or GC-5131A. In some embodiments, the solid forms disclosed herein are used in combination with COVID-19 convalescent plasma or immunoglobulin. In some embodiments, the solid forms disclosed herein are used in combination with stem cells. For example, in some embodiments, the solid forms disclosed herein are used in combination with AdMSCs, ADR-001, Allo-hMSCs, CAP-1002, hCT-MSC, HB-adMSCs, itMSCs, MultiStem, Pluristem, Remestemcel-L (mesenchymal stem cells), NurOwn®, Rexlemestrocel-L, UCMSCs, or ACT-20.

In some examples, the additional therapeutic agent is an TLR agonist. Examples of TLR agonists include, but are not limited to, vesatolimod (GS-9620), GS-986, IR-103, lefitolimod, tilsotolimod, rintatolimod, polyinosinic-polycytidylic Acid (poly I:C), DSP-0509, AL-034, G-100, MT-2766, cobitolimod, AST-008, motolimod, GSK-1795091, GSK-2245035, VTX-1463, GS-9688, LHC-165, BDB-001, RG-7854, telratolimod.RO-7020531. In some embodiments the additional therapeutic agent is PUL-042.

In some examples, the additional therapeutic agent is selected from the group consisting of AVM-0703, bortezomid, flurazepam, ponatinib, sorafenib, paramethasone, clocortolone, flucloxacillin, sertindole, clevidipine, atorvastatin, simvastatin, trimodulin, rosuvastatin, cinolazepam, clofazimine, fosaprepitant, and combinations thereof.

In some examples, the additional therapeutic agent is carrimycin, suramin, triazavirin, dipyridamole, bevacizumab, meplazumab, GD31 (*Rhizobium*), NLRP inflammasome inhibitor, or α-ketoamine.

In some embodiments, the additional therapeutic agent is viral macrophage inflammatory protein (vMIP).

In some embodiments, the additional therapeutic agent is a recombinant human angiotensin-converting enzyme 2 (rhACE2), for example alunacedase alfa (APN-01), HLX- 71. In some embodiments, the additional therapeutic agent is an angiotensin II receptor agonist. In some examples, the additional therapeutic agent is a partial agonist of AT2 or a partial antagonist of AT1. In some embodiments, the additional therapeutic agent is L-163491. In some embodiments, the additional therapeutic agent is valsartan, losartan, candesartan, eprosartan, irbesartan, olmesartan. In some embodiments, the additional therapeutic agent is VP-01, TXA-127. In some embodiments, the additional therapeutic agent is telmisartan.

In some embodiments, the additional therapeutic agent is an ACE inhibitor, such as ramipril, captopril, enalapril, lisonopril.

In some embodiments, the additional therapeutic agent is an Angiotensin II AT-1 receptor antagonist/Beta-arrestin stimulator, such as TRV-027.

In some embodiments, the additional therapeutic agent is an ACE2 inhibitor/COVID19 Spike glycoprotein inhibitor, such as MP-0420.

In some embodiments, the additional therapeutic agent is a caspase inhibitor, such as emricasan.

In some embodiments, the additional therapeutic agent is an acetaldehyde dehydrogenase inhibitor, such as ADX-629.

In some embodiments, the additional therapeutic agent is a dihydroorotate dehydrogenase inhibitor, such as RP-7214.

In some embodiments, the additional therapeutic agent is a dihydroorotate dehydrogenase inhibitor; Protein tyrosine kinase inhibitor, such as repurposed leflunomide.

In some embodiments, the additional therapeutic agent is an aldose reductase inhibitor, such as AT-001.

In some embodiments, the additional therapeutic agent is a platelet inhibitor. For example, the additional therapeutic agent is dipyridamole.

In some embodiments, the additional therapeutic agent is an anti-coagulant, such as heparins (heparin and low molecular weight heparin), aspirin, apixaban, dabigatran, edoxaban, argatroban, enoxaparin, fondaparinux.

In some embodiments, the additional therapeutic agent is a tissue factor inhibitor, such as AB-201.

In some embodiments, the additional therapeutic is a Factor XIIa antagonist, such as garadacimab.

In some embodiments, the additional therapeutic is a Factor XIa antagonist, such as EP-7041.

In some embodiments, the additional therapeutic agent is a VE-PTP inhibitor, such as razuprotafib.

In some embodiments, the additional therapeutic agent is a VIP 2 receptor agonist, such as PB-1046.

In some embodiments, the additional therapeutic agent is an anti-thrombotic, such as defibrotide, rivaroxaban, alteplase, tirofiban, clopidogrel, prasugrel, bemiparin, bivalirudin, sulodexide, tenecteplase.

In some embodiments, the additional therapeutic agent is a vasodilator, such as iloprost, ventaprost, vazegepant, angiotensin 1-7, ambrisentan, NORS, pentoxifylline, propranolol, RESP301, sodium nitrite.

In some embodiments, the additional therapeutic agent is a blood clotting modulator, such as lanadelumab.

In some embodiments, the additional therapeutic agent is a diuretic, such as an aldosterone antagonist, such as spironolactone.

In some embodiments, the additional therapeutic agent is antihypoxic, such as trans-sodium crocetinate.

In some embodiments, the additional therapeutic agent is MK-5475.

In some embodiments, the additional therapeutic agent is a hypoxia-inducible factor (HF) prolyl hydroxylase-2 (PHD-2) inhibitor such as desidustat, vadadustat.

In some embodiments, the additional therapeutic agent is a renin inhibitor, such as aliskiren.

In some embodiments, the additional therapeutic agent is a calcium channel inhibitor such as nifedipine.

In some embodiments, the additional therapeutic agent is a chelating agent, such as desferal, deferiprone, deferoxamine.

In some embodiments, the additional therapeutic agent is a Retinoic acid receptor agonist, such as isotretinoin, or fenretinide.

In some embodiments, the additional therapeutic agent is an AMPA receptor modulator, such as traneurocin (Nanomedivir).

In some embodiments, the additional therapeutic agent is a human antimicrobial peptide, such as LL-37i.

In some embodiments, the additional therapeutic agent is a microbiome modulator, such as EDP-1815, KB-109.

In some embodiments, the additional therapeutic agent is an estrogen receptor antagonist, such as tamoxifen.

In some embodiments, the additional therapeutic agent is an estrogen receptor modulator, such as estetrol.

In some embodiments, the additional therapeutic agent is an androgen receptor antagonist such as bicalutamide, enzalutamide, proxalutamide.

In some embodiments, the additional therapeutic agent is a GNRH receptor antagonist, such as degarelix.

In some embodiments, the additional therapeutic agent is a sex hormone modulator, such as dutasteride.

In some embodiments, the additional therapeutic agent is a thyroid hormone receptor, such as sobetirome.

In some embodiments, the additional therapeutic agent is a calpain inhibitor, such as BLD-2660.

In some embodiments, the additional therapeutic agent is a GM-CSF ligand inhibitor such as gimsilumab, lenzilumab, namilumab, TJM2, otilimab, plonmarlimab.

In some embodiments, the additional therapeutic agent is a GM-CSF receptor antagonist, such as mavrilimumab.

In some embodiments, the additional therapeutic agent is a GM-CSF receptor agonist, such as sargramostim.

In some embodiments, the additional therapeutic agent is an alpha 1 adrenoreceptor antagonist such as prazosin.

In some embodiments, the additional therapeutic agent is a neuropilin 2 inhibitor, such as ATYR-1923.

In some embodiments, the additional therapeutic agent is an activated calcium (CRAC) channel inhibitor, such as CM-4620.

In some embodiments, the additional therapeutic agent is a calcium activated chloride channel (CACC) inhibitor, such as crofelemer.

In some embodiments, the additional therapeutic agent is a proto-oncogene Mas agonist, such as BIO-101.

In some embodiments, the additional therapeutic agent is a DPP4 inhibitor, such as saxagliptin, sitagliptin, alogliptin, linagliptin.

In some embodiments, the additional therapeutic agent is a sodium glucose cotransporter type 2 (SGLT-2) inhibitor such as dapagliflozin propanediol.

In some embodiments, the additional therapeutic agent is a fractalkine receptor inhibitor such as KAND-567.

In some embodiments, the additional therapeutic agent is an alpha2-receptor agonist. For example, the additional therapeutic agent is dexmedetomidine.

In some embodiments, the additional therapeutic agent is a mCBM40 (multivalent carbohydrate-binding module Family 40 domain) product, for example the additional therapeutic agent is Neumifil.

In some embodiments, the additional therapeutic agent is a histamine H1 receptor antagonist, such as ebastine, tranilast.

In some embodiments, the additional therapeutic agent is a histamine H2 receptor antagonist, such as famotidine.

In some embodiments, the additional therapeutic agent is anti-histamine such as cloroperastine, and clemastine.

In some embodiments, the additional therapeutic agent is a vasoactive intestinal peptide receptor 1 agonists, such as aviptadil.

In some embodiments, the additional therapeutic agent is a drug that treats acute respiratory distress syndrome (ARDS), such as FX-06.

In some embodiments, the additional therapeutic agent is BIG-11006.

In some embodiments, the additional therapeutic agent is sodium pyruvate.

In some embodiments, the additional therapeutic agent is LEAF-4L6715, LEAF-4L7520.

In some embodiments, the additional therapeutic agent is a respiratory stimulant, such as almitrine.

In some embodiments, the additional therapeutic agent is a bronchodilator, such as brensocatib, formoterol.

In some embodiments, the additional therapeutic agent is a beta 2 adrenoceptor agonist, such as salmeterol.

In some embodiments, the additional therapeutic agent is hyaluronidase inhibitor such as astodrimer.

In some embodiments, the additional therapeutic agent is an anti-LIGHT antibody, such as CERC-002.

In some embodiments, the additional therapeutic agent is a CRAC (calcium release-activated calcium) channel inhibitor, such as CM-4620-IE.

In some embodiments, the additional therapeutic agent is a TLR4 antagonist, such as EB-05, NI-0101, or E-5564.

In some embodiments, the additional therapeutic agent is a deoxyribonuclease I stimulator, such as GNR-039.

In some embodiments, the additional therapeutic agent is an ornithine decarboxylase inhibitor, such as eflornithine.

In some embodiments, the solid forms described herein are used in combination with respiratory-specific small interfering RNA therapies. In some embodiments, these therapies are delivered by a nebulizer.

In some embodiments, the additional therapeutic agent is a vimentin modulator. For example, the additional therapeutic agent is pritumumab, hzVSF-v13.

In some embodiments, the additional therapeutic agent is a modulator of Nsp15 (nonstructural protein 15) such as benzopurpurin B, C-467929, C-473872, AB001, NSC-306711 and N-65828.

In some embodiments, the additional therapeutic agent is a xanthine dehydrogenase inhibitor, such as oxypurinol (XRx-101).

In some embodiments, the additional therapeutic agent is a xanthine oxidase inhibitor, such as bucillamine, Xrx-101.

In some embodiments, the additional therapeutic agent is a cathepsin inhibitor, such as VBY-825, ONO-5334.

In some embodiments, the additional therapeutic agent is a Transforming growth factor beta (TGF-β) inhibitor. For example, the additional therapeutic agent is OT-101.

In some embodiments, the additional therapeutic agent is a N-methyl-D-aspartate (NMDA) receptor antagonist. For example, the additional therapeutic agent is ifenprodil, transcrocetin.

In some embodiments, the additional therapeutic agent is a glycolysis inhibitor. For example, the additional therapeutic agent is WP-1122.

In some embodiments, the additional therapeutic is a Leukotriene D4 antagonist, such as montelukast.

In some embodiments, the additional therapeutic is a Leukotriene BLT receptor antagonist, such as ebselen.

In some embodiments, the additional therapeutic is a tubulin inhibitor, such as VERU-111, colchicine.

In some embodiments, the additional therapeutic agent is a glucosylceramide synthase inhibitor such as miglustat.

In some embodiments, the additional therapeutic agent is a Nrf2 activator, such as PB125.

In some embodiments, the additional therapeutic agent is a Rev protein modulator, such as ABX464.

In some embodiments, the additional therapeutic agent is a nuclear import inhibitor, such as iCP-NI (CV-15).

In some embodiments, the additional therapeutic agent is a cannabinoid CB2 receptor agonist, such as PPP003.

In some embodiments, the additional therapeutic agent is a dehydropeptidase-1 modulator, such as LSALT peptide.

In some embodiments, the additional therapeutic agent is a cyclooxygenase inhibitor, such as celecoxib, naproxen, aspirin/dipyridamole.

In some embodiments, the additional therapeutic agent is an antitoxin such as CAL02.

In some embodiments, the additional therapeutic agent is a nitric oxide stimulant, such as GLS-1200.

In some embodiments, the additional therapeutic agent is an apelin receptor agonist, such as CB-5064.

In some embodiments, the additional therapeutic agent is a complement inhibitor, such as ravulizumab.

In some embodiments, the additional therapeutic agent is a Colony-stimulating factor 1 receptor (CSF1R) inhibitor, such as axatilimab.

In some embodiments, the additional therapeutic agent is a complement C5 factor inhibitor, such as eculizumab, zilucoplan, and C5a such as BDB-001, IFX-1, advoralimab, In some embodiments, the additional therapeutic agent is a complement C1s inhibitor, such as conestat alpha.

In some embodiment, the additional therapeutic agent is a C3 inhibitor, such as APL-9, AMY-101

In some embodiments, the additional therapeutic agent is an anti-C5aR antibody, such as advoralimab or vilobelimab.

In some embodiments, the additional therapeutic agent is an anti elongation factor 1 alpha 2 inhibitor, such as plitidepsin.

In some embodiments, the additional therapeutic agent is an angiopoietin ligand-2 inhibitor, such as LY-3127804.

In some embodiments, the additional therapeutic agent is a lysine specific histone demethylase 1 inhibitor, such as vafidemstat.

In some embodiments, the additional therapeutic agent is a histone inhibitor, such as STC-3141.

In some embodiments, the additional therapeutic agent is a hyaluronan inhibitor.

In some embodiments, the additional therapeutic agent is dopamine D2 receptor antagonist, such as chlorpromazine.

In some embodiments, the additional therapeutic agent is a proton pump inhibitor, such as omeprazole.

In some embodiments, the additional therapeutic agent is a PGI2 agonist, such as epoprostenol.

In some embodiments, the additional therapeutic agent is a plasminogen activator inhibitor 1 inhibitor, such as TM-5614.

In some embodiments, the additional therapeutic agent is a Ubiquinol cytochrome C reductase 14 kDa inhibitor, such as telacebec.

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

In some embodiments, the additional therapeutic or prophylactic agent is molnupiravir, oseltamivir, nirmatrelvir, or ritonavir. In some embodiments, the additional therapeutic or prophylactic agent is ritonavir or cobicistat. In some embodiments, the additional therapeutic or prophylactic agent is molnupiravir. In some embodiments, the additional therapeutic or prophylactic agent is molnupiravir, oseltamivir, nirmatrelvir, or ritonavir. In some embodiments, the additional therapeutic or prophylactic agent comprises nirmatrelvir and ritonavir. In some embodiments, the additional therapeutic or prophylactic agent comprises nirmatrelvir and cobicistat.

In some embodiments, the additional therapeutic agent is a cell therapy, such as allogeneic natural killer cells, antigen presenting cells (APC), invariant natural killer T (iNKT) cells, induced pluripotent stem cell (iPSC), allogeneic T-cells, autologous adipose-derived mesenchymal stem cells, allogeneic bone marrow-derived mesenchymal stem cells, allogeneic mesenchymoangioblast-derived mesenchymal stem cells, regulatory T cells (Tregs), dendritic cells. In some embodiments, the additional therapeutic agent is SARS-CoV-2 specific cytotoxic T lymphocyte. In some embodiments, the additional therapeutic agent is agenT-797, Allocetra, ALVR-109, BM-Allo-MSC, CAStem, Cellgram-AKI, CK-0802, CL-2020, IL-15-NK cells, NKG2D-CAR-NK cells, ACE2 CAR-NK cells, DWP-710, partially HLA-matched Virus Specific T cells (VSTs), FT-516, RAPA-501, SARS-CoV-2 Specific T Cells, HLCM-051, ExoFlo, HCR-040, it-hMSC, KI-MSC-PL-205, ORBCEL-C, pathogen-specific aAPC, ProTrans, SBI-101, StemVacs, STI-8282, taniraleucel, UMSC-01.

In some embodiments, the additional therapeutic agent is selected from the group consisting of ABBV-744, dBET6, MZ1, CPI-0610, Sapanisertib, Rapamycin, Zotatifin, Verdinexor, Chloroquine, Dabrafenib, WDB002, Sanglifehrin A, FK-506, Pevonedistat, Ternatin 4, 4E2RCat, Tomivosertib, PS3061, IHVR-19029, XC-7, long-acting injectable ivermectin, Captopril, Lisinopril, Camostat, Chloramphenicol, Tigecycline, Linezolid, and combinations thereof.

In some embodiments, the additional therapeutic agent is selected form a group consisting of tilorone, cannabidiol, cyclosporine, loperamide, mefloquine, amodiaquine, proscillaridin, digitoxin, digoxin, hexachlorophene, hydroxyprogesterone caproate, salinomycin, ouabain, cepharanthine, ciclesonide, oxyclozanide, anidulafungin, gilteritinib, berbamine, tetrandrine, abemaciclib, ivacaftor, bazedoxifene, niclosamide, eltrombopag, and combinations thereof.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, ISPM-19, cipargamin, artemisone, and combinations thereof.

It is also possible to combine any solid form of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a solid form of the disclosure with one or more other active therapeutic agents generally refers to simultaneous or sequential administration of a solid form of the disclosure and one or more other active therapeutic agents, such that therapeutically effective amounts of the solid form of the disclosure and one or more other active therapeutic agents are both present in the body of the patient.

Co-administration includes administration of unit dosages of the solid forms of the disclosure before or after administration of unit dosages of one or more other active therapeutic agents, for example, administration of the solid forms of the disclosure within seconds, minutes, or hours of the administration of one or more other active therapeutic agents. For example, a unit dose of a solid form of the disclosure can be administered first, followed within seconds or minutes by administration of a unit dose of one or more other active therapeutic agents. Alternatively, a unit dose of one or more other therapeutic agents can be administered first, followed by administration of a unit dose of a solid form of the disclosure within seconds or minutes. In some cases, it may be desirable to administer a unit dose of a solid form of the disclosure first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a solid form of the disclosure.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect, which is greater than the predicted purely additive effects of the individual compounds of the combination.

Combination Therapy for the Treatment of Pneumoviridae

The solid forms provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-OOVP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

Combination Therapy for the Treatment of Picornaviridae

The solid forms provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

Combination Therapy for Respiratory Infections

Many of the infections of the Pneumoviridae, Picornaviridae, and Coronaviridae viruses are respiratory infections. Therefore, additional active therapeutics used to treat respiratory symptoms and sequelae of infection may be used in combination with the solid forms provided herein. The additional agents are preferably administered orally or by direct inhalation. For example, other preferred additional therapeutic agents in combination with the solid forms provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the solid forms provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumethasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the solid forms provided herein for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the solid forms provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the solid forms provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the solid forms provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The solid forms provided herein may also be combined with mucolytic agents to treat both the infection and symptoms of respiratory infections. A non-limiting example of a mucolytic agent is ambroxol. Similarly, the solid forms may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J. Pediatrics 2007, 266). Thus, the solid forms provided herein may also be combined with nebulized hypertonic saline particularly when the virus infection is complicated with bronchiolitis. The combination of the solid forms provided herein with hypertonic saline may also comprise any of the additional agents discussed above. In one embodiment, nebulized about 3% hypertonic saline is used.

Combination Therapy for the Treatment of Flaviviridae Virus Infections

The solid forms provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

Combination Therapy for the Treatment of Filoviridae Virus Infections

The solid forms provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The solid forms provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The solid forms provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

The invention will be described in greater detail by way of specific examples. The following examples are offered for illustrative purposes and are not intended to limit the invention in any manner. Those of skill in the art will readily recognize a variety of non-critical parameters, which can be changed or modified to yield essentially the same results.

EXAMPLES

General Procedures

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Differential Scanning Calorimetry (DSC) data were collected using a TA Instruments Q2000 differential scanning calorimeter. Temperature calibration was performed using NIST-traceable indium metal. The sample was placed into a Tzero aluminum DSC pan, covered with a lid pierced using a needle. The weight was then accurately recorded. A weighed aluminum pan configured as the sample pan was placed on the reference side of the cell. The sample was heated from 20° C. to 300° C. at 10° C./minute.

Thermogravimetric Analysis (TGA) data were collected using a TA Instruments Q5000 thermogravimetric analyzer. Temperature calibration was performed using nickel and Alumel™. Each sample was placed in an aluminum pan and inserted into the TG furnace. The furnace was heated under a nitrogen purge. The sample was heated from ambient to 300° C. at 10° C./minute.

Example 1. Compound of Formula (I) Ethanol Solvate Form E1

Compound of Formula (I) Ethanol Solvate Form E1 was first prepared by slurrying about 50 mg of poorly crystalline compound of Formula (I) in about 0.4 mL of ethanol. A clear solution was obtained. About 100 mg of poorly crystalline compound of Formula (I) was added. A slurry was obtained. The slurry was stirred at ambient temperature for about a day. The solids were filtered by centrifugation and the wet solids (ethanol solvate Form E1) were characterized by X-ray.

Compound of Formula (I) Ethanol Solvate Form E1 was also prepared by slurrying about 3 g of poorly crystalline compound of Formula (I) in about 9 mL of ethanol. The mixture was heated to about 50° C. to afford a slurry. An additional 3 mL of ethanol was added and the slurry was cooled to ambient temperature with magnetic stirring. To the slurry, 12 mL of heptane was added over a period of about 6 hours. The resulting slurry was filtered and the wet cake was characterized by X-Ray as ethanol solvate Form E1. After vacuum drying in the oven at about 50° C. for about a day, the dry cake was characterized again by X-ray. The XRPD pattern of the resulting dry solid matches the XRPD pattern of Form I (see Example 2 below).

Compound of Formula (I) ethanol solvate Form E1 is a solvated phase. Its XRPD pattern is shown in FIG. 1 and is characterized by Tier 1 reflections at 5.4°, 15.2°, and 23.8° 2θ, but also Tier 2 at 12.9°, 18.7°, and 25.2° 2θ, and Tier 3 at 14.0°, 16.8°, and 24.0° 2θ. A list of 2-theta peaks is provided below:

TABLE 1

XRPD peak list for crystalline compound of Formula (I) ethanol solvate Form E1 by tiers

| Tier 1 | | Tier 2 | | Tier 3 | |
|---|---|---|---|---|---|
| Position °2θ | Relative Intensity (%) | Position °2θ | Relative intensity (%) | Position °2θ | Relative intensity (%) |
| 5.4 | 100 | 12.9 | 6 | 14.0 | 7 |
| 15.2 | 81 | 18.7 | 25 | 16.8 | 15 |
| 23.8 | 7 | 25.2 | 19 | 24.0 | 12 |

TABLE 2

Complete XRPD peak list for crystalline compound of Formula (I) ethanol solvate Form E1

| Pos. [°2Th.] | Rel. Int. [%] |
|---|---|
| 5.4 | 100 |
| 10.4 | 1 |
| 10.8 | 7 |
| 12.9 | 6 |
| 14.0 | 7 |
| 14.8 | 5 |
| 15.2 | 81 |
| 16.2 | 3 |
| 16.8 | 15 |
| 18.7 | 25 |
| 19.1 | 7 |
| 19.4 | 8 |
| 20.0 | 3 |
| 20.1 | 4 |
| 20.9 | 6 |
| 21.6 | 6 |
| 22.1 | 8 |
| 22.9 | 8 |
| 23.8 | 7 |
| 24.0 | 12 |
| 24.4 | 7 |
| 25.2 | 19 |
| 26.2 | 9 |
| 27.1 | 6 |

TABLE 2-continued

| Complete XRPD peak list for crystalline compound of Formula (I) ethanol solvate Form E1 | |
|---|---|
| Pos. [°2Th.] | Rel. Int. [%] |
| 27.5 | 7 |
| 28.5 | 1 |
| 29.0 | 2 |
| 30.0 | 1 |
| 31.6 | 2 |
| 32.3 | 2 |
| 33.4 | 2 |
| 34.0 | 1 |
| 35.3 | 3 |
| 35.8 | 2 |
| 36.4 | 1 |
| 36.9 | 2 |
| 37.4 | 1 |
| 38.1 | 1 |

Example 2. Crystalline Form I of the Compound of Formula (I)

Compound of Formula (I) Form I was first prepared by slurrying about 50 mg of poorly crystalline compound of Formula (I) in about 0.4 mL of water. The resulting slurry was stirred at ambient temperature for about a day. The solids were filtered by centrifugation and the wet solids were characterized by X-ray. Form I was obtained by vacuum drying the solids in the oven at 50° C. for about a day. The XRPD patterns of the wet and dry solids were identical, indicating no solvent/water loss during the drying process.

Compound of Formula (I) Form I was also prepared by slurrying about 50 mg of poorly crystalline compound of Formula (I) in about 1 mL of ethanol/water mixture (5/95 v/v). The resulting slurry was stirred at ambient temperature for about a day. The solids were filtered by centrifugation and the wet solids were characterized by X-ray. Form I was obtained as a wet cake. After vacuum drying in the oven at about 50° C. for about a day, the dry cake was characterized again by X-ray. The XRPD patterns of the wet and dry solids were identical, indicating no solvent/water loss during the drying process.

Compound of Formula (I) Form I can also be obtained by vacuum drying ethanol solvate Form E1 (Example 1) in the oven at about 50° C. for about a day.

Compound of Formula (I) Form I is an unsolvated phase. Its XRPD pattern is shown in FIG. 2 and is characterized by Tier 1 reflections at 5.3°, 18.7°, and 20.0° 2θ, but also Tier 2 at 14.3°, 15.4°, and 25.1° 2θ, and Tier 3 at 14.6°, 17.0°, and 25.9° 2θ. A list of 2-theta peaks is provided below:

TABLE 3

| XRPD peak list for compound of Formula (I) Form I by tiers | | | | | |
|---|---|---|---|---|---|
| Tier 1 | | Tier 2 | | Tier 3 | |
| Position °2θ | Relative Intensity (%) | Position °2θ | Relative Intensity (%) | Position °2θ | Relative Intensity (%) |
| 5.3 | 100 | 14.3 | 6 | 14.6 | 6 |
| 18.7 | 13 | 15.4 | 54 | 17.0 | 9 |
| 20.0 | 8 | 25.1 | 6 | 25.9 | 6 |

TABLE 4

| Complete XRPD peak list for compound of Formula (I) Form I | |
|---|---|
| Pos. [°2Th.] | Rel. Int. [%] |
| 5.3 | 100 |
| 10.3 | 1 |
| 10.6 | 2 |
| 12.8 | 4 |
| 13.2 | 1 |
| 13.5 | 1 |
| 14.3 | 6 |
| 14.6 | 6 |
| 15.4 | 54 |
| 15.8 | 1 |
| 16.6 | 4 |
| 17.0 | 9 |
| 18.7 | 13 |
| 19.6 | 6 |
| 20.0 | 8 |
| 20.7 | 3 |
| 21.0 | 4 |
| 21.2 | 5 |
| 22.1 | 5 |
| 22.8 | 3 |
| 23.5 | 1 |
| 24.6 | 4 |
| 25.1 | 6 |
| 25.2 | 5 |
| 25.9 | 6 |
| 26.6 | 3 |
| 26.9 | 5 |
| 27.4 | 1 |
| 28.1 | 3 |
| 28.6 | 2 |
| 29.4 | 1 |
| 29.8 | 1 |
| 30.0 | 1 |
| 30.9 | 2 |
| 31.3 | 2 |
| 32.1 | 1 |
| 32.6 | 1 |
| 33.1 | 2 |
| 33.8 | 1 |
| 34.3 | 1 |
| 34.7 | 2 |
| 35.4 | 2 |
| 37.2 | 2 |
| 37.7 | 1 |
| 38.1 | 1 |

The DSC thermogram is shown in FIG. 3 and exhibits an endothermic transition with an onset at about 162° C. The TGA thermogram is shown in FIG. 4 and indicates that this phase is unsolvated (free of solvent).

Example 3. Compound of Formula (I) Acetonitrile Solvate Form ACN1

Compound of Formula (I) acetonitrile solvate Form ACN1 was first prepared by slurrying poorly crystalline compound of Formula (I) in acetonitrile: about 0.4 mL of acetonitrile was added to about 50 mg of poorly crystalline compound of Formula (I). A clear solution was obtained. About 85 mg of poorly crystalline compound of Formula (I) was added to that solution, resulting in a slurry. The slurry was stirred at ambient temperature for about a day. The solids were then isolated by centrifugation and the wet solids (ACN1) were characterized by X-Ray.

Compound of Formula (I), Acetonitrile solvate Form ACN1 is a solvated phase. Its XRPD pattern is shown in FIG. 5 and is characterized by Tier 1 reflections at 4.6, 14.6, and 18.3° 2θ, but also Tier 2 at 5.0, 15.7, and 26.2° 2θ, and Tier 3 at 8.3, 16.6, and 17.5° 2θ. A list of 2-theta peaks is provided below:

TABLE 5

| XRPD peak list for compound of Formula (I) acetonitrile solvate Form ACN1 by tiers | | | | | |
|---|---|---|---|---|---|
| Tier 1 | | Tier 2 | | Tier 3 | |
| Position °2θ | Relative intensity (%) | Position °2θ | Relative intensity (%) | Position °2θ | Relative intensity (%) |
| 4.6 | 100 | 5.0 | 11 | 8.3 | 5 |
| 14.6 | 9 | 15.7 | 5 | 16.6 | 5 |
| 18.3 | 6 | 26.2 | 4 | 17.5 | 3 |

TABLE 6

| Complete XRPD peak list for compound of Formula (I) acetonitrile solvate Form ACN1 | |
|---|---|
| Pos. [°2Th.] | Rel. Int. [%] |
| 4.6 | 100 |
| 5.0 | 11 |
| 5.5 | 1 |
| 8.3 | 5 |
| 10.5 | 2 |
| 11.1 | 1 |
| 12.2 | 1 |
| 13.2 | 1 |
| 13.6 | 2 |
| 13.8 | 3 |
| 14.1 | 1 |
| 14.6 | 9 |
| 15.2 | 3 |
| 15.7 | 5 |
| 16.2 | 3 |
| 16.6 | 5 |
| 16.9 | 2 |
| 17.5 | 3 |
| 17.7 | 2 |
| 18.3 | 6 |
| 20.4 | 1 |
| 20.7 | 2 |
| 21.1 | 1 |
| 21.7 | 1 |
| 22.1 | 1 |
| 22.3 | 1 |
| 24.8 | 1 |
| 25.7 | 3 |
| 26.2 | 4 |
| 27.1 | 2 |
| 27.8 | 1 |
| 29.5 | 1 |
| 30.7 | 1 |
| 32.3 | 1 |
| 35.4 | 1 |

Example 4. Compound of Formula (I) Form II

Compound of Formula (I) Form II was obtained by vacuum drying the wet solids (Form ACN1, Example 3) in the oven at about 50° C.

Compound of Formula (I) Form II is a desolvated phase after acetonitrile is removed from Form ACN1 (Example 3) through drying. Its XRPD pattern is shown in 6 and is characterized by Tier 1 reflections at 5.1, 10.3, and 15.2° 2θ, but also Tier 2 at 14.7, 17.3, and 26.2° 2θ, and Tier 3 at 11.4, 13.8, and 25.8° 2θ. A list of 2-theta peak is shown below.

TABLE 7

| XRPD peak list for compound of Formula (I) Form II by tiers | | | | | |
|---|---|---|---|---|---|
| Tier 1 | | Tier 2 | | Tier 3 | |
| Position °2θ | Relative intensity (%) | Position °2θ | Relative intensity (%) | Position °2θ | Relative intensity (%) |
| 5.1 | 100 | 14.7 | 7 | 11.4 | 3 |
| 10.3 | 10 | 17.3 | 7 | 13.8 | 3 |
| 15.2 | 11 | 26.2 | 7 | 25.8 | 4 |

TABLE 8

| Complete XRPD peak list for compound of Formula (I) Form II | |
|---|---|
| Pos. [°2Th.] | Rel. Int. [%] |
| 5.1 | 100 |
| 10.2 | 2 |
| 10.3 | 10 |
| 11.4 | 3 |
| 12.9 | 1 |
| 13.8 | 3 |
| 14.7 | 7 |
| 15.2 | 11 |
| 16.4 | 5 |
| 16.7 | 5 |
| 17.3 | 7 |
| 18.2 | 2 |
| 20.1 | 3 |
| 20.8 | 2 |
| 23.7 | 1 |
| 24.6 | 1 |
| 25.8 | 4 |
| 26.2 | 7 |
| 26.8 | 1 |
| 27.8 | 1 |
| 30.4 | 1 |
| 33.8 | 2 |
| 35.0 | 1 |
| 37.0 | 1 |

The DSC thermogram of compound of Formula (I) Form II is shown in FIG. 7 and exhibits a first endothermic transition at about 149° C. followed by an immediate exotherm, indicating a melting/recrystallization transition, at 153° C. A second endotherm is observed with an onset at about 161° C. The TGA thermogram is of compound of Formula (I) Form II shown in FIG. 8 and indicates that this phase is desolvated (free of solvent).

Example 5. Compound of Formula (I) Solvate in Other Organic Solvents and Other Desolvated Forms Examples 1 and 3 are examples of compound of Formula (I) freebase forming multiple solvated forms in a particular process solvent (acetonitrile and Ethanol). The labile nature of the solvents in the solvated forms means the solvents can be readily removed by drying operation (vacuum or temperature or both). Each solvated form could lead to a specific desolvated form. For instance, Form II (Example 4) is the corresponding desolvated form of ACN1 (Example 3).

Due to the unique chemical structure of the compound of Formula (I), the molecule has a propensity to form many forms of hydrates and solvates, as well as the corresponding desolvated and dehydrated forms. These include, but are not limited to, organic solvents such as methanol, ethanol, isopropanol, 1-butanol, 2-butanol (e.g. (S)-2-butanol and (R)-2-butanol), acetone, acetonitrile, ethyl acetate, propyl acetate (e.g. isopropyl acetate), butyl acetate, methyl t-butyl ether (MTBE), tetrahydrofuran, toluene, 1-butanone (methyl ethyl ketone), 2-methyl tetrahydrofuran, heptane (e.g. n-heptane), cyclohexane, cyclopentyl methyl ether, dichloromethane, N,N-dimethylacetamide, N,N-dimethylformamide, ethyleneglycol, hexane (e.g. n-hexane), propylene glycol, methyl butyl ketone, methylcyclohexane, methylisobutylketone, N-methylpyrrolidone, t-butyl alcohol, acetic acid, anisole, dimethyl sulfoxide, isobutyl acetate, methyl acetate, 2-methyl-1-propanol, ethyl ether, ethyl formate, formic acid, pentane (e.g. n-pentane), 1-pentanol, and triethylamine.

The unique chemical structure of the compound of Formula (I) also implies the likelihood of forming numerous cocrystals with coformers, as well as crystalline salt forms if the pKa differential between compound of Formula (I) and the counterion is sufficient to enable proton transfer (salt formation). These may include, but are not limited to, acids such as acetic acid, adipic acid, alginic acid, ascorbic acid, aspartic acid, benzenesulfonic acid, benzoic acid, camphoric acid, camphor-10-sulfonic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, D-glucoheptonic acid, D-gluconic acid, D-glucuronic acid, glutamic acid, glutaric acid, glycolic acid, hippuric acid, hydrochloric acid, isobutyric acid, lactic acid, lauric acid, maleic acid, malic acid, malonic acid, mandelic acid, methanesulfonic acid, mucic acid, naphthalene-1,5-disulfonic acid, naphthalene-2-sulfonic acid, nicotinic acid, oleic acid, orotic acid, oxalic acid, palmitic acid, pamoic acid, phosphoric acid, propionic acid, pyroglutamic acid, salicylic acid, sebacic acid, stearic acid, succinic acid, sulfuric acid, tartaric acid, thiocyanic acid, and p-toluenesulfonic acid.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

We claim:

1. A solvate of a compound of Formula (I):

Formula (I)

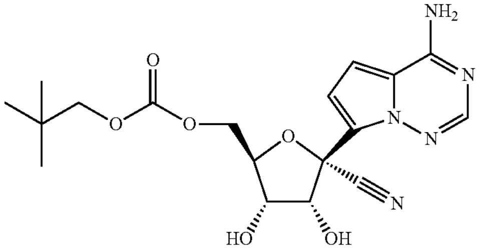

wherein the solvate is an organic solvent solvate or hydrate.

2. The solvate of claim 1, wherein the solvate is an ethanol solvate or an acetonitrile solvate.

3. The solvate of claim 1, wherein the solvate is crystalline.

4. A pharmaceutical composition comprising:

(i) a solvate of claim 1; and (ii) a pharmaceutically acceptable excipient.

5. A method of making the solvate of claim 1 wherein the method comprises (i) slurrying the compound of Formula (I) in a solvent and (ii) isolating the solvate or the crystalline form of Formula (I).

6. A crystalline form of an ethanol solvate of a compound of Formula (I)

Formula (I)

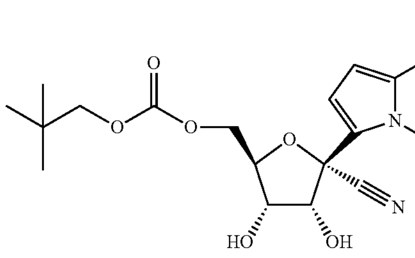

wherein the crystalline form is characterized by an XRPD pattern comprising degree 2θ-reflections (±0.2 degrees 2θ) at 5.4°, 15.2°, and 23.8°.

7. The crystalline form of claim 6, wherein the XRPD pattern comprises degree 2θ-reflections (±0.2 degrees 2θ) at 5.4°, 12.9°, 15.2°, 18.7°, 23.8° and 25.2.

8. The crystalline form of claim 6, wherein the XRPD pattern comprises degree 2θ-reflections (±0.2 degrees 2θ) at 5.4°, 12.9°, 14.0°, 15.2°, 16.8°, 18.7°, 23.8°, 24.0°, and 25.2°.

9. A pharmaceutical composition comprising:

(i) the crystalline form of claim 6; and (ii) a pharmaceutically acceptable excipient.

10. A method of making the crystalline form of claim 6, wherein the method comprises (i) slurrying the compound of Formula (I) in a solvent and (ii) isolating the solvate or the crystalline form of Formula (I).

11. A crystalline form of an acetonitrile solvate of a compound of Formula (I):

Formula (I)

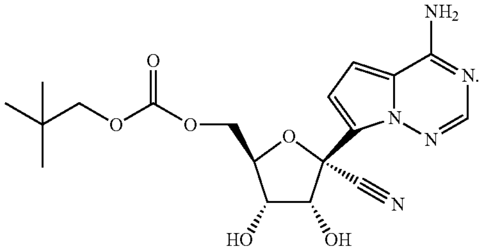

wherein the crystalline form is characterized by an XRPD pattern comprising degree 2θ-reflections (±0.2 degrees 2θ) at 4.6°, 14.6°, and 18.3°.

12. The crystalline form of claim 11, wherein the XRPD comprises degree 2θ-reflections (±0.2 degrees 2θ) at 4.6°, 5.0°, 14.6°, 15.7°, 18.3°, and 26.2°.

13. The crystalline form of claim 11, wherein the XRPD comprises degree 2θ-reflections (±0.2 degrees 2θ) at 4.6°, 5.0°, 8.3°, 14.6°, 15.7°, 16.6°, 17.5°, 18.3°, and 26.2°.

14. A pharmaceutical composition comprising:

(i) the crystalline form of claim 11; and (ii) a pharmaceutically acceptable excipient.

15. A method of making the crystalline form of claim 11, wherein the method comprises (i) slurrying the compound of Formula (I) in a solvent and (ii) isolating the solvate or the crystalline form of Formula (I).

16. A crystalline form of a compound of Formula (I)

Formula (I)

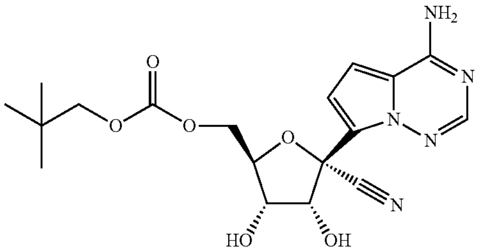

wherein the crystalline form is characterized by an XRPD pattern comprising degree 2θ-reflections (±0.2 degrees 2θ) at 5.3°, 18.7°, and 20.0°.

17. The crystalline form of claim 16, wherein the XRPD pattern comprises degree 2θ-reflections (±0.2 degrees 2θ) at 5.3°, 14.3°, 15.4°, 18.7°, 20.0°, and 25.1°.

18. The crystalline form of claim 16, wherein the XRPD pattern comprises degree 2θ-reflections (±0.2 degrees 2θ) at 5.3°, 14.3°, 14.6°, 15.4°, 17.0°, 18.7°, 20.0°, 25.1°, and 25.9°.

19. The crystalline form of claim 16, wherein the crystalline form is characterized by a differential scanning calorimetry (DSC) pattern comprising an endothermic transition with an onset at about 162° C.

20. The crystalline form of claim 16, wherein the crystalline form is unsolvated.

21. A pharmaceutical composition comprising:

(i) the crystalline form of claim 16; and (ii) a pharmaceutically acceptable excipient.

22. A method of making the crystalline form of claim 16, wherein the method comprises drying a solvate of a compound of Formula (I), a crystalline form of an ethanol solvate of a compound of Formula (I) wherein the crystalline form of the ethanol solvate is characterized by an XRPD pattern comprising degree 2θ-reflections (±0.2 degrees 2θ) at 5.4°, 15.2°, and 23.8°, or a crystalline form of an acetonitrile solvate of a compound of Formula (I) wherein the crystalline form of the acetonitrile solvate is characterized by an XRPD pattern comprising degree 2θ-reflections (±0.2 degrees 2θ) at about 4.6°, 14.6°, and 18.3°.

23. A crystalline form of a compound of Formula (I)

Formula (I)

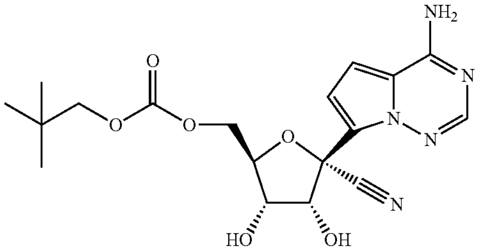

wherein the crystalline form is characterized by an XRPD pattern comprising degree 2θ-reflections (±0.2 degrees 2θ) at 5.1°, 10.3°, and 15.2°.

24. The crystalline form of claim 23, wherein the XRPD comprises degree 2θ-reflections (±0.2 degrees 2θ) at 5.1°, 10.3°, 14.7°, 15.2°, 17.3°, and 26.2°.

25. The crystalline form of claim 23, wherein the XRPD comprises degree 2θ-reflections (±0.2 degrees 2θ) at 5.1°, 10.3°, 11.4°, 13.8°, 14.7°, 15.2°, 17.3°, 25.8°, and 26.2°.

26. The crystalline form of claim 23, wherein the crystalline form is characterized by a differential scanning calorimetry pattern comprising a first endothermic transition at about 149° C. followed by an immediate exotherm and a second endotherm is observed with an onset at about 161° C.

27. The crystalline form of claim 23, wherein the crystalline form is unsolvated.

28. A pharmaceutical composition comprising:

(i) the crystalline form of claim 23; and (ii) a pharmaceutically acceptable excipient.

29. A method of making the crystalline form of claim 23, wherein the method comprises drying a solvate of a compound of Formula (I), a crystalline form of an ethanol solvate of a compound of Formula (I) wherein the crystalline form of the ethanol solvate is characterized by an XRPD pattern comprising degree 2θ-reflections (±0.2 degrees 2θ) at 5.4°, 15.2°, and 23.8°, or a crystalline form of an acetonitrile solvate of a compound of Formula (I) wherein the crystalline form of the acetonitrile solvate is characterized by an XRPD pattern comprising degree 2θ-reflections (±0.2 degrees 2θ) at about 4.6°, 14.6°, and 18.3°.

30. A method of treating a viral infection in a human in need thereof, wherein the method comprises administering to the human a solvate of a compound of Formula (I) wherein the solvate is an organic solvent solvate or hydrate, a crystalline form of an ethanol solvate of a compound of Formula (I) wherein the crystalline form of the ethanol solvate is characterized by an XRPD pattern comprising degree 2θ-reflections (±0.2 degrees 2θ) at 5.4°, 15.2°, and 23.8°, a crystalline form of an acetonitrile solvate of a compound of Formula (I) wherein the crystalline form of the acetonitrile solvate is characterized by an XRPD pattern comprising degree 2θ-reflections (±0.2 degrees 2θ) at about 4.6°, 14.6°, and 18.3°, a crystalline form of a compound of Formula (I) characterized by an XRPD pattern comprising degree 2θ-reflections (±0.2 degrees 2θ) at 5.3°, 18.7°, and 20.0°, or a crystalline form of a compound of Formula (I) characterized by an XRPD pattern comprising degree 2θ-reflections (±0.2 degrees 2θ) at 5.1°, 10.3°, and 15.2°;

Formula (I)

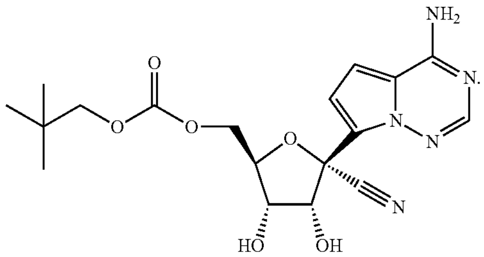

31. The method of claim 30, wherein the method comprises administering to the human at least one additional therapeutic or prophylactic agent.

32. The method of claim 31, wherein the additional therapeutic or prophylactic agent is cobicistat, molnupiravir, nirmatrelvir, ritonavir, or a combination thereof.

33. The method of claim 30, wherein the viral infection is a coronavirus infection, a pneumoviridae virus infection, a picornaviridae virus infection, an enterovirus infection, a flaviviridae virus infection, a filoviridae virus infection, an orthomyxovirus infection, an influenza virus infection, or a paramyxoviridae virus infection.

* * * * *